US012706224B2

(12) United States Patent
Smurro

(10) Patent No.: US 12,706,224 B2
(45) **Date of Patent: *Aug. 11, 2026**

(54) COGNITIVE COMMUNICATIONS, COLLABORATION, CONSULTATION, AND INSTRUCTION WITH ADAPTIVE AGENTIC AI, AUGMENTED GENERATIVE INTELLIGENCE AND NEUROSYNAPTIC COGNITION NETWORKS

(71) Applicant: James Paul Smurro, San Clemente, CA (US)

(72) Inventor: James Paul Smurro, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,242

(22) Filed: Apr. 15, 2024

(65) Prior Publication Data

US 2024/0266074 A1 Aug. 8, 2024

Related U.S. Application Data

(63) Continuation-in-part of application No. 17/353,791, filed on Jun. 21, 2021, now Pat. No. 11,961,624, (Continued)

(51) Int. Cl.
*G16H 80/00* (2018.01)
*G16H 30/40* (2018.01)
*G16H 50/20* (2018.01)

(52) U.S. Cl.
CPC ............. *G16H 80/00* (2018.01); *G16H 30/40* (2018.01); *G16H 50/20* (2018.01)

(58) Field of Classification Search
CPC ......... G16H 80/00; G16H 50/20; G16H 30/40
See application file for complete search history.

(56) References Cited

U.S. PATENT DOCUMENTS 6,105,055 A * 8/2000 Pizano .................. G06Q 10/10 719/321
6,556,724 B1 * 4/2003 Chang .................. G06T 3/4092 715/275

(Continued)

*Primary Examiner* — Olisa Anwah

(57) ABSTRACT

A cognitive communications system and method enabling synchronous and asynchronous multichannel multiplexed communications, collaboration, consultation, and instruction with multimodal media and augmented generative intelligence among heterogeneous networked teams of human and machine collaborants, including agentic AI algorithms, models, and systems. The system establishes neurosynaptic network connectivity via modular clini-docks, clini-pods, and clini-ports for acquisition, transmission, and concurrent viewing of streaming imagery data at variable resolutions and frame rates. Participant cognitive collaborants recursively enrich collaboration sessions through curation, annotation, telestration, and tagging with colorized attention masking for explainable AI, encapsulating collaborated imagery, metadata, semantic annotations, and provenance into packetized vismemes stored in clinical and non-clinical knowledge repositories, vismeme vaults, and security metadata repositories. The system supports agentic task allocation, autonomous sub-agent spawning, Graph RAG retrieval, cybernetic closed-loop resilience, and tokenized vismeme workflows across clinical (computer-assisted drug design (CADD) and treatment, theranostics, digital twins, precision-guided surgery) and non-clinical (finance, defense, education, creative) domains with operational analytics for outcomes, performance, resource utilization, and cost-curve optimization.

128 Claims, 85 Drawing Sheets depicts a block diagram of the invention.

Related U.S. Application Data which is a continuation-in-part of application No. 16/450,974, filed on Jun. 24, 2019, now Pat. No. 11,043,307, which is a continuation-in-part of application No. 15/731,201, filed on May 2, 2017, now Pat. No. 10,332,639, which is a continuation-in-part of application No. 14/544,807, filed on Feb. 18, 2015, now Pat. No. 9,641,799, and a continuation-in-part of application No. 13/999,688, filed on Mar. 15, 2014, now abandoned.

(60) Provisional application No. 61/967,323, filed on Mar. 15, 2014, provisional application No. 61/852,625, filed on Mar. 15, 2013.

(56) References Cited

U.S. PATENT DOCUMENTS

| | | | | |
|---|---|---|---|---|
| 6,934,698 | B2 * | 8/2005 | Judd | G16H 30/20<br>382/128 |
| 11,978,558 | B1 * | 5/2024 | Drakos | G16H 50/70 |
| 2006/0034521 | A1 * | 2/2006 | Lindmark | G16H 30/20<br>382/232 |
| 2006/0122482 | A1 * | 6/2006 | Mariotti | H04L 12/1822<br>600/407 |
| 2011/0126127 | A1 * | 5/2011 | Mariotti | H04M 7/0027<br>715/753 |
| 2018/0039731 | A1 * | 2/2018 | Szeto | G16H 40/20 |
| 2022/0059224 | A1 * | 2/2022 | Tulley | G10L 15/26 |
| 2023/0174970 | A1 * | 6/2023 | Alvarez | G01N 15/1429<br>506/4 |
| 2023/0352149 | A1 * | 11/2023 | Furkel | G16H 30/40 |
| 2024/0153634 | A1 * | 5/2024 | Ghosh | G16H 50/20 |
| 2024/0156567 | A1 * | 5/2024 | Coulombe | A61C 5/00 |
| 2025/0201367 | A1 * | 6/2025 | Dwivedi | G06F 40/40 |

* cited by examiner

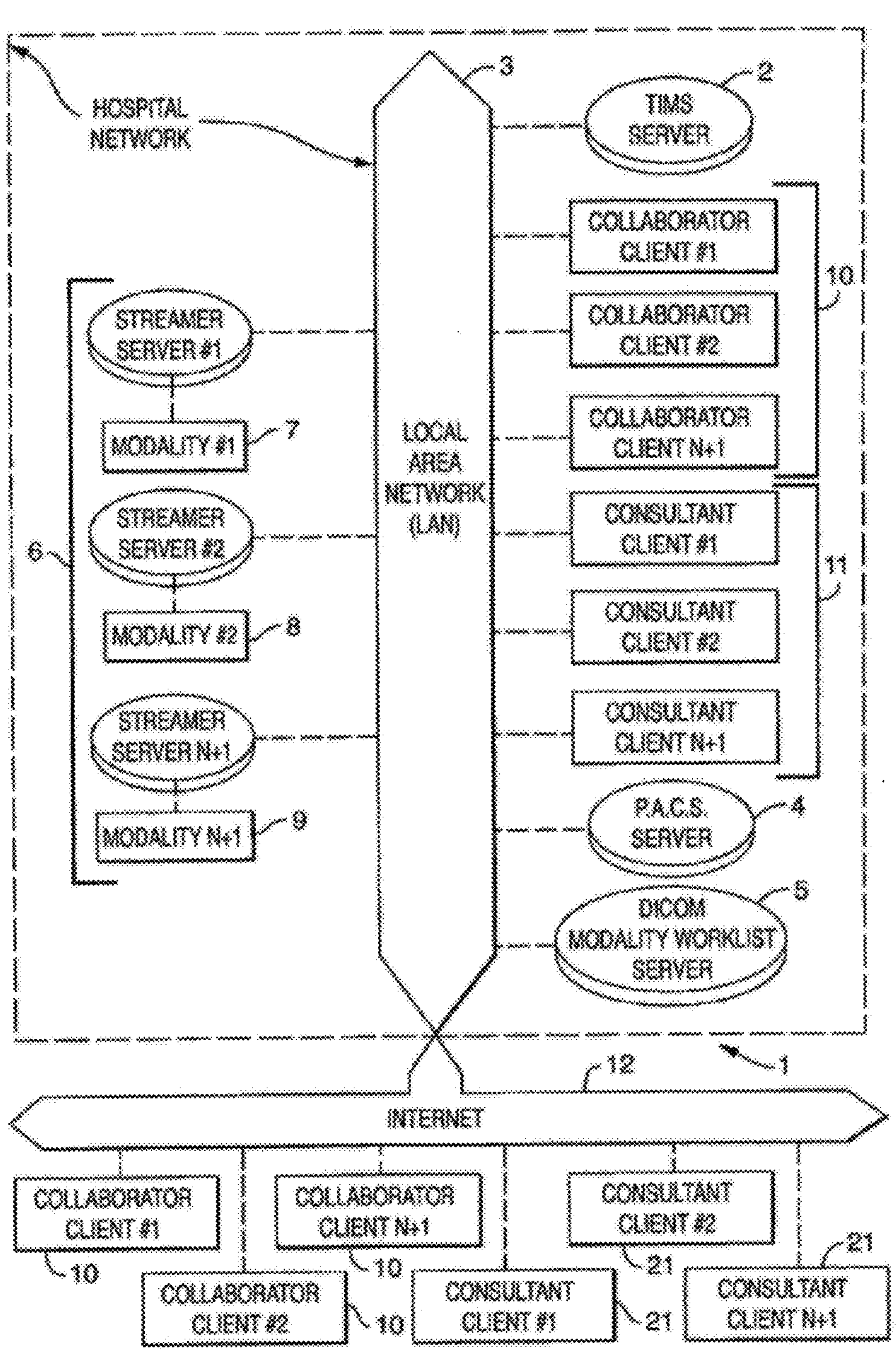
FIG. 1 depicts a block diagram of the invention.

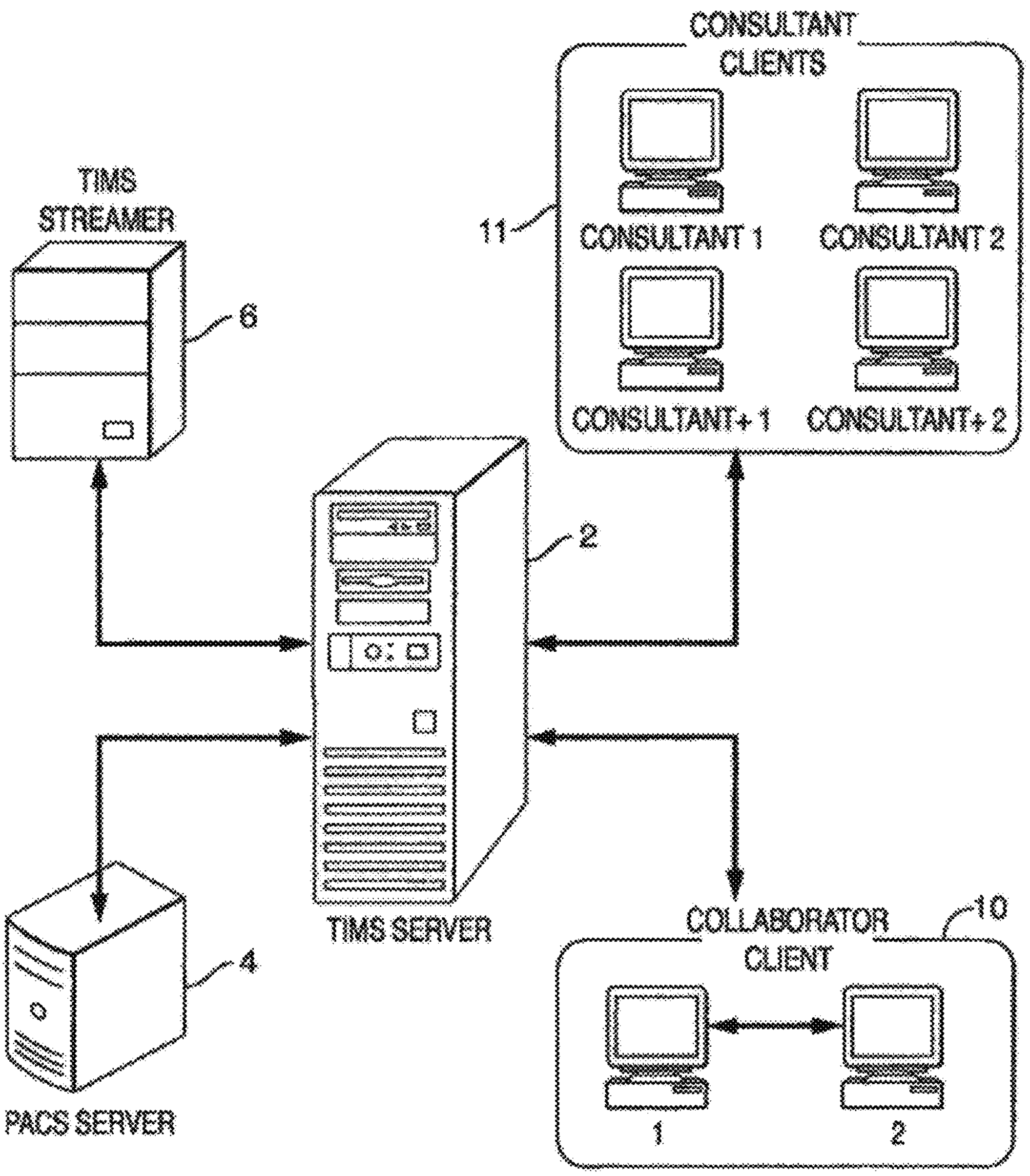
FIG. 2 depicts a block diagram of a portion of the system.

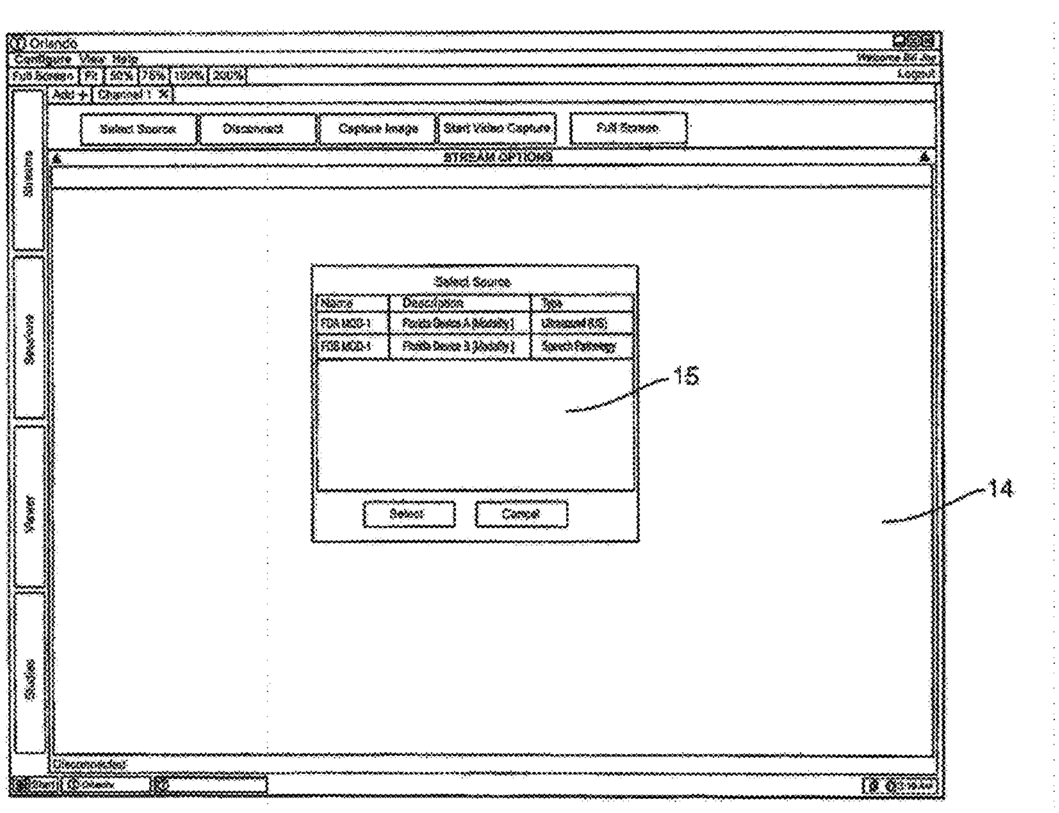
FIG. 3 depicts a graphic user interface screen shot of a cognitive collaborant workstation: client imagery source selection display.

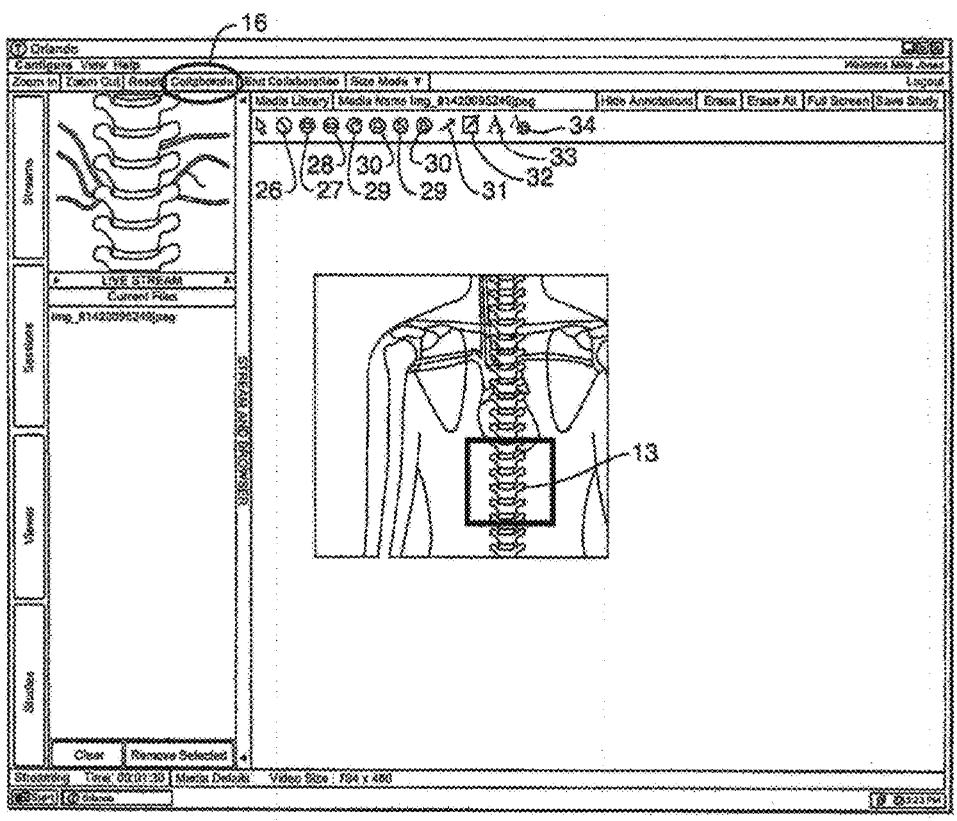
FIG. 4 depicts a graphic user interface screen shot of cognitive collaborant workstation: client source imagery with illustration tool bar and collaboration function.

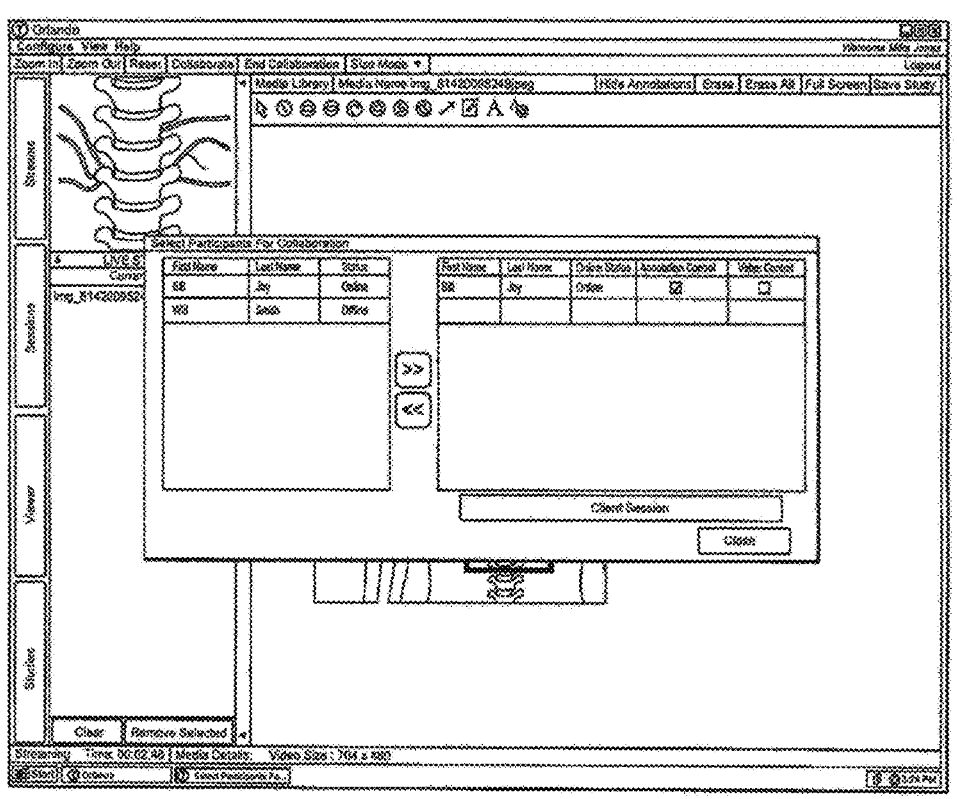
FIG. 5 depicts a graphic user interface screen shot of a cognitive collaborant workstation: client selecting participant cognitive collaborants for collaboration session.

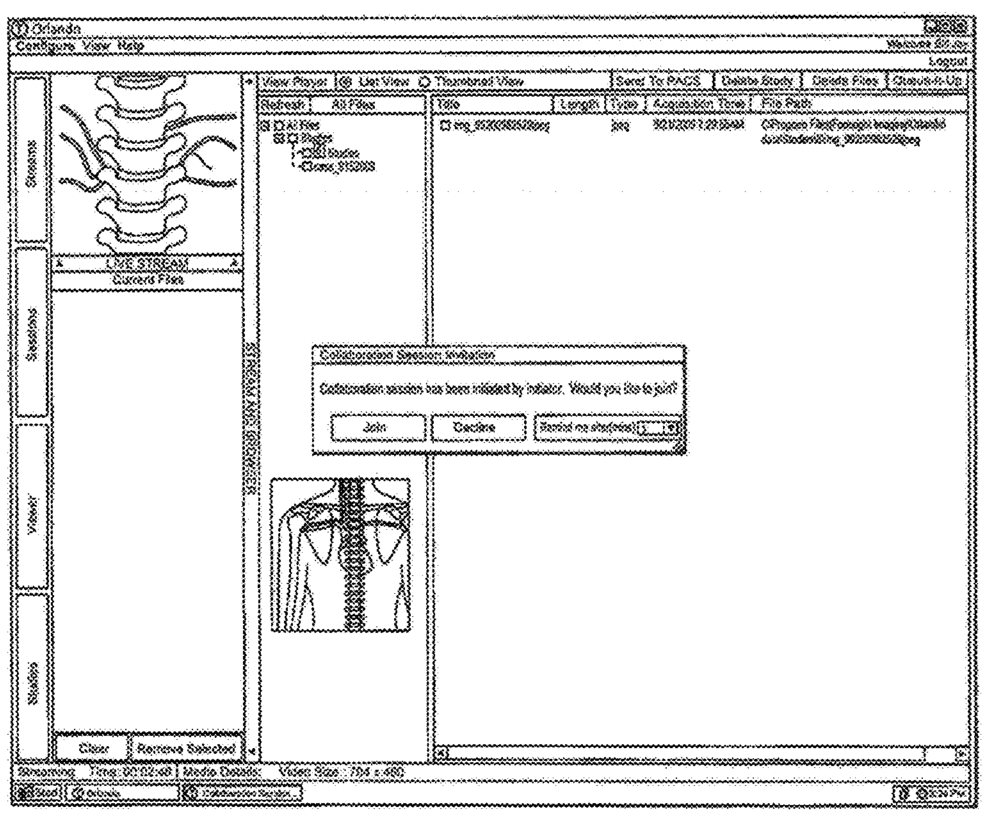
FIG. 6 depicts a graphic user interface screen shot of cognitive collaboration session initiation.

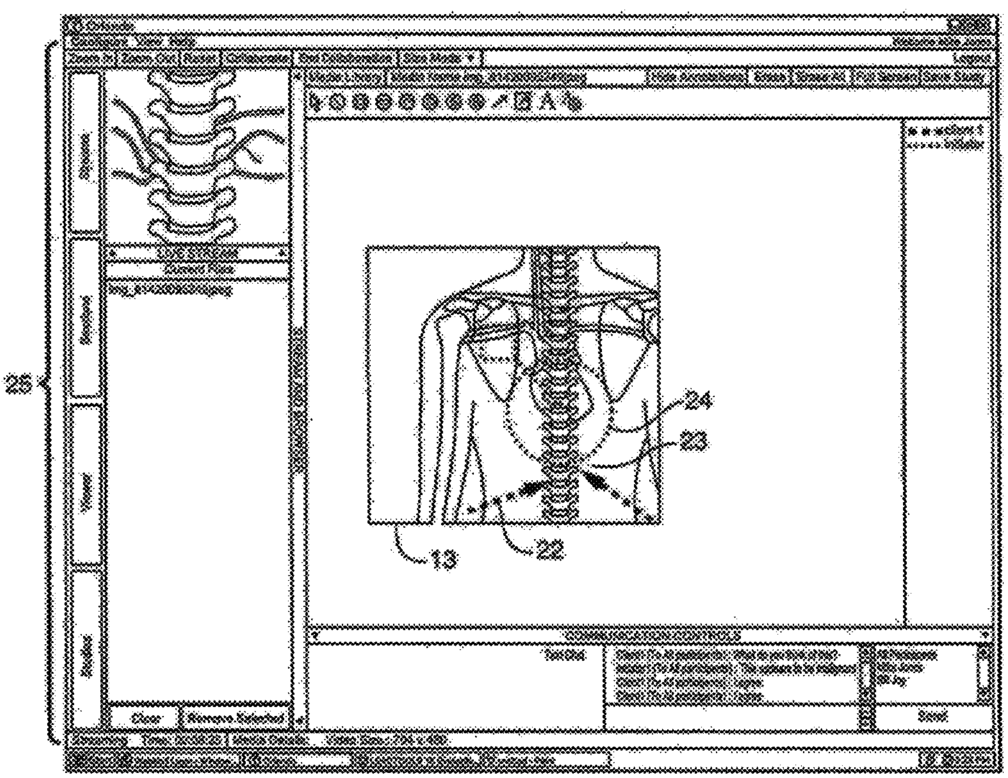
FIG. 7 depicts a graphic user interface screen shot of a cognitive collaboration session, including streaming medical imagery with annotations.

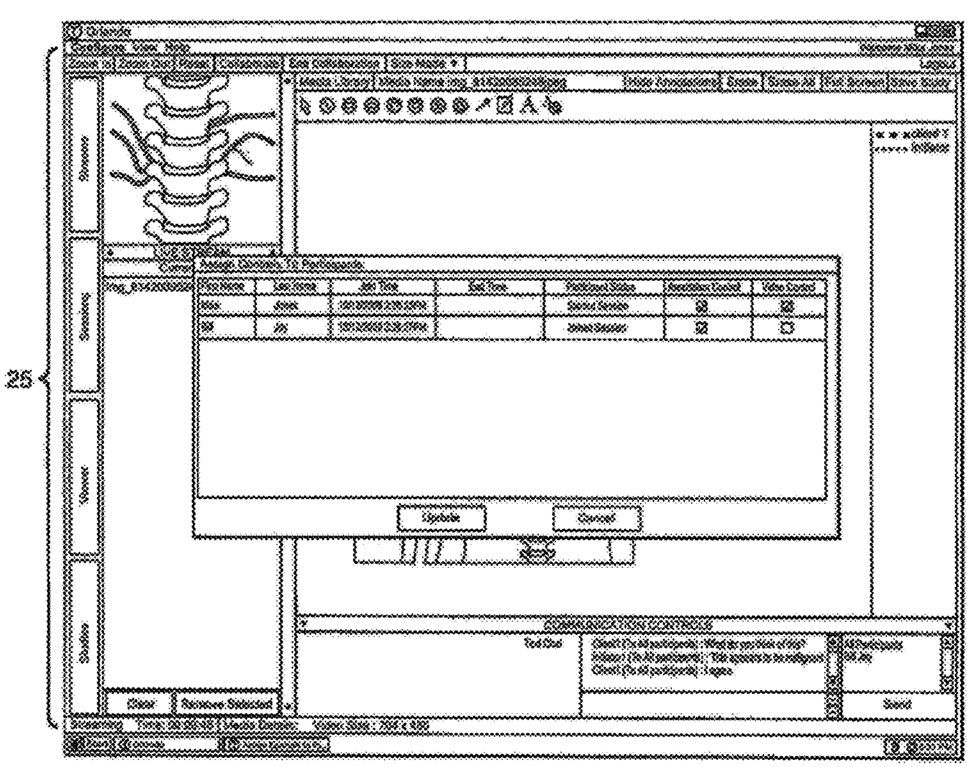
FIG. 8 depicts a graphic user interface screen shot of a cognitive collaborant workstation: client assignment of control to participant cognitive collaborant.

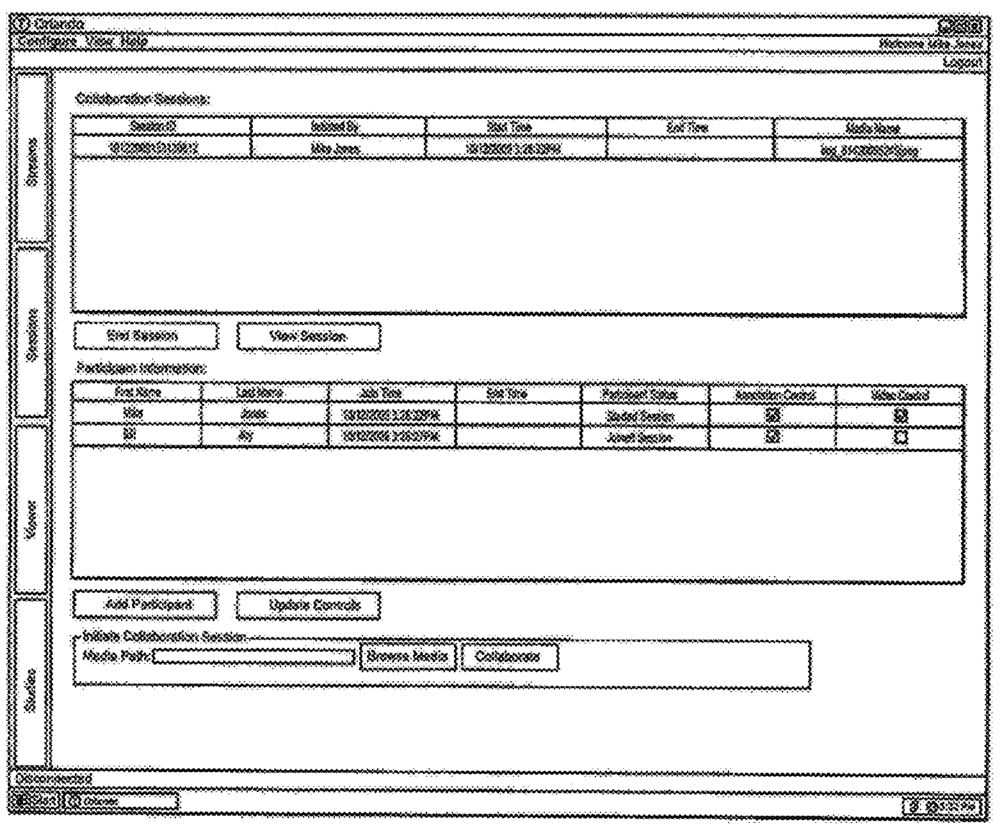
FIG. 9 depicts a graphic user interface screen shot list of multiple cognitive collaboration sessions.

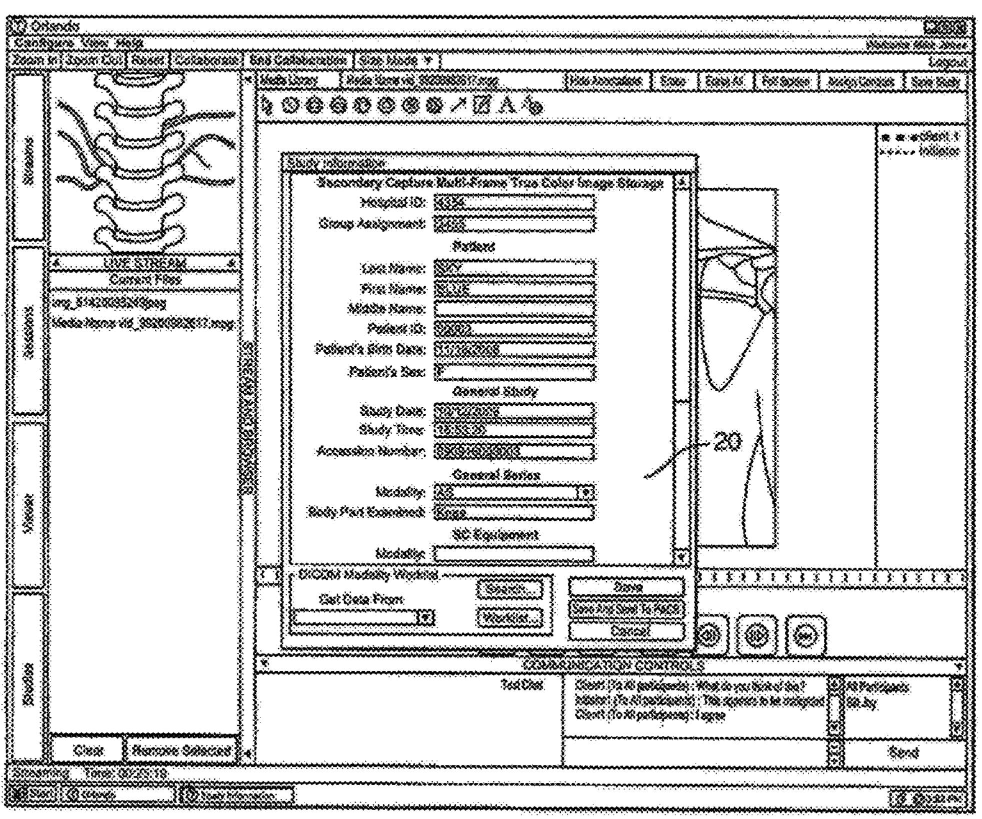
FIG. 10 depicts a graphic user interface screen shot of patient imaging study information.

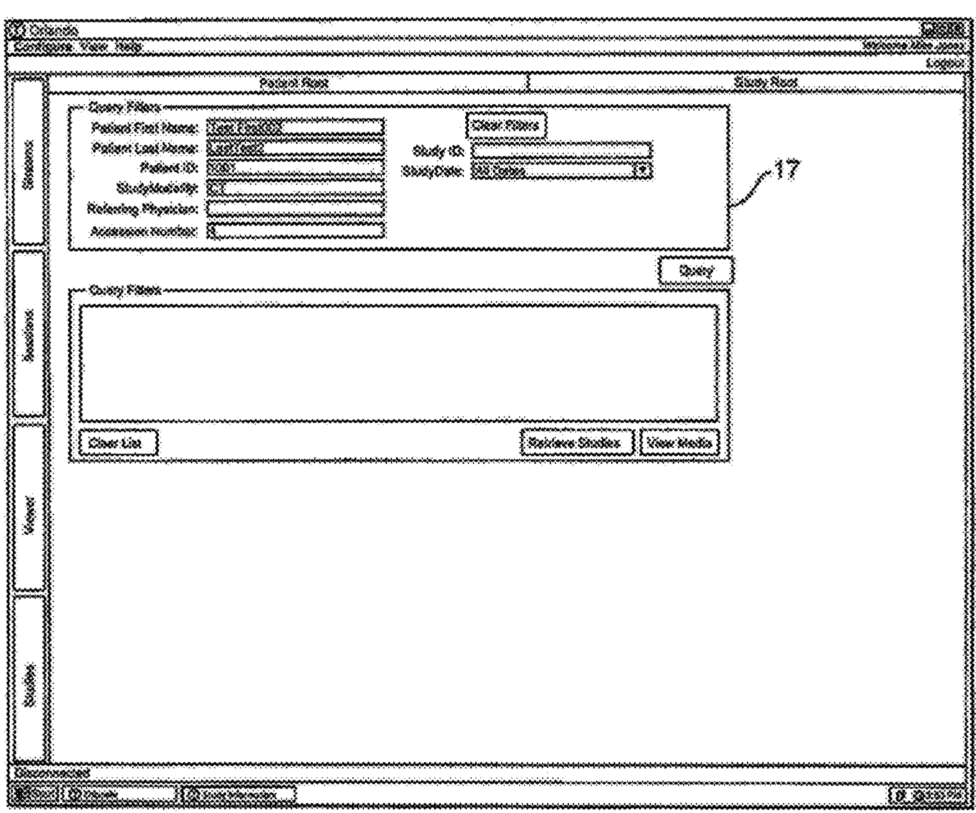
FIG. 11 depicts a graphic user interface screen shot of patient electronic medical record information.

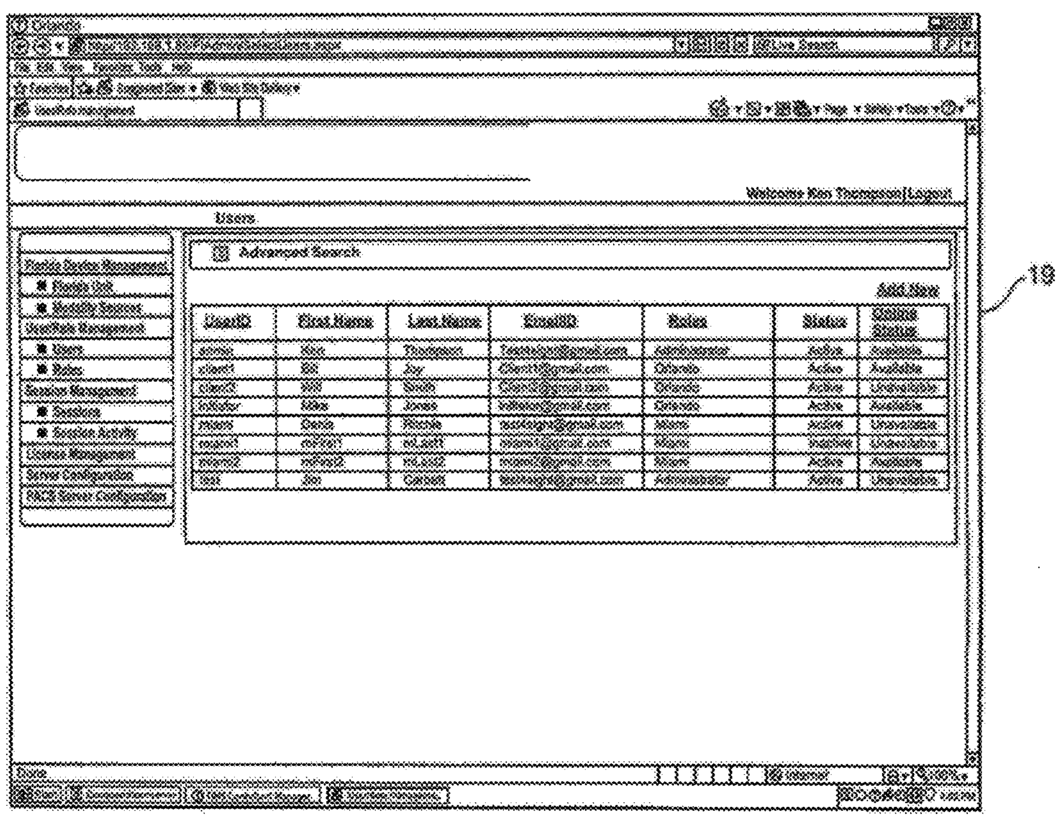
FIG. 12 depicts a graphic user interface screen shot of administrative controls.

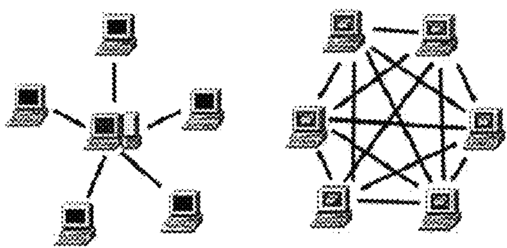
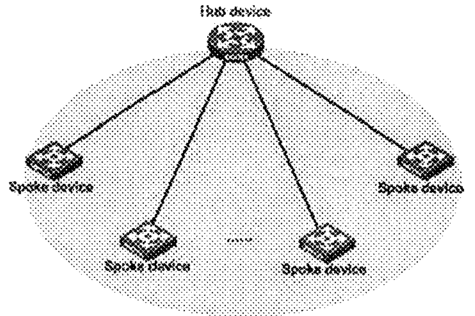
TIMS Clini-Pod deployment as Hub-n-Spoke Device Cluster for either Server-Based or Peer-to-Peer Networks
FIG. 13 depicts deployment of a hub-and-spoke device cluster for either server-based or peer-to-peer networks.

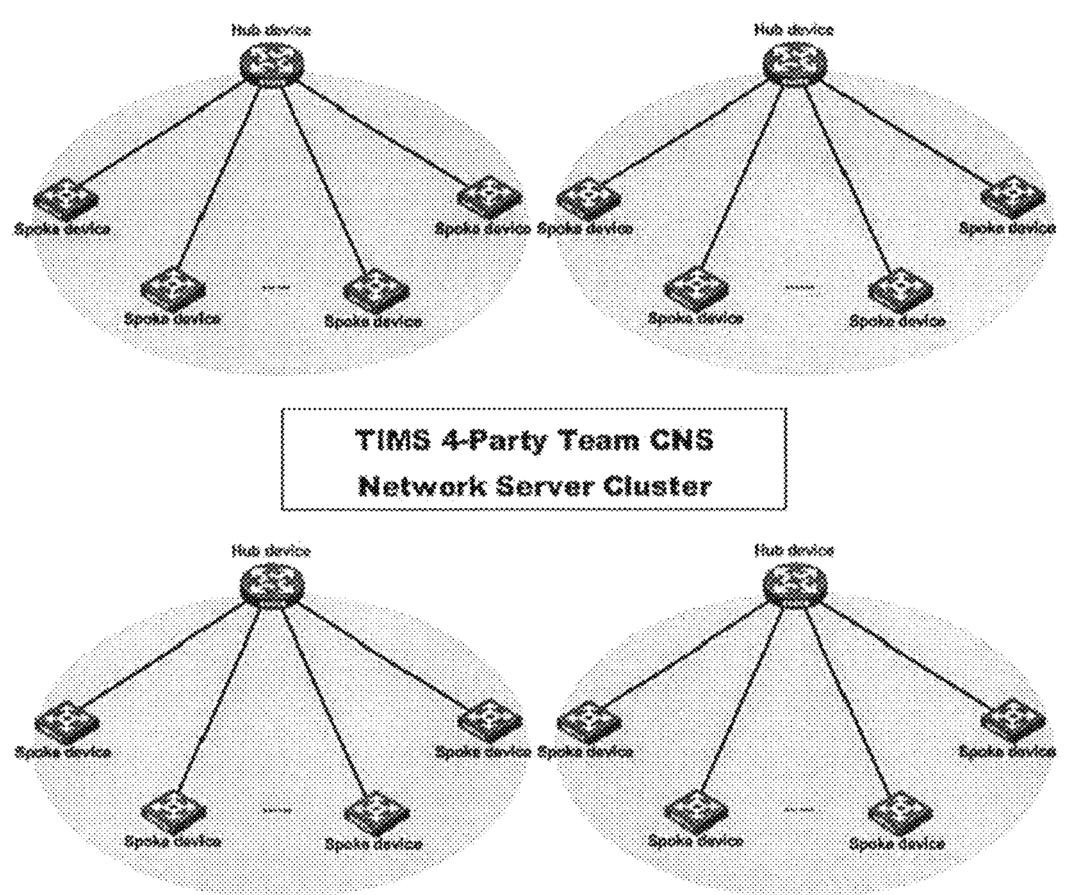
TIMS 4-Party Team CNS Network Server
Interconnecting with four TIMS Clini-Pods
FIG. 14 depicts a 4-Party Team Network Server cluster interconnecting with four Clini-Pod hub-and-spoke device clusters.

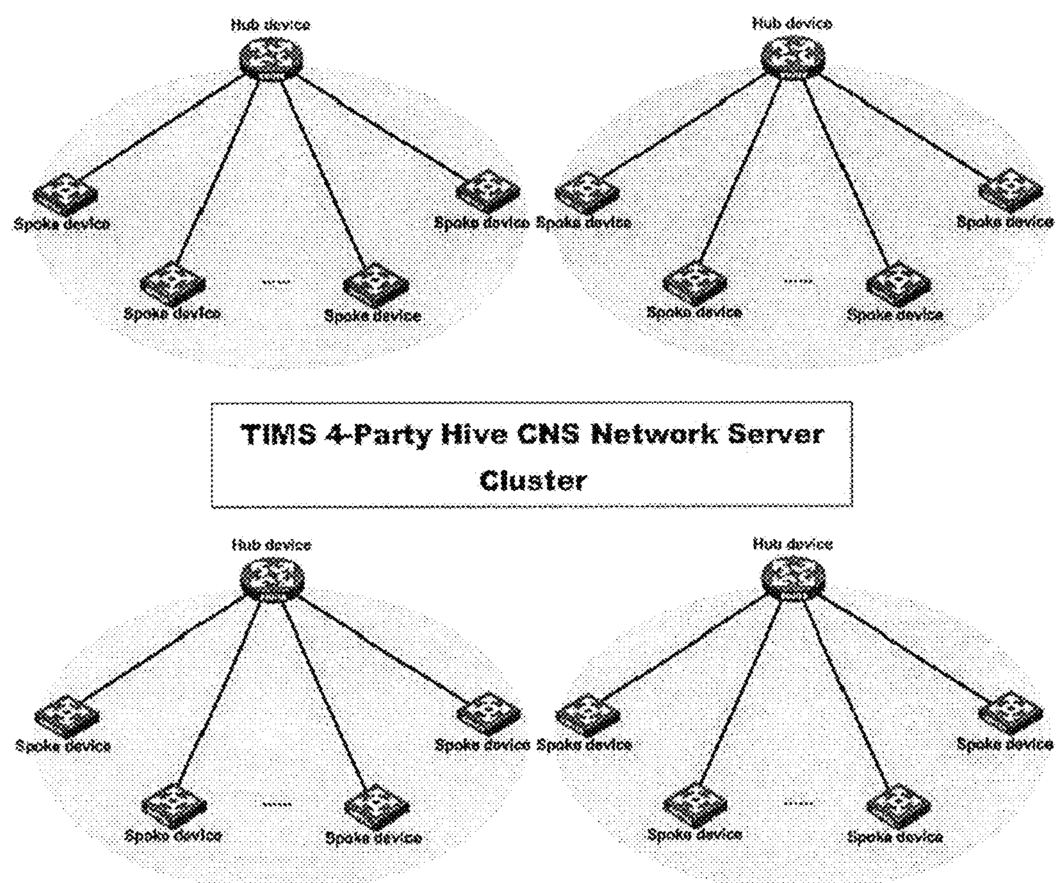
TIMS 4-Party Hive CNS Network Server Interconnecting with four TIMS Team CNS Network Servers
FIG. 15 depicts a 4-Party Hive Network Server cluster interconnecting with four Team Network Server clusters.

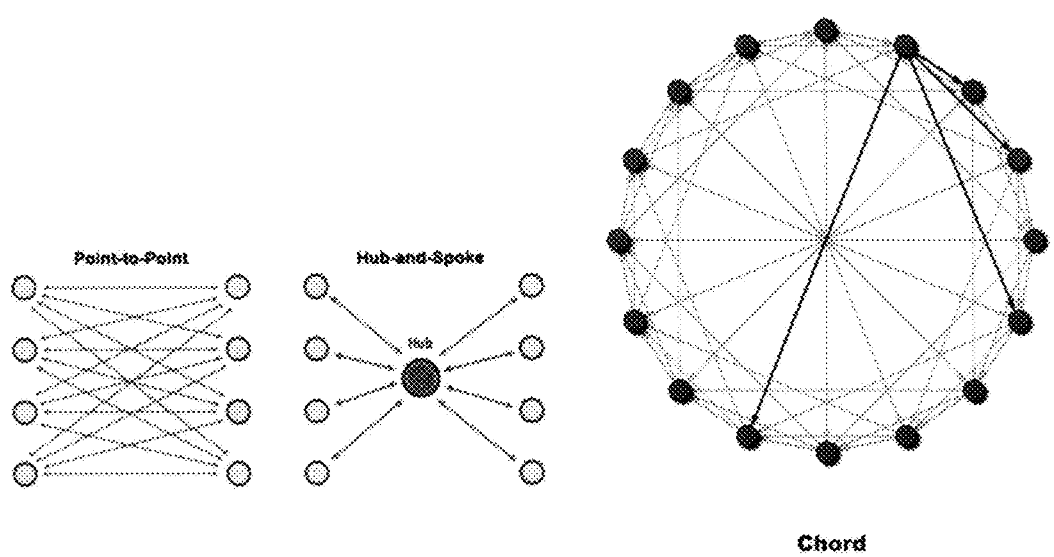
Alternative Network Architectures for TIMS Clini-Pod Deployment:
Point-to-Point vs Hub-and-Spoke vs Chord
FIG. 16 depicts Alternative Network Architectures for Clini-Pod deployment: point-to-point vs hub-and-spoke vs chord.

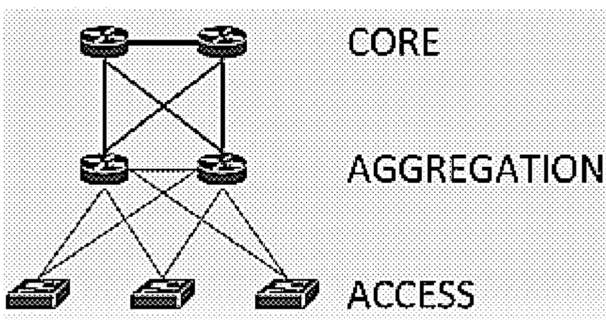
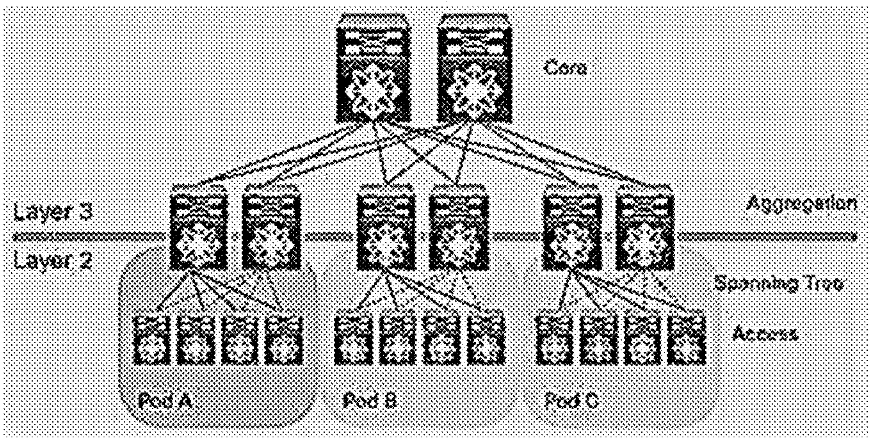
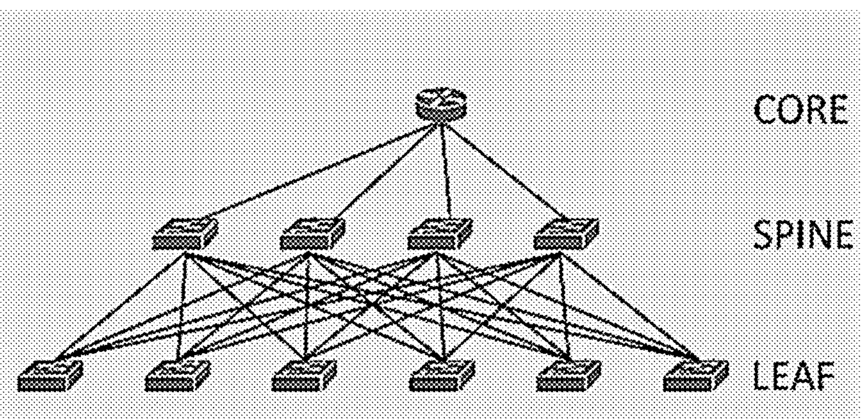
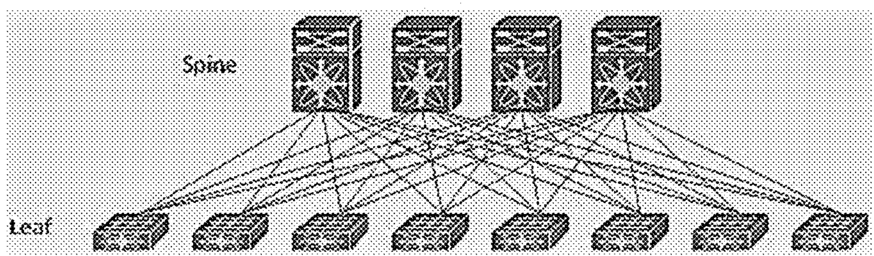
FIG. 17 depicts traditional 3-Tier Application Architectures versus Core-Spine-Leaf Network Topology.

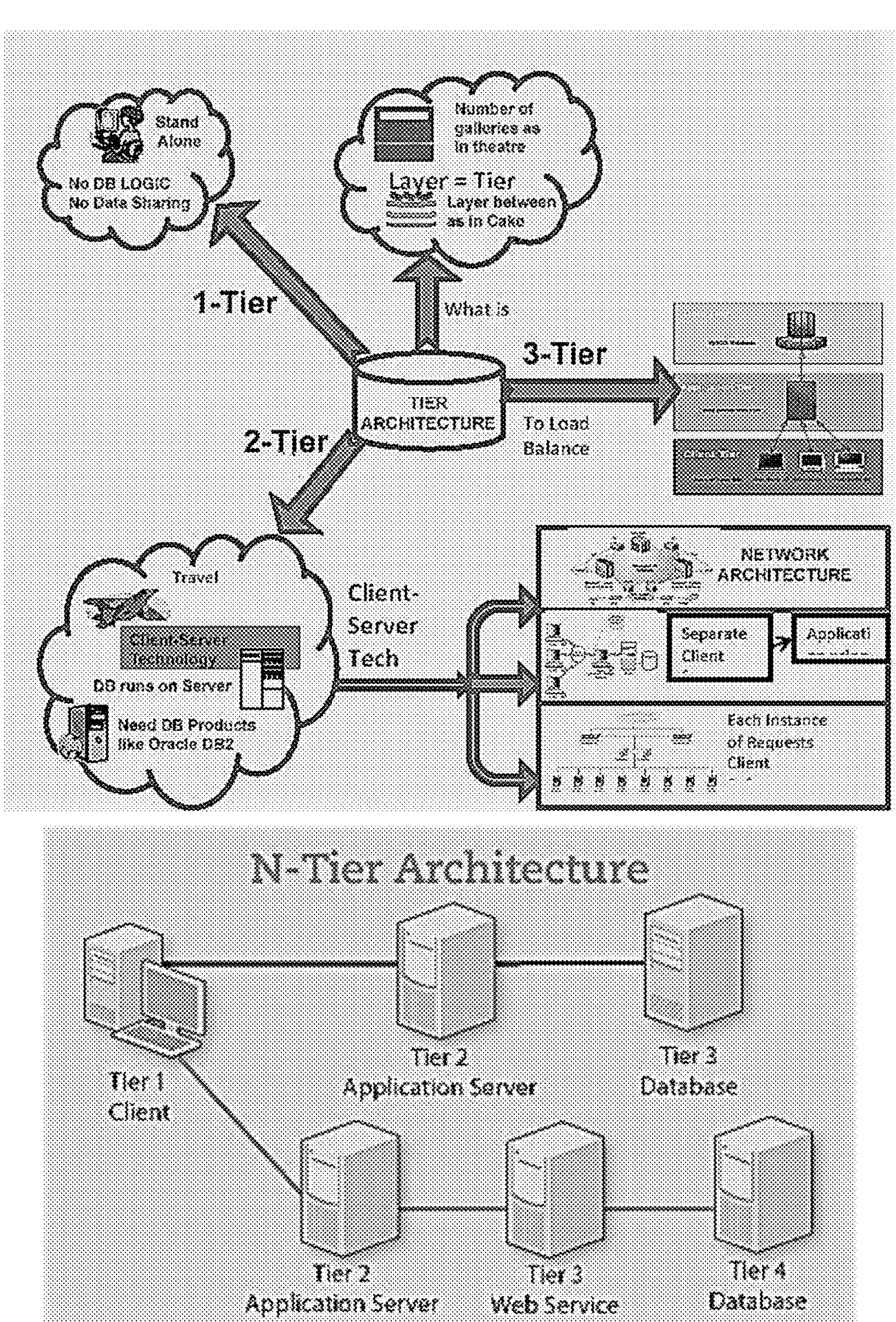
FIG. 18 depicts traditional 1-Tier, 2-Tier, 3-Tier and N-Tier Application Architectures.

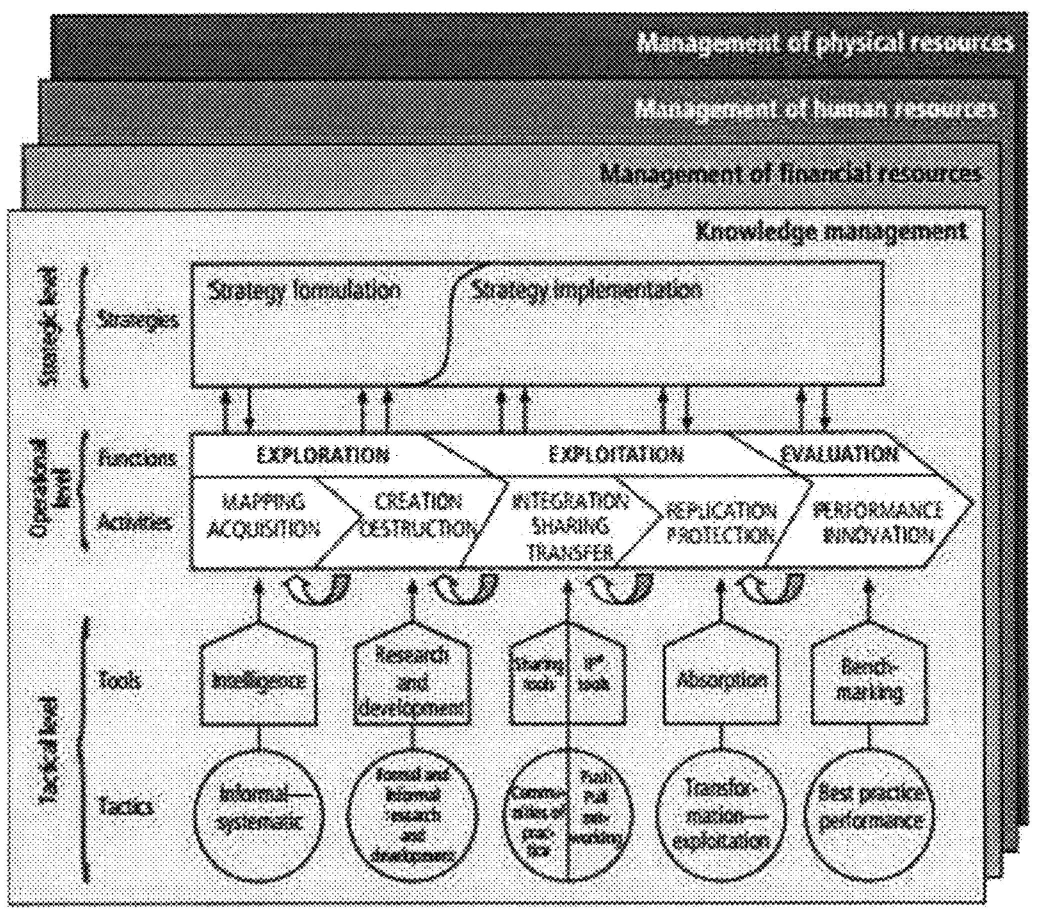
FIG. 19 depicts Value Chain Knowledge Exchange.

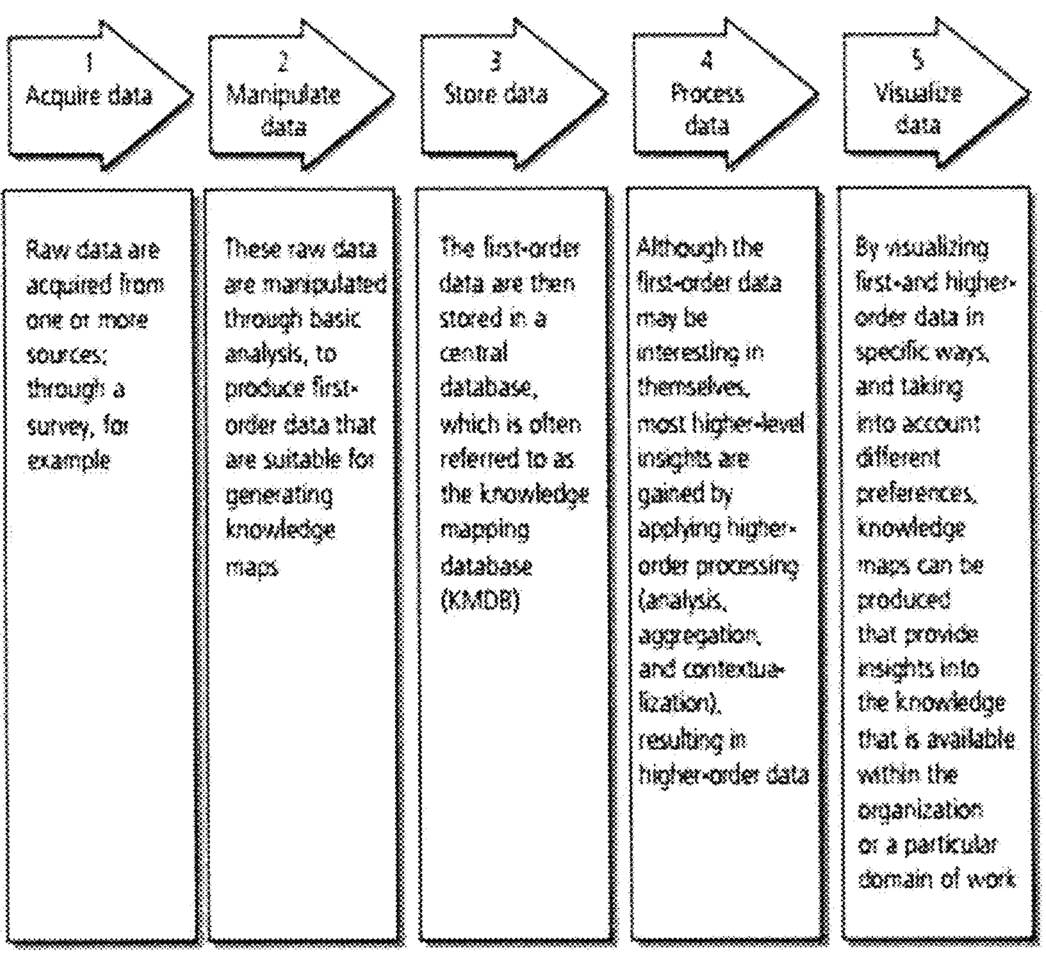
FIG. 20 depicts processes for generating insights from Knowledge Mapping and Interactive Data Visualization (data analytics, aggregation and contextualization).

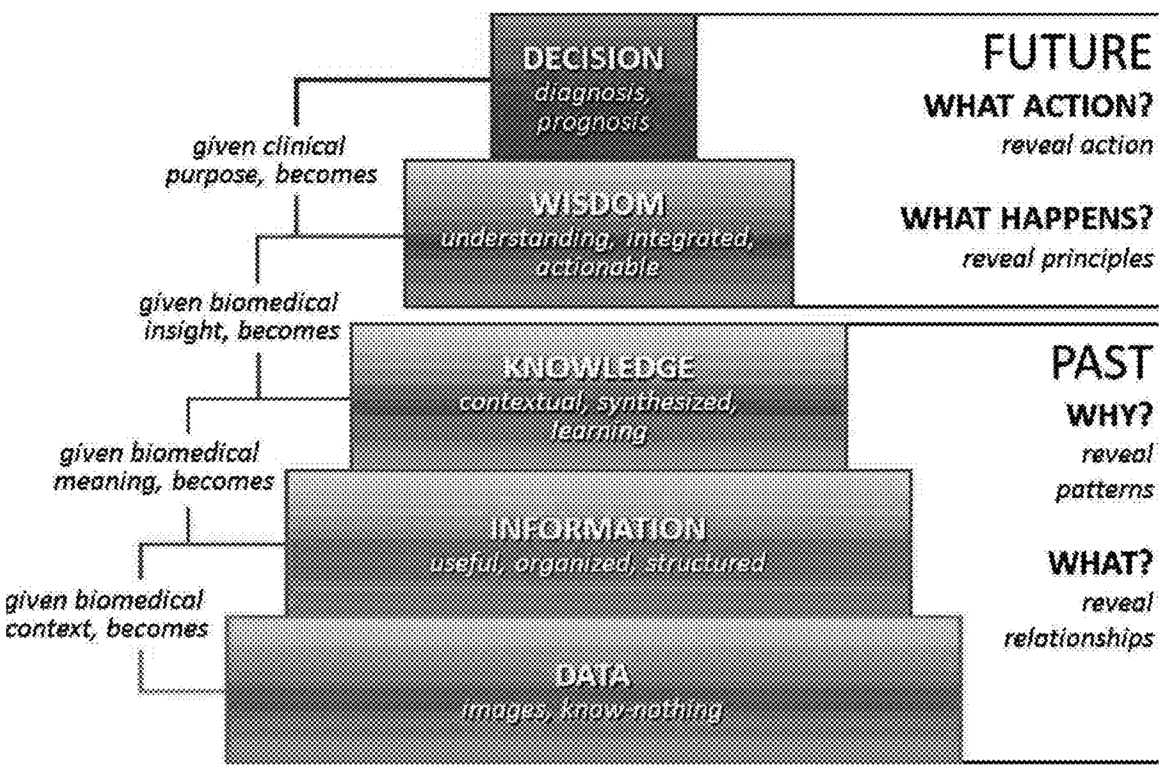
FIG. 21 depicts transforming Data into Information, then into Knowledge, Wisdom, Decision and Action.

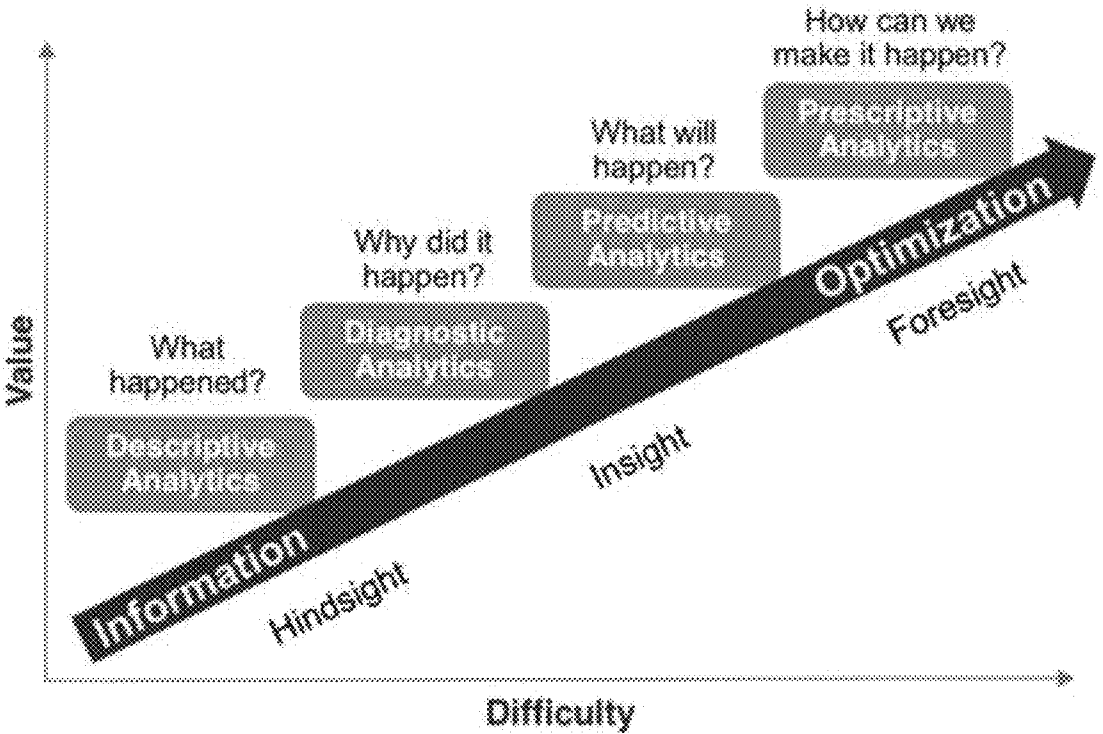
FIG. 22 depicts Information Optimization through Descriptive, Diagnostic, Predictive and Prescriptive Analytics.

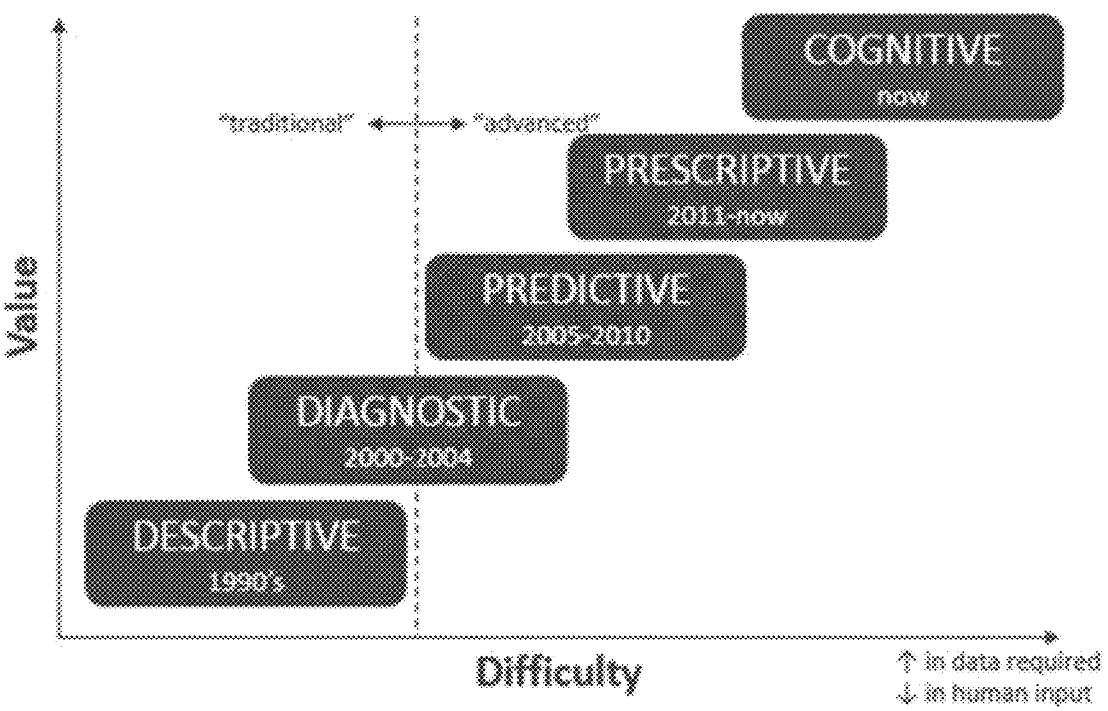
FIG. 23 depicts Cognitive Value Creation with Information Optimization and Advanced Data Analytics.

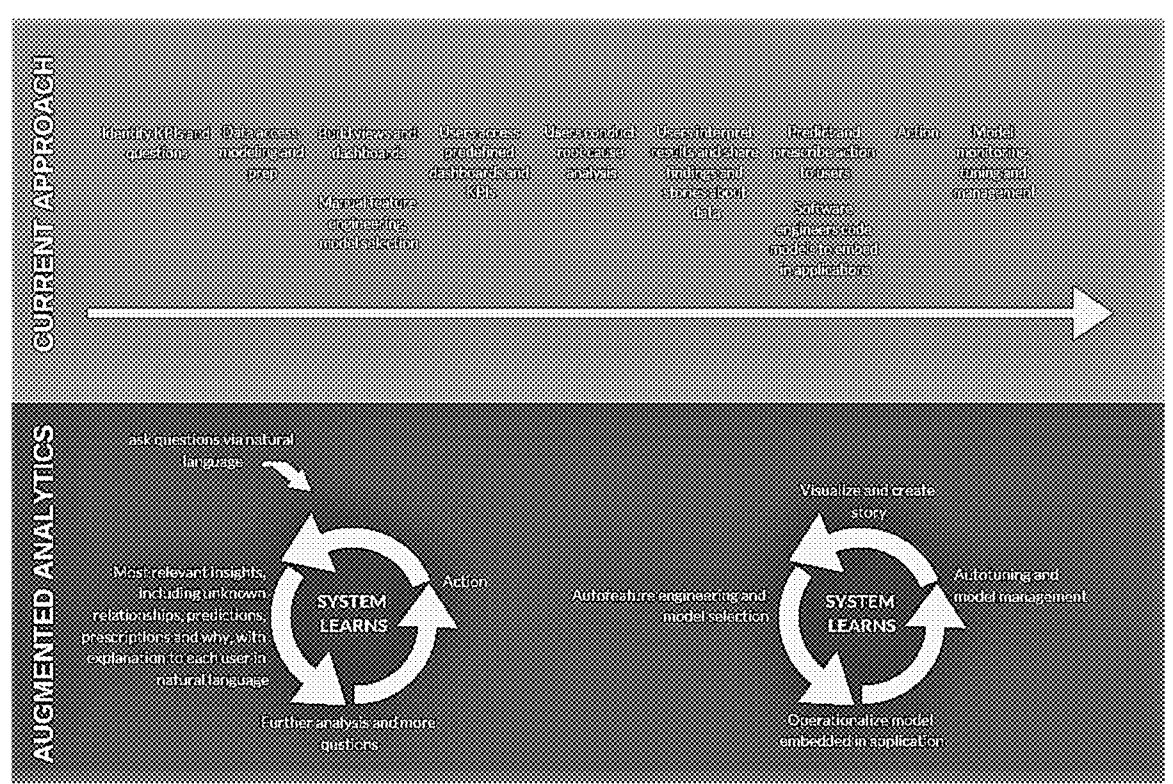
FIG. 24 depicts Adaptive Systems Learning with Augmented Analytics.

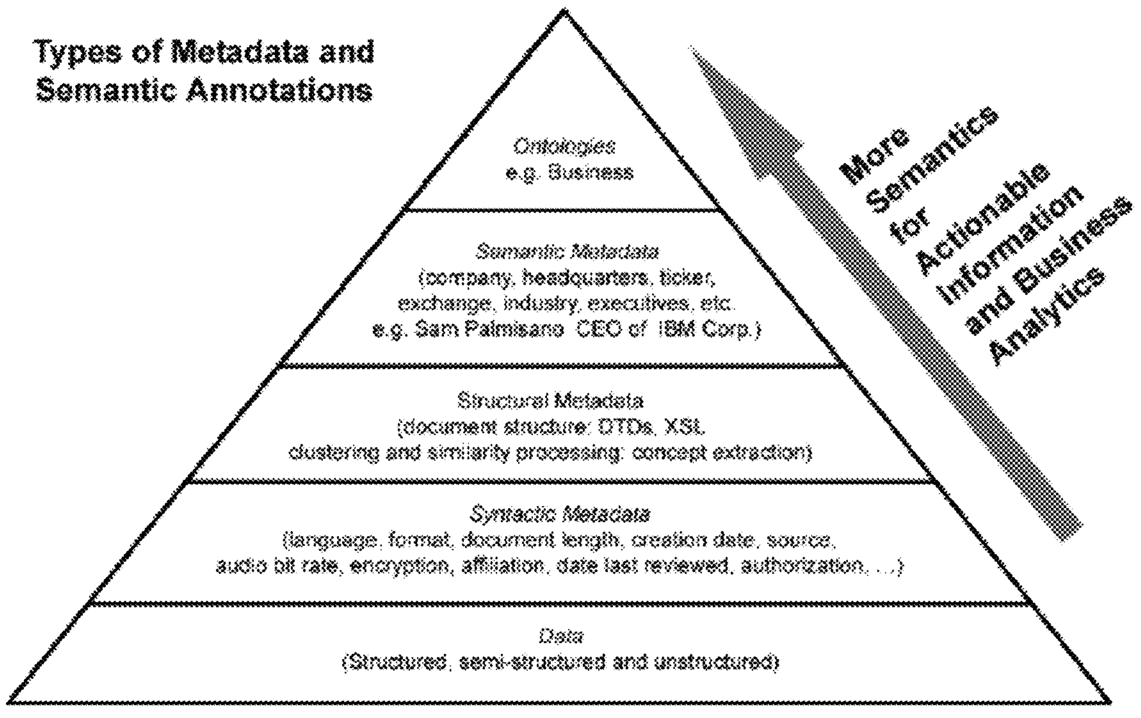
FIG. 25 depicts increasing Business Intelligence and Actionable Information with semantic metadata and annotation.

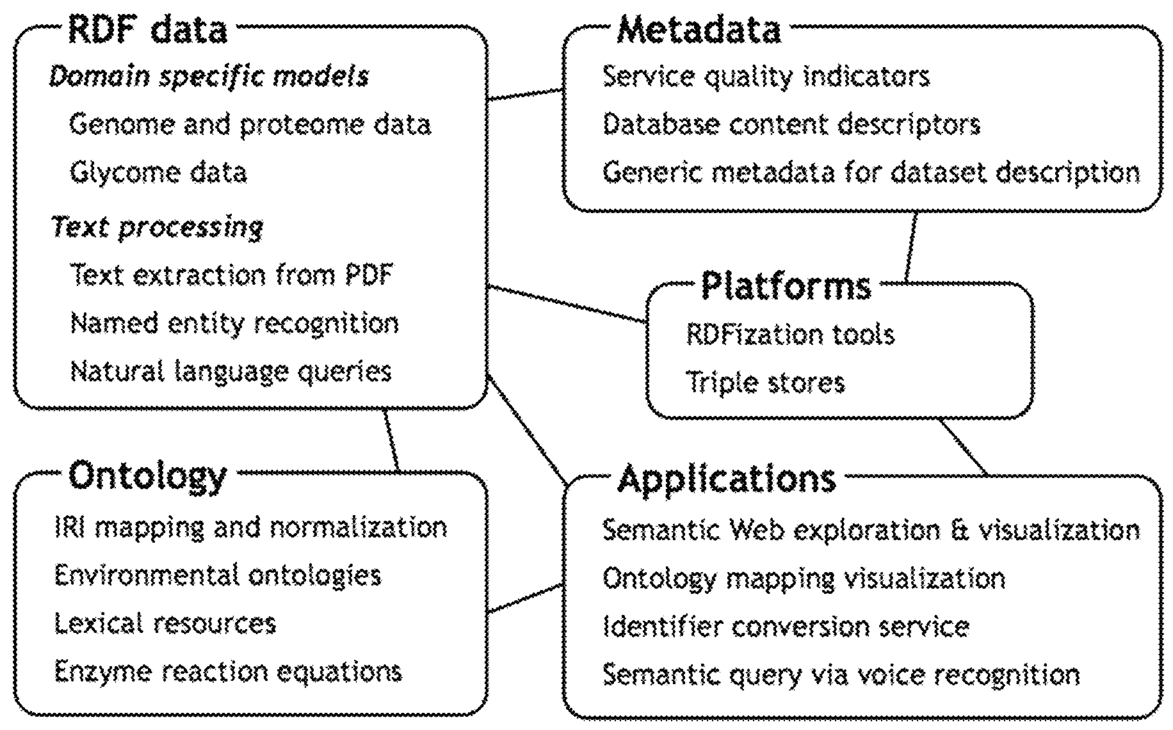
FIG. 26 depicts domain-specific semantic search, ontology mapping and visualization with RDF metadata.

Semantic Metadata Registry (MDR)

- Metadata for Semantic Interoperability
  - annotate the information models of different systems
    - with the same set of *data elements* residing in the *metadata registries*
  - early approach: bottom-up
    - takes root from several other disciplines like linguistics, compilers etc…

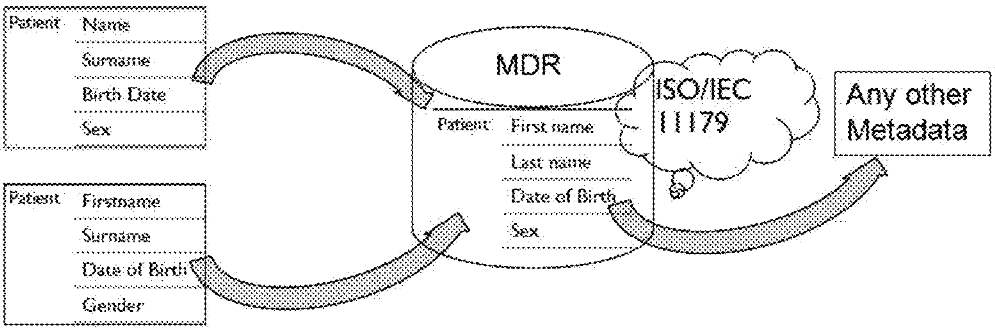

FIG. 27 depicts semantic interoperability with metadata registries and information model annotation.

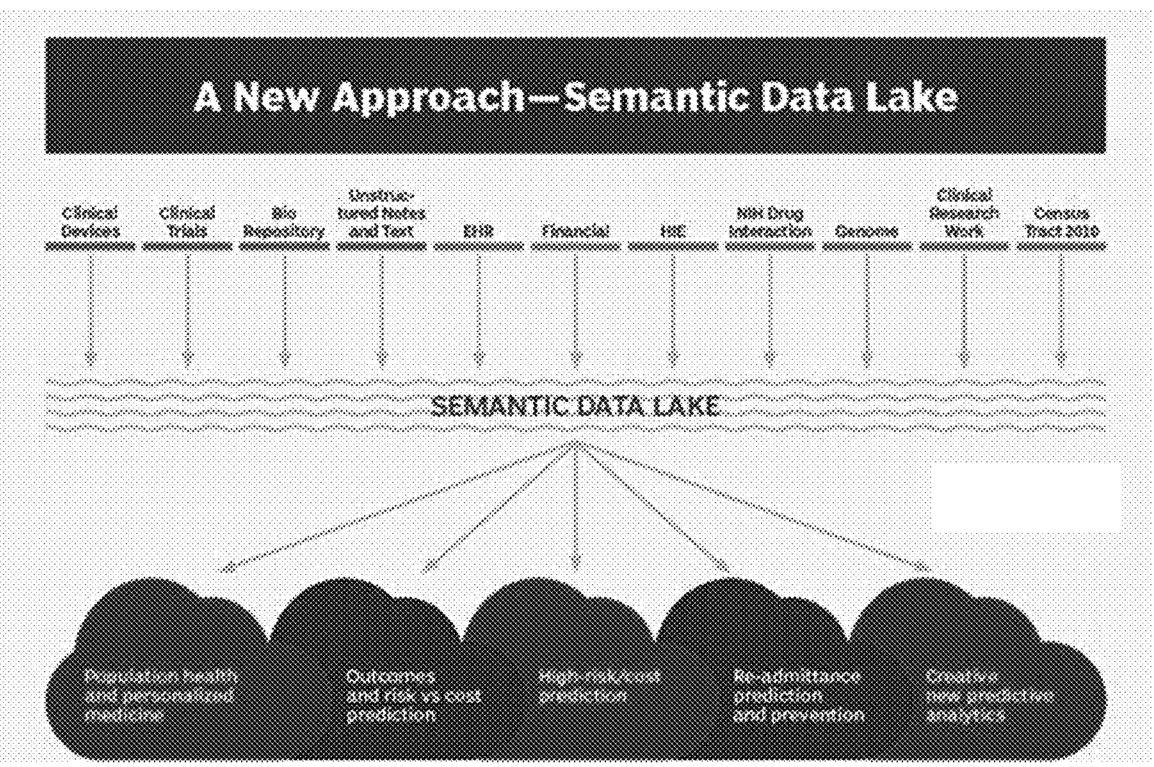
FIG. 28 depicts a semantic data lake for clinical, financial and outcomes data integration.

Semantic Trails can be built over a Web of Semantic (Meta)Data extracted (manually, semi-automatically and automatically) and gleaned from

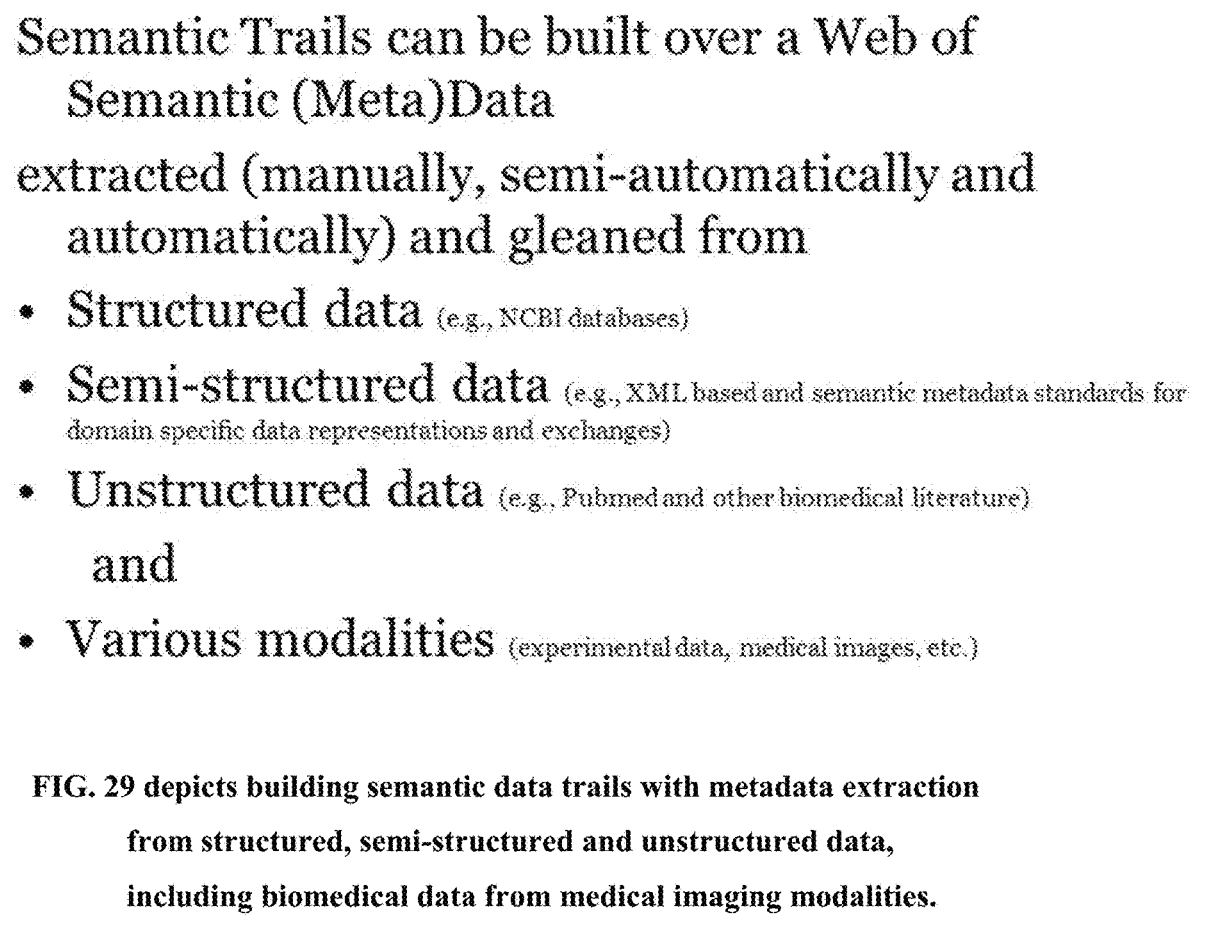

- Structured data (e.g., NCBI databases)
- Semi-structured data (e.g., XML based and semantic metadata standards for domain specific data representations and exchanges)
- Unstructured data (e.g., Pubmed and other biomedical literature)

and

- Various modalities (experimental data, medical images, etc.)

FIG. 29 depicts building semantic data trails with metadata extraction from structured, semi-structured and unstructured data, including biomedical data from medical imaging modalities.

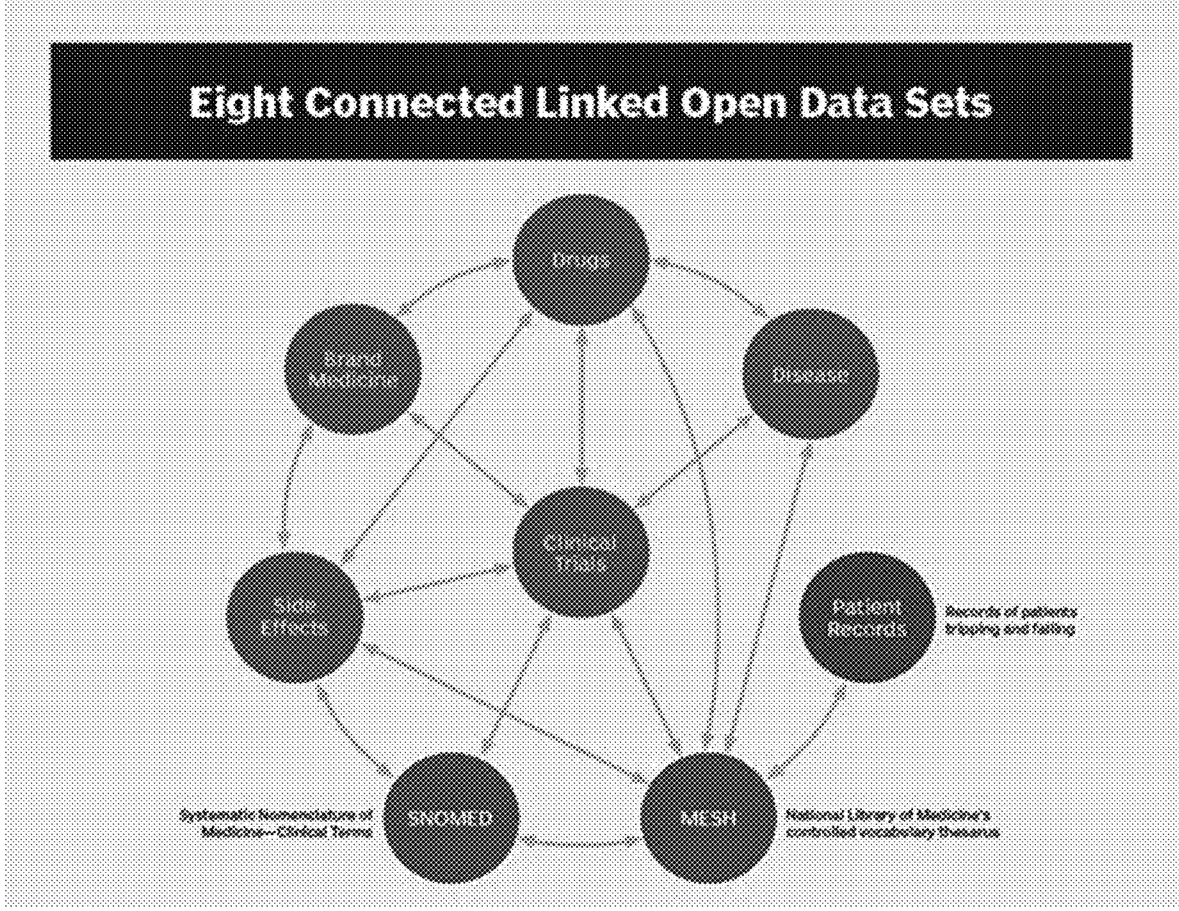
FIG. 30 depicts semantic metadata linking open and proprietary pharmaceutical data sets for clinical trials management.

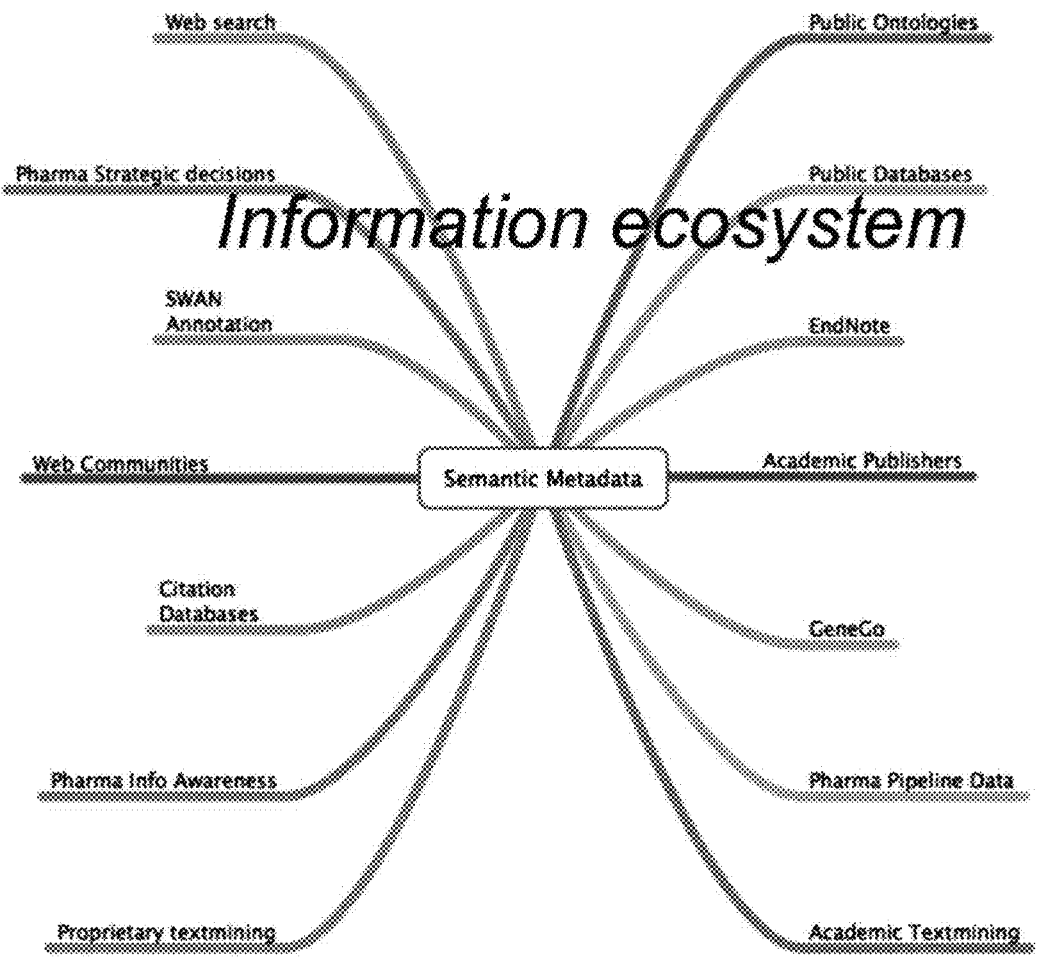
FIG. 31 depicts semantic metadata connecting an information ecosystem with open and proprietary clinical data sets for pharmaceutical development and pipeline management.

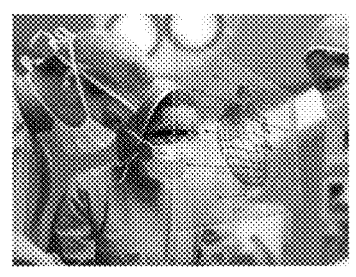
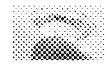
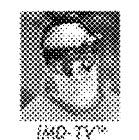
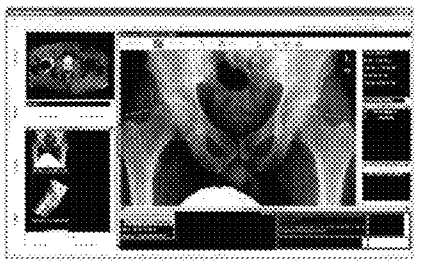
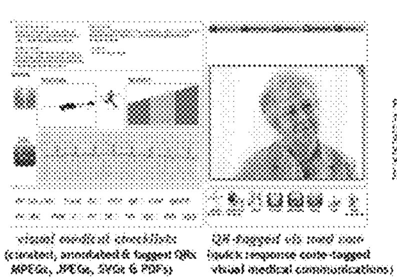
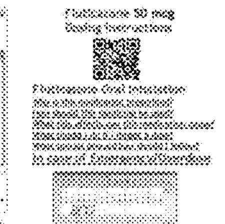
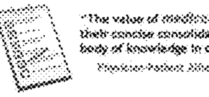
FIG. 32 depicts Visualizing Value Care: Connecting Doctors, Devices, Documents and Streams Visualizing Value Care for Collaborative Care-Giving Teams.

*New "Enterprise Imaging (EI) Paradigm"*
*Centralization - Standardization - Interoperability - Data Integrity - Governance*
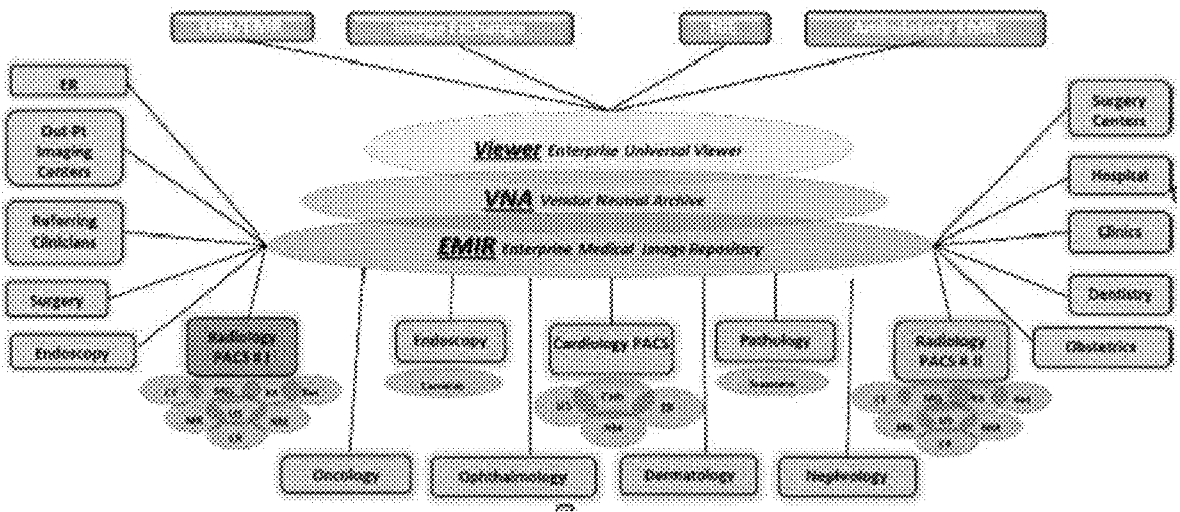
FIG. 33 depicts a New Paradigm for Collaborative Value Care with Cognitively-enriched Enterprise Imaging.

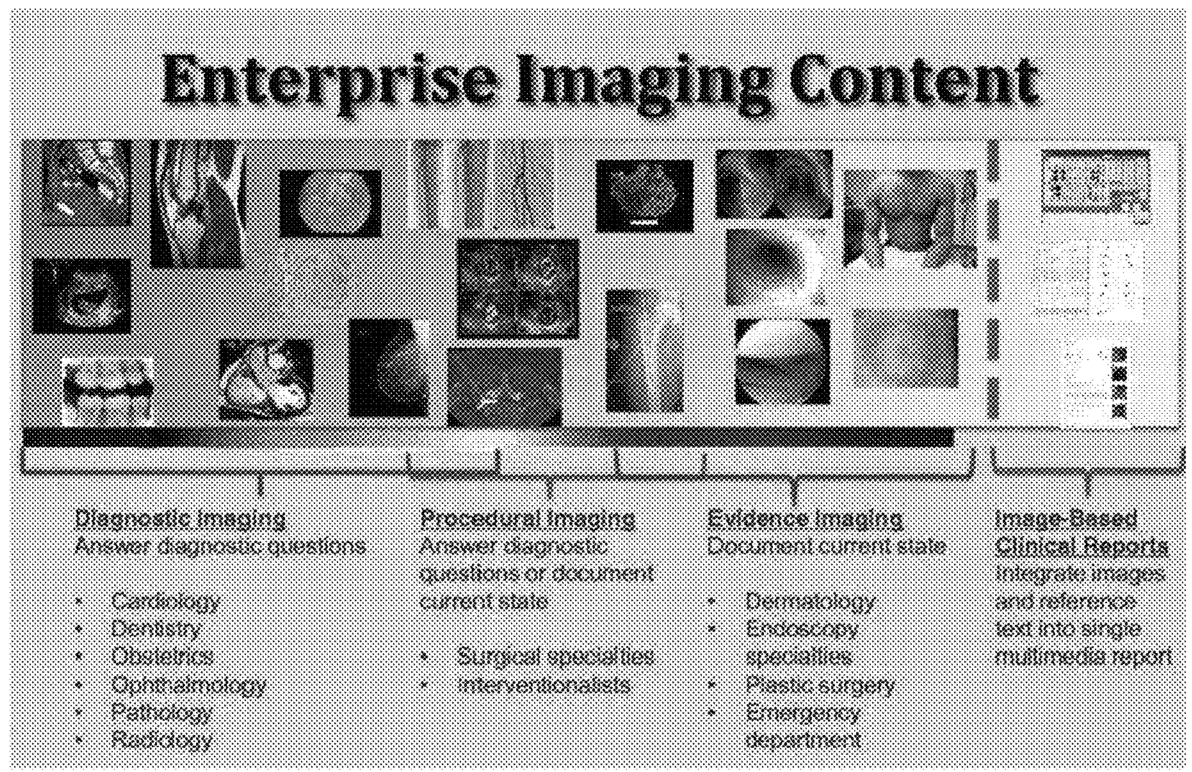
FIG. 34 depicts Cognitively-enriched Enterprise Imaging: Diagnostic, Procedural and Evidence Imaging, along with Imaged-Based Clinical Reports.

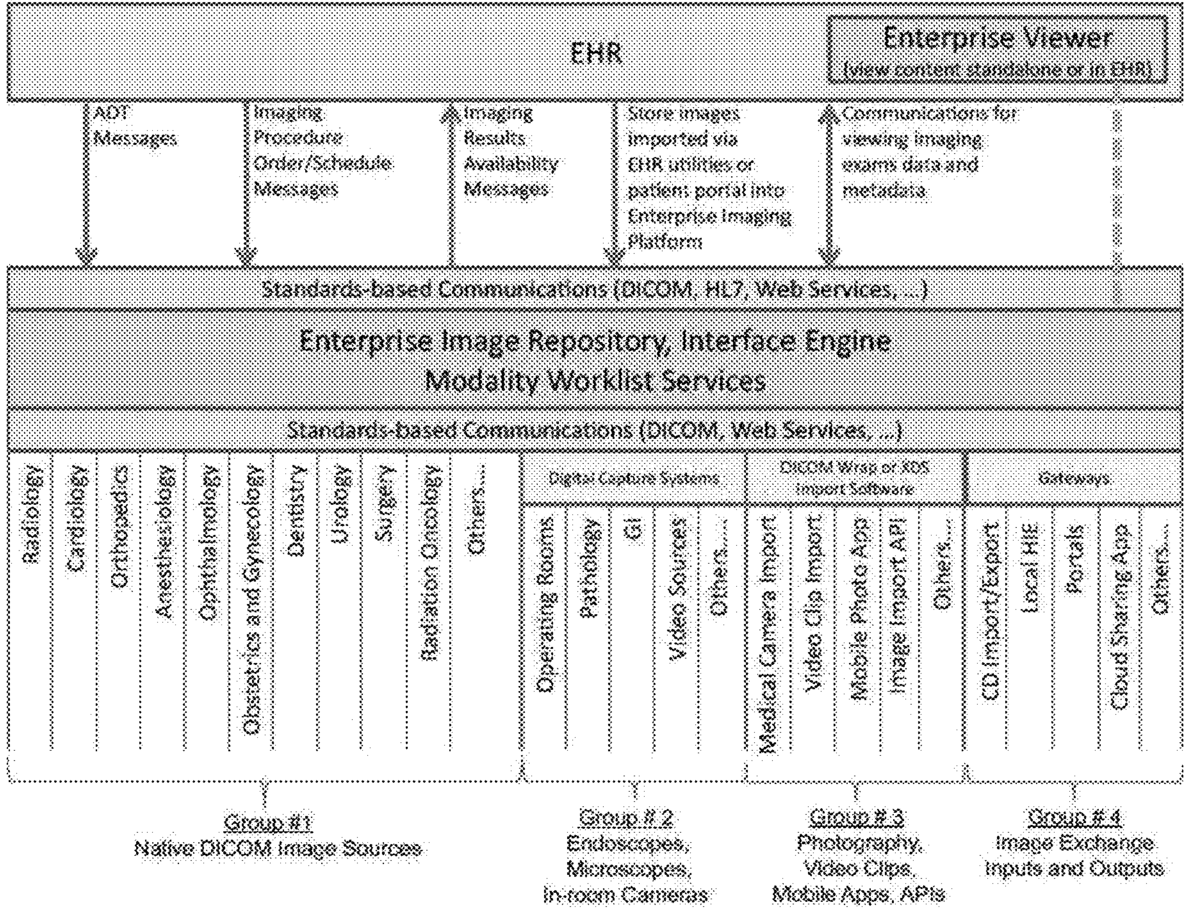
FIG. 35 depicts Cognitively-enriched Enterprise Imaging Repository Information Architecture.

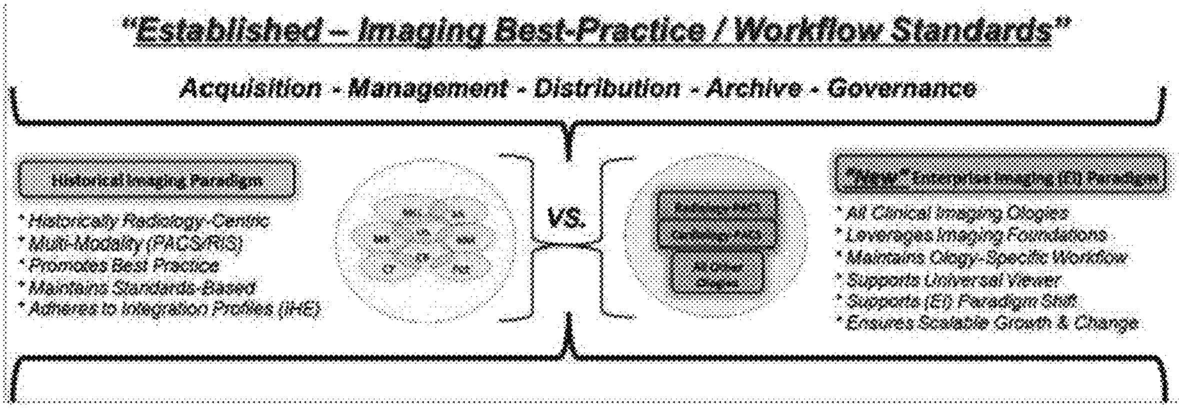
FIG. 36 depicts Cognitively-enriched Enterprise Imaging - Best Practices Workflows.

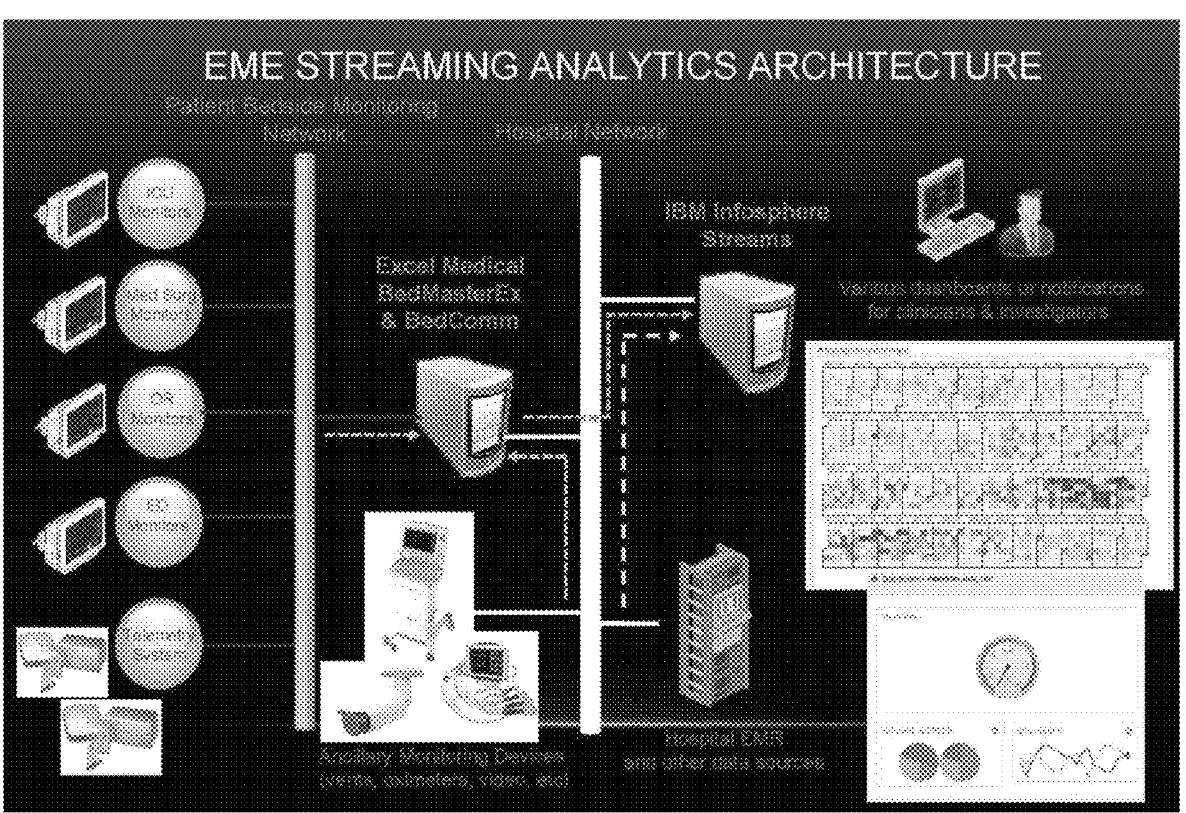
FIG. 37 depicts Streaming Analytics Architecture for Hospital-based Enterprise Imaging.

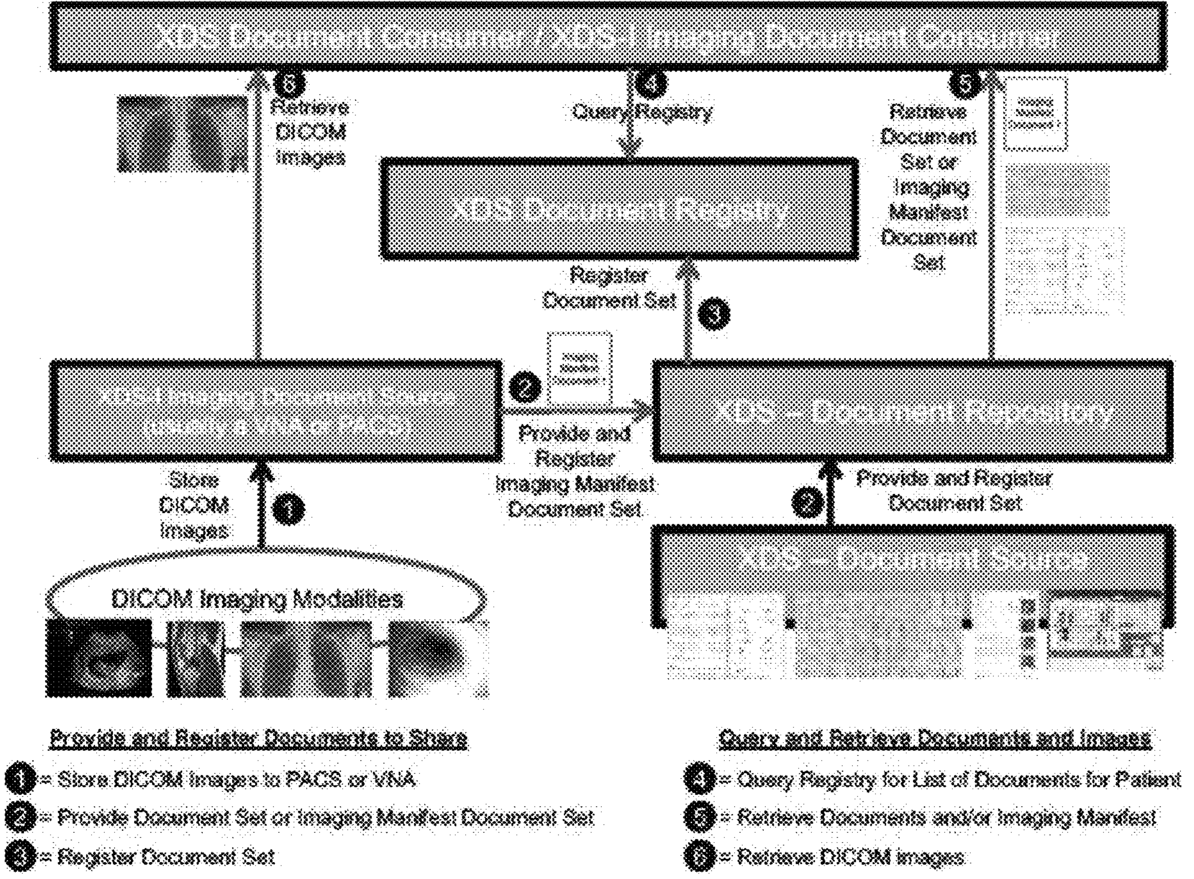
FIG. 38 depicts Imagery Document Exchange with Metadata Registries and an Enterprise Imaging Data Repository.

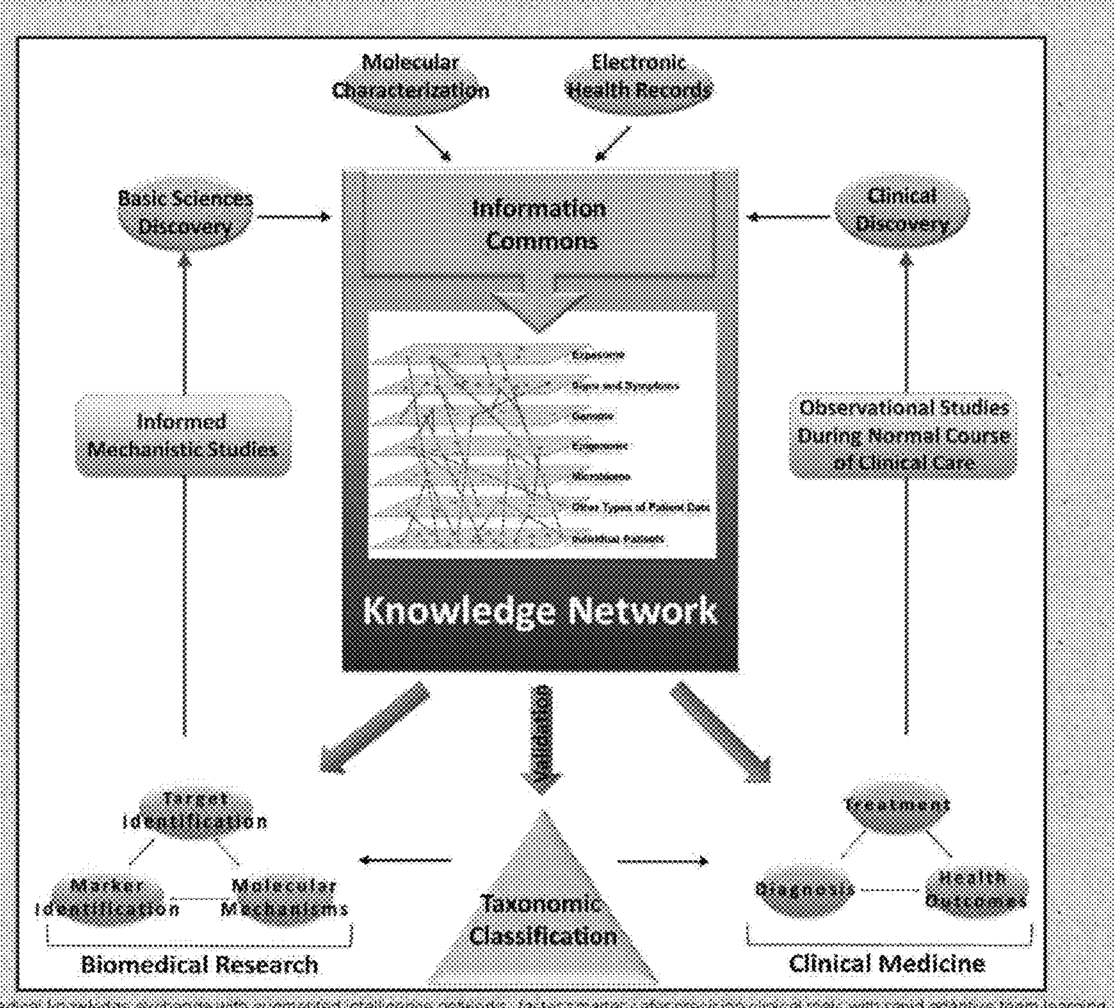
FIG. 39 depicts Biomedical Knowledge Exchange with Augmented Intelligence Networks.

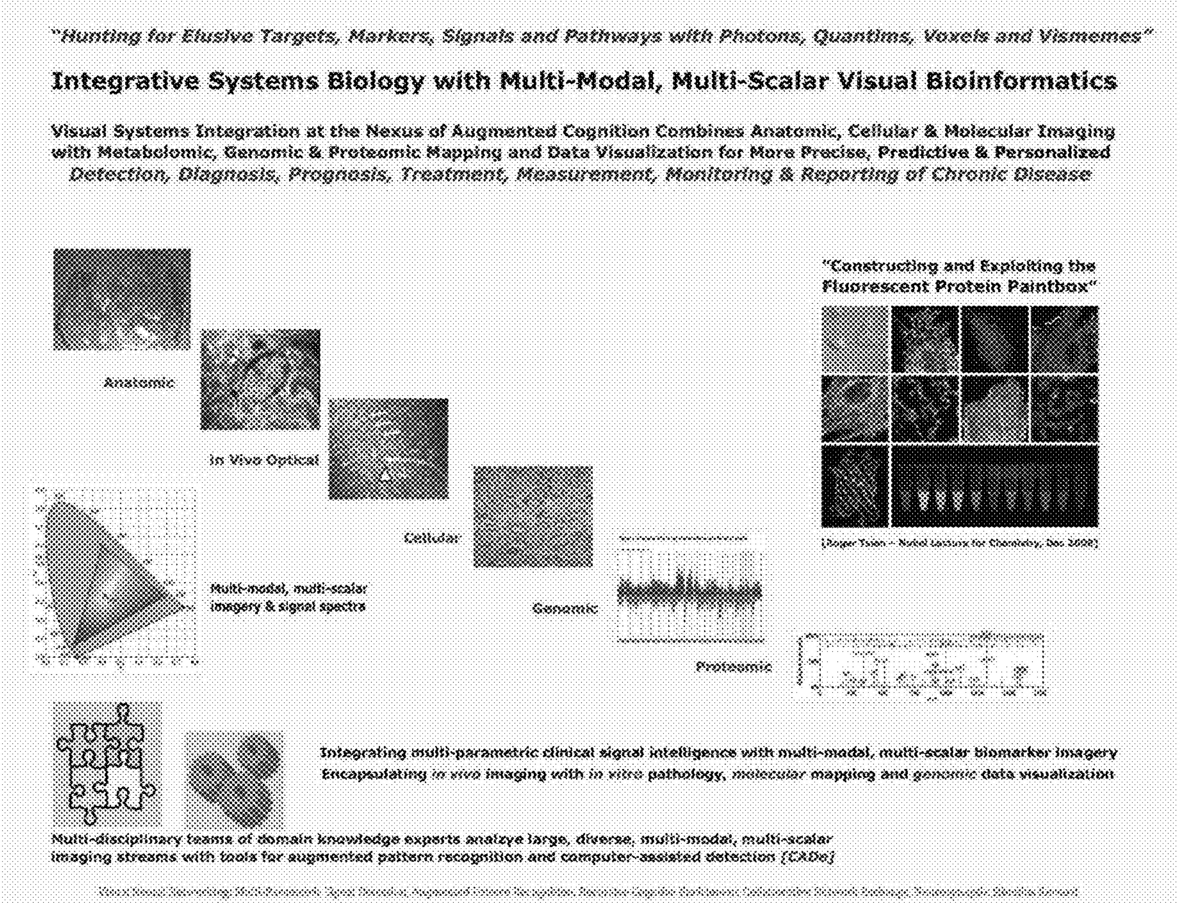
FIG. 40 depicts Integrative Systems Biology with Multimodal, Multi-Scalar Visual Bioinformatics.

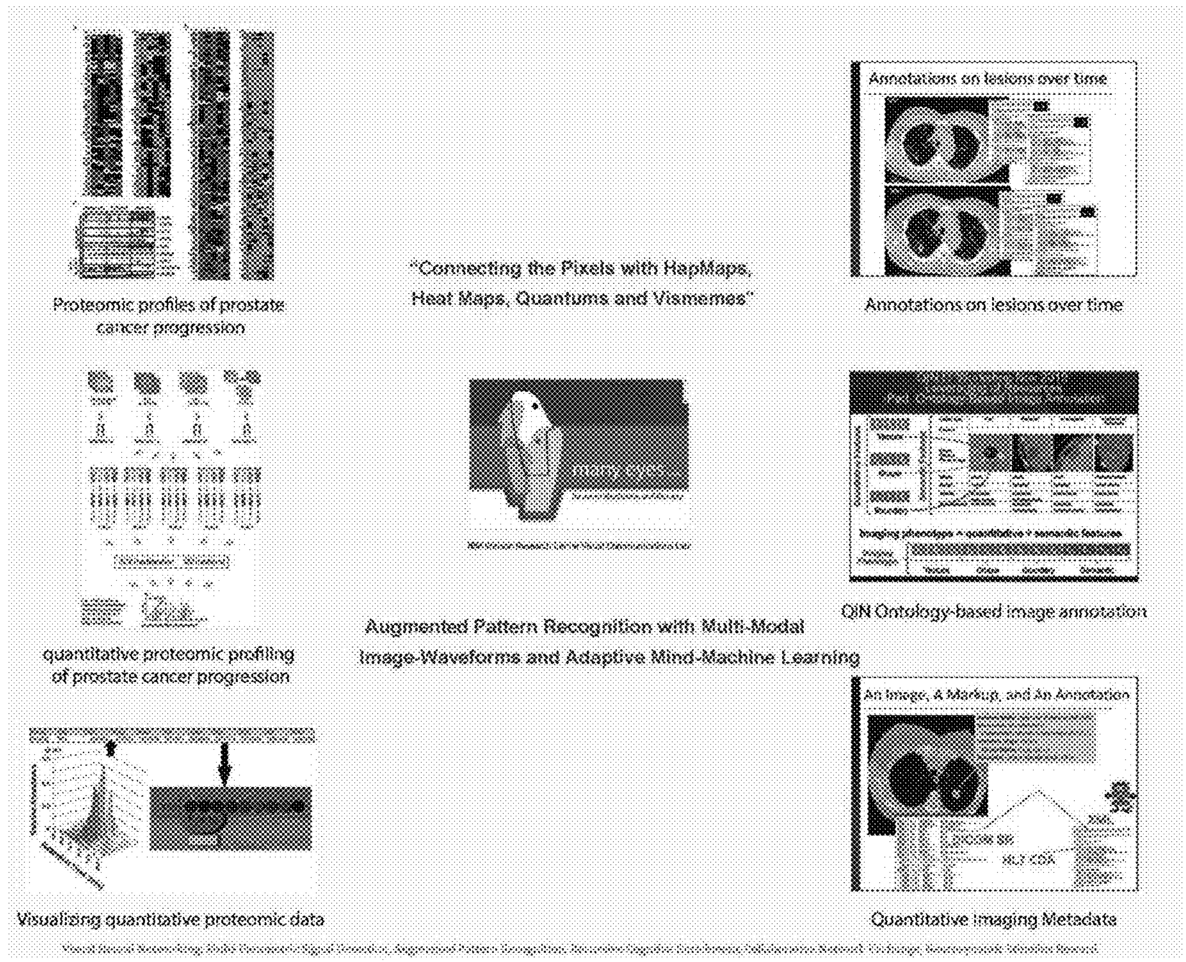
FIG. 41 depicts Augmented Pattern Recognition with Multimodal Radiogenomic Imagery and Adaptive Mind-Machine Learning.

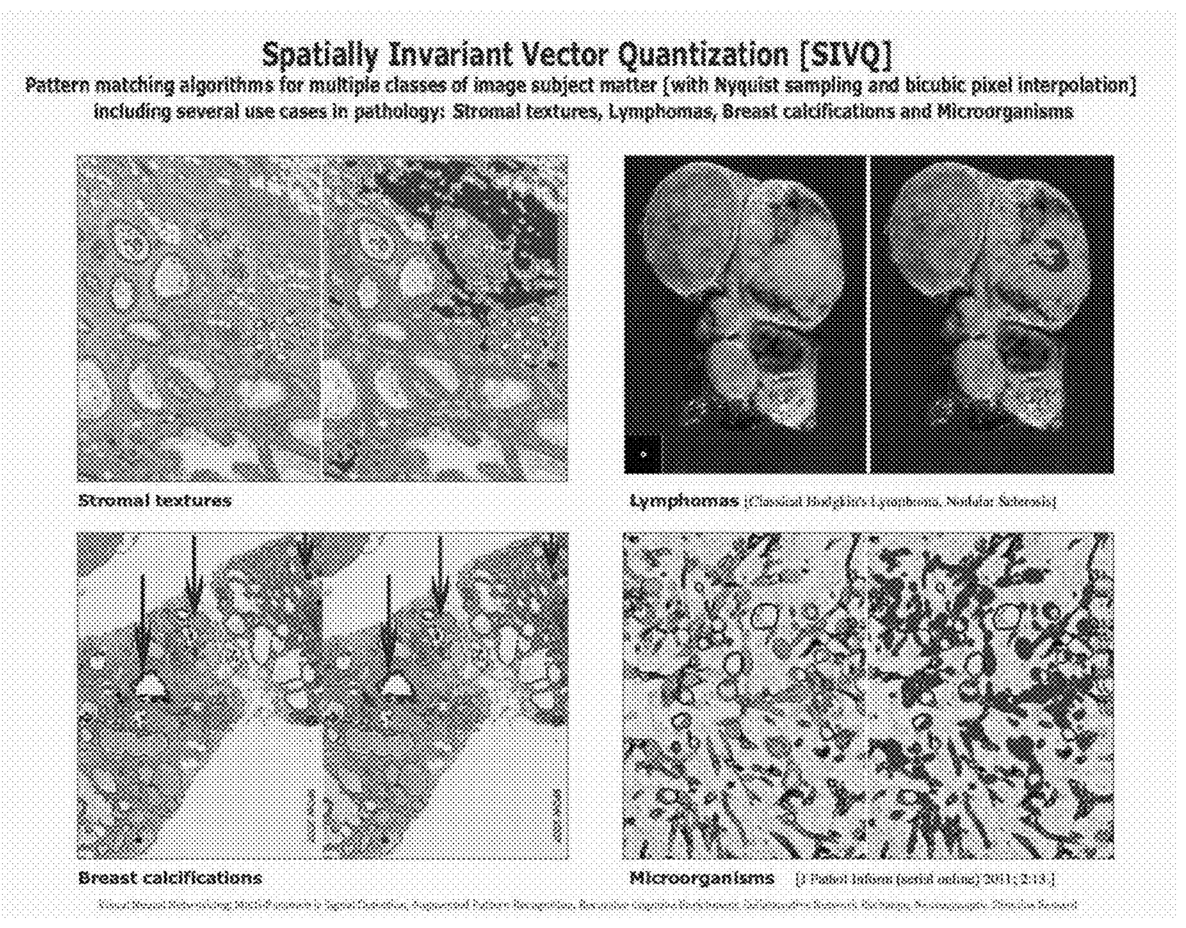
FIG. 42 depicts Pattern Matching Algorithms for Multiple Classes of Oncology Images.

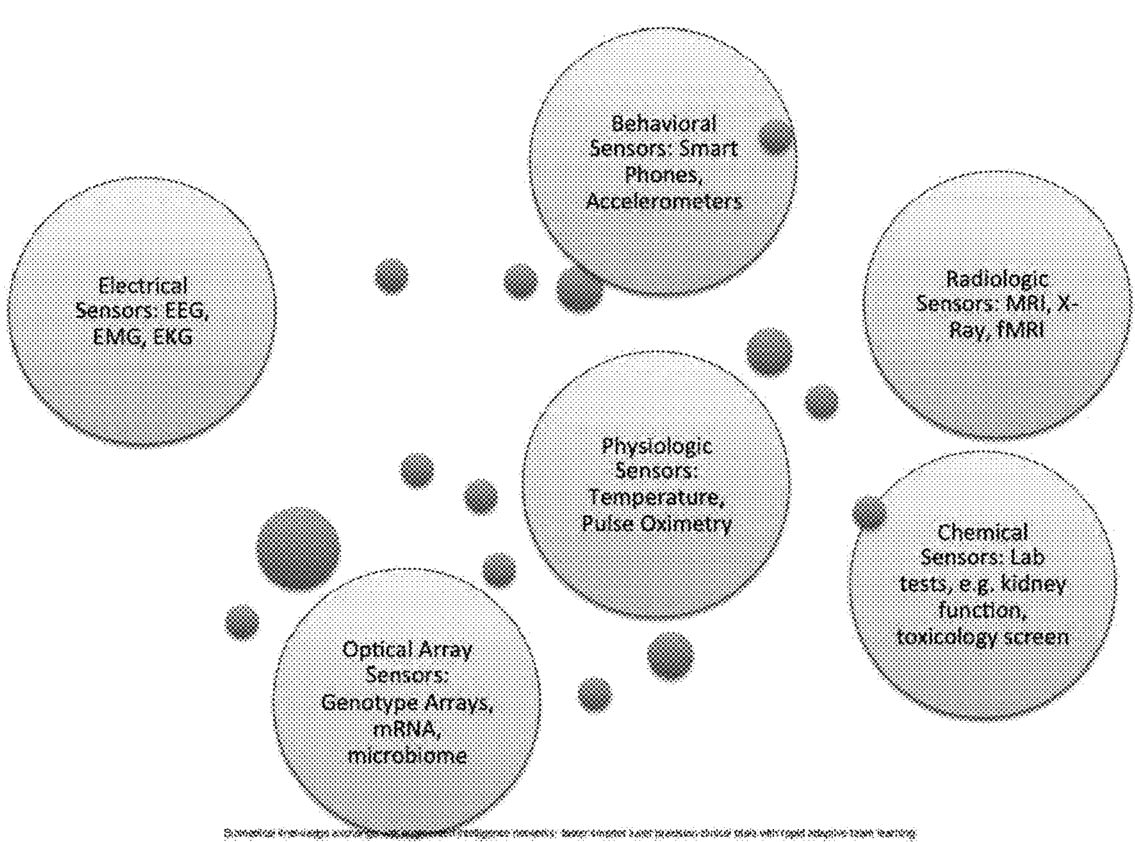
FIG. 43 depicts Early Disease Detection with Multimodal, Multi-Scalar Biomedical Sensors.

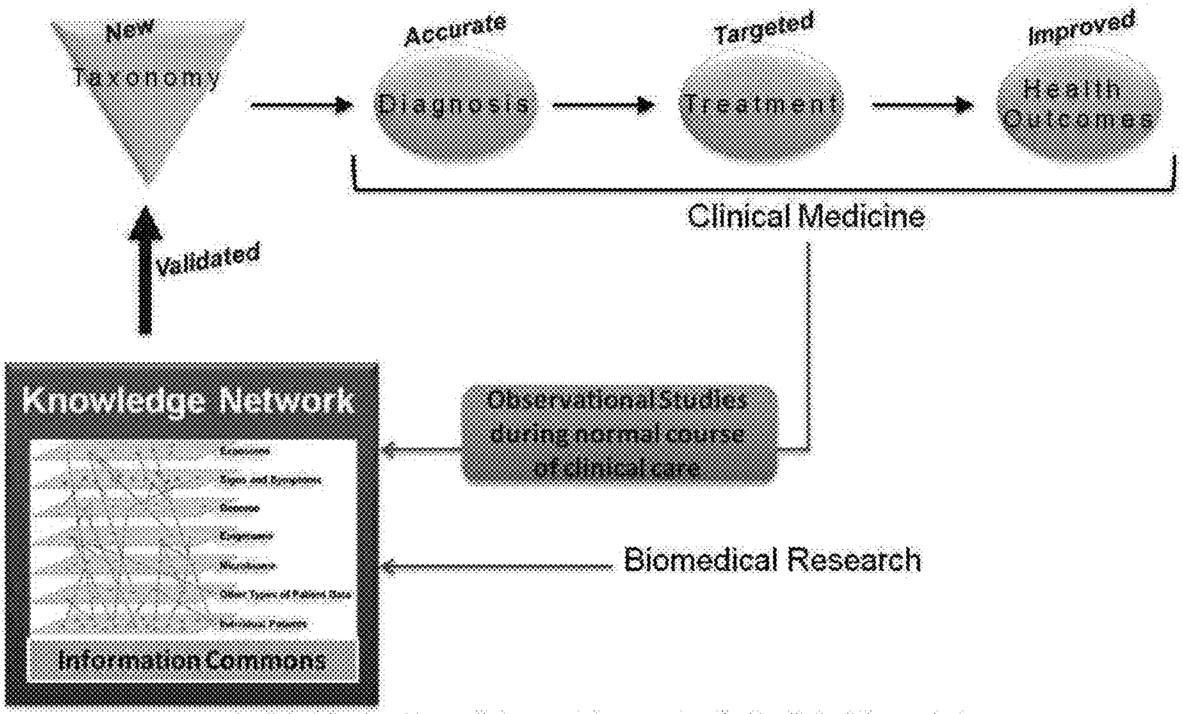
FIG. 44 depicts Clinical Knowledge Networks Integrating Biomedical Research with Clinical Medicine, "from Bench to Bedside".

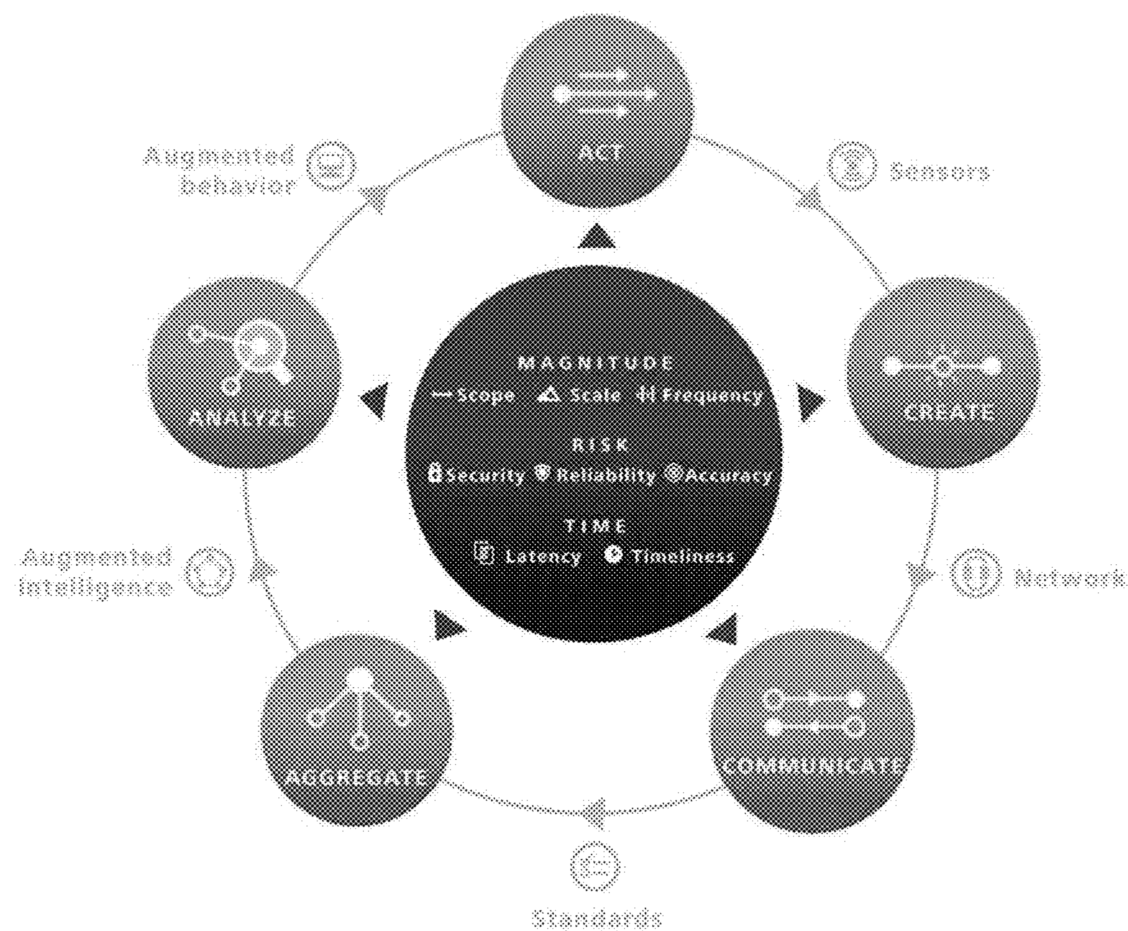
FIG. 45 depicts Value Drivers for Biomedical Knowledge Exchange with Augmented Intelligence Networks.

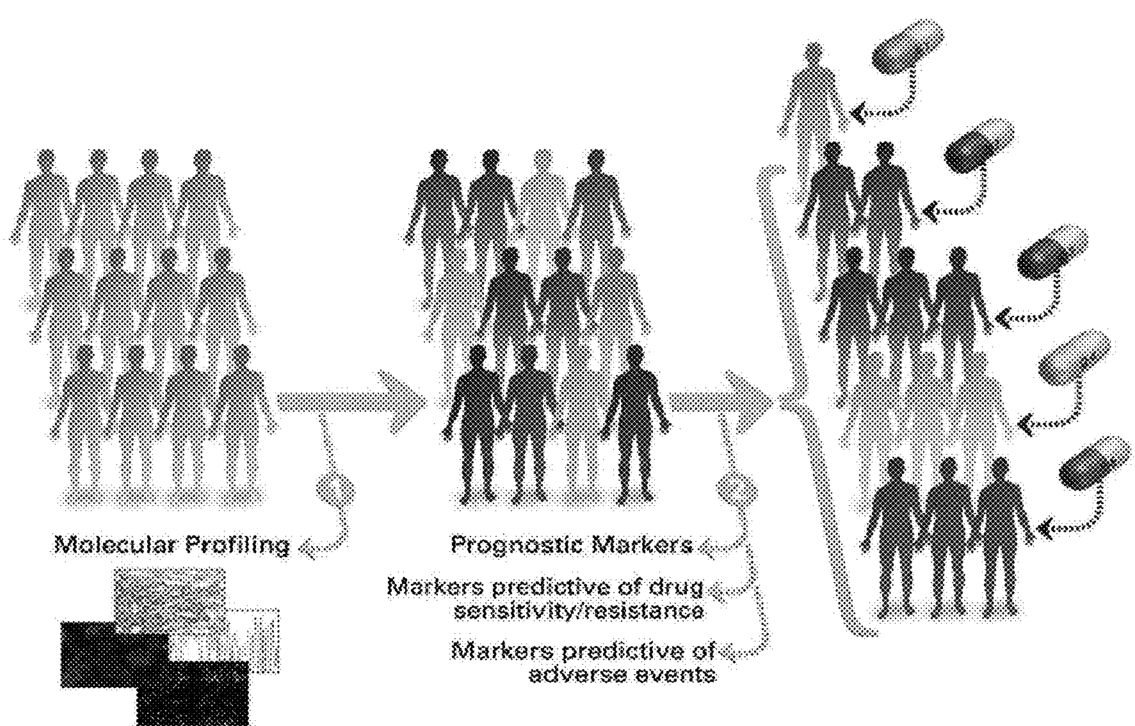
FIG. 46 depicts Molecular Profiling with Predictive Prognostic Markers for Precision Cancer Medicine.

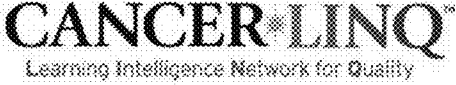
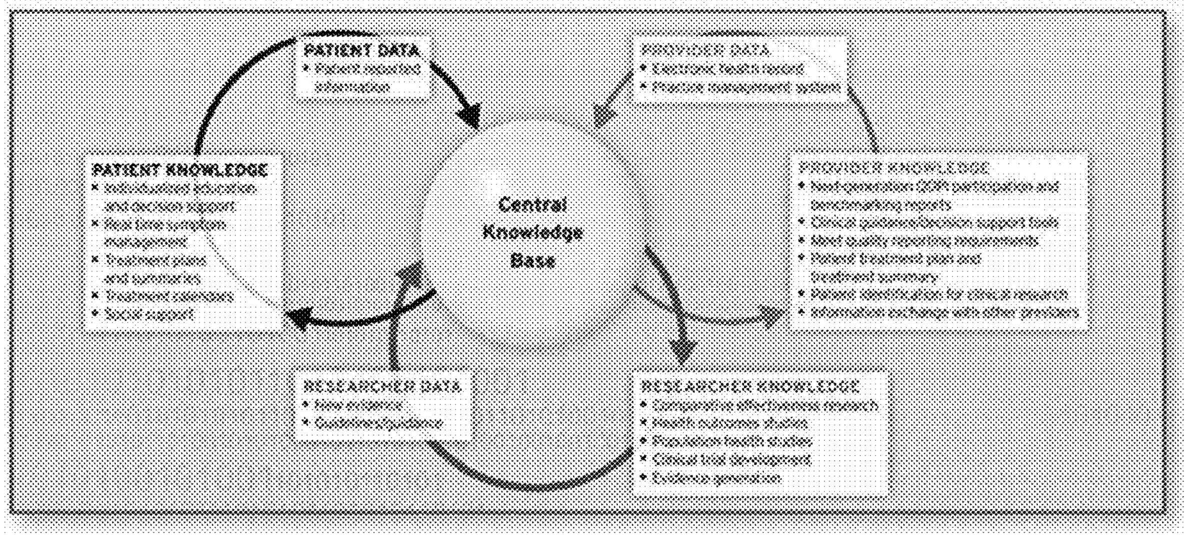
FIG. 47 depicts Cancer LINQ – A Learning Intelligence Network Connecting Patients, Providers and Researchers with Biomedical Data and Knowledge.

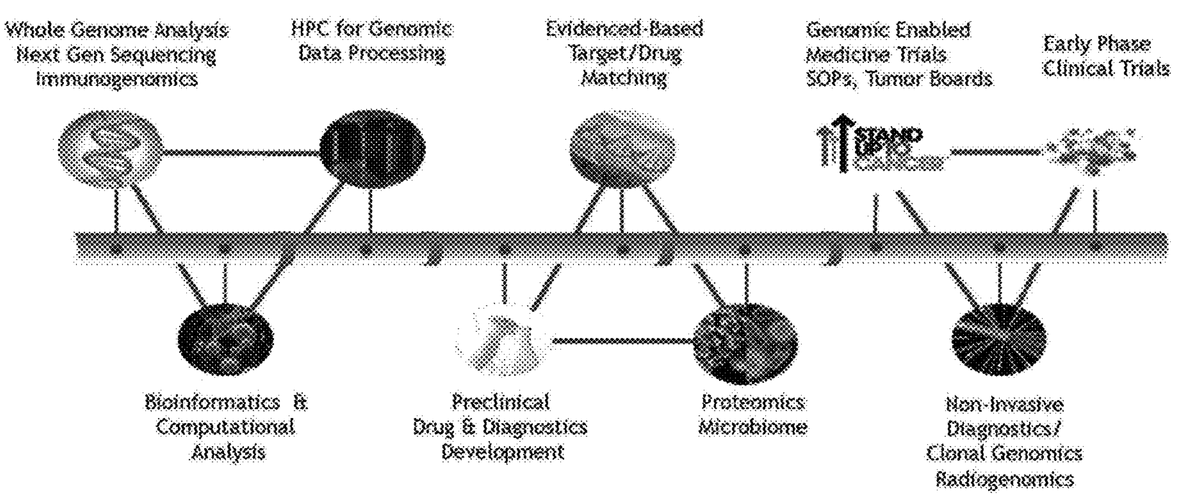
FIG. 48 depicts Connecting Collaborative Partnerships for Multiomic Data Analysis and Personalized Precision Medicine.

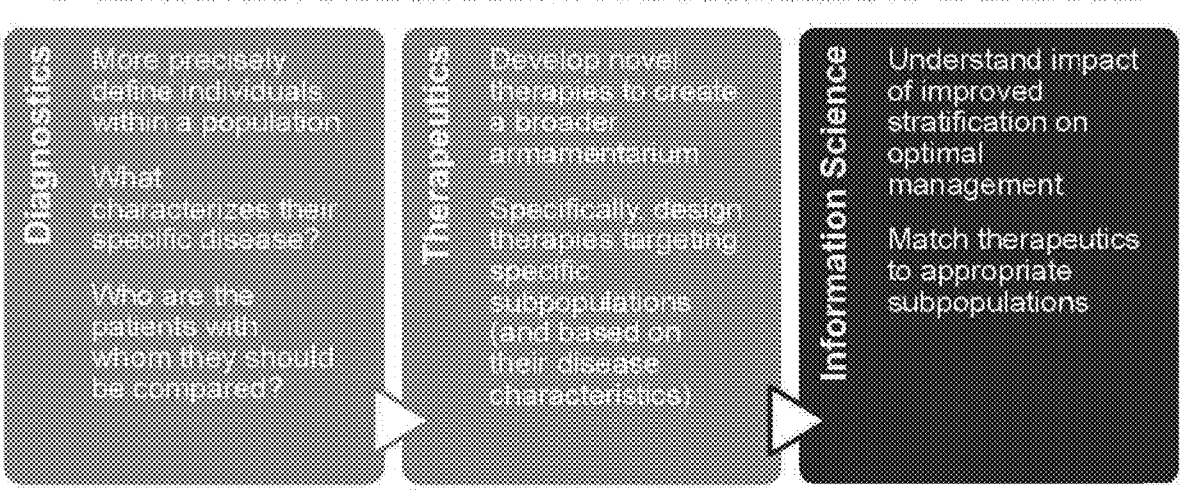
FIG. 49 depicts Precision Diagnostics and Precision Targeted Therapeutics Information Sciences for Personalized Precision Medicine.

Big Data is the Foundation of Precision Medicine

Today: Many disparate data types, streams...

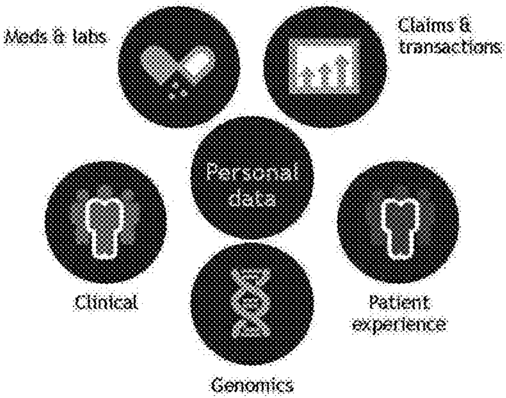

Future: Clinically Actionable Information

Leading to better decisions, improved patient experience, healthier population outcomes, and value-based care, higher quality at reduced costs

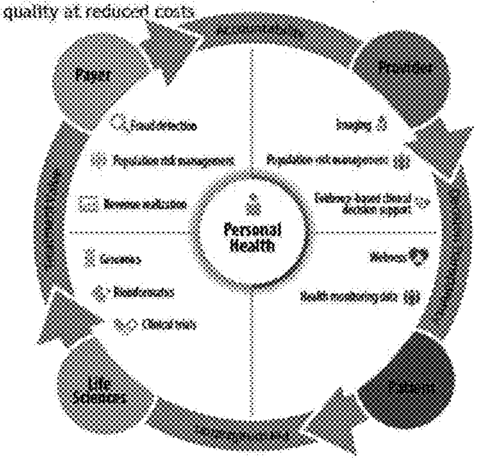

FIG. 50 depicts Clinically Actionable Information from Big Data as the foundation for Personalized Precision Medicine.

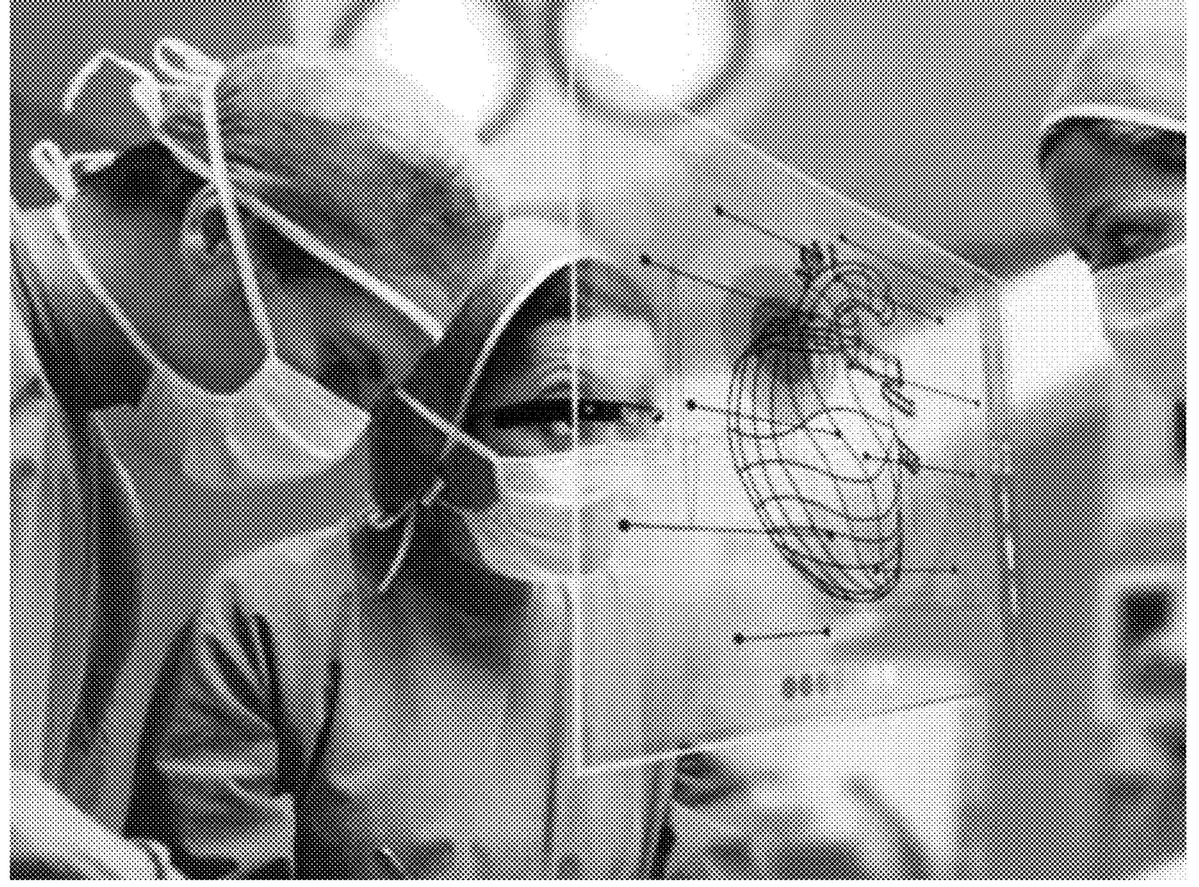
**FIG. 51 depicts *"See One. Do One. Teach One."* Surgical Telementoring, Teamwork and Training with Augmented Generative Intelligence.**

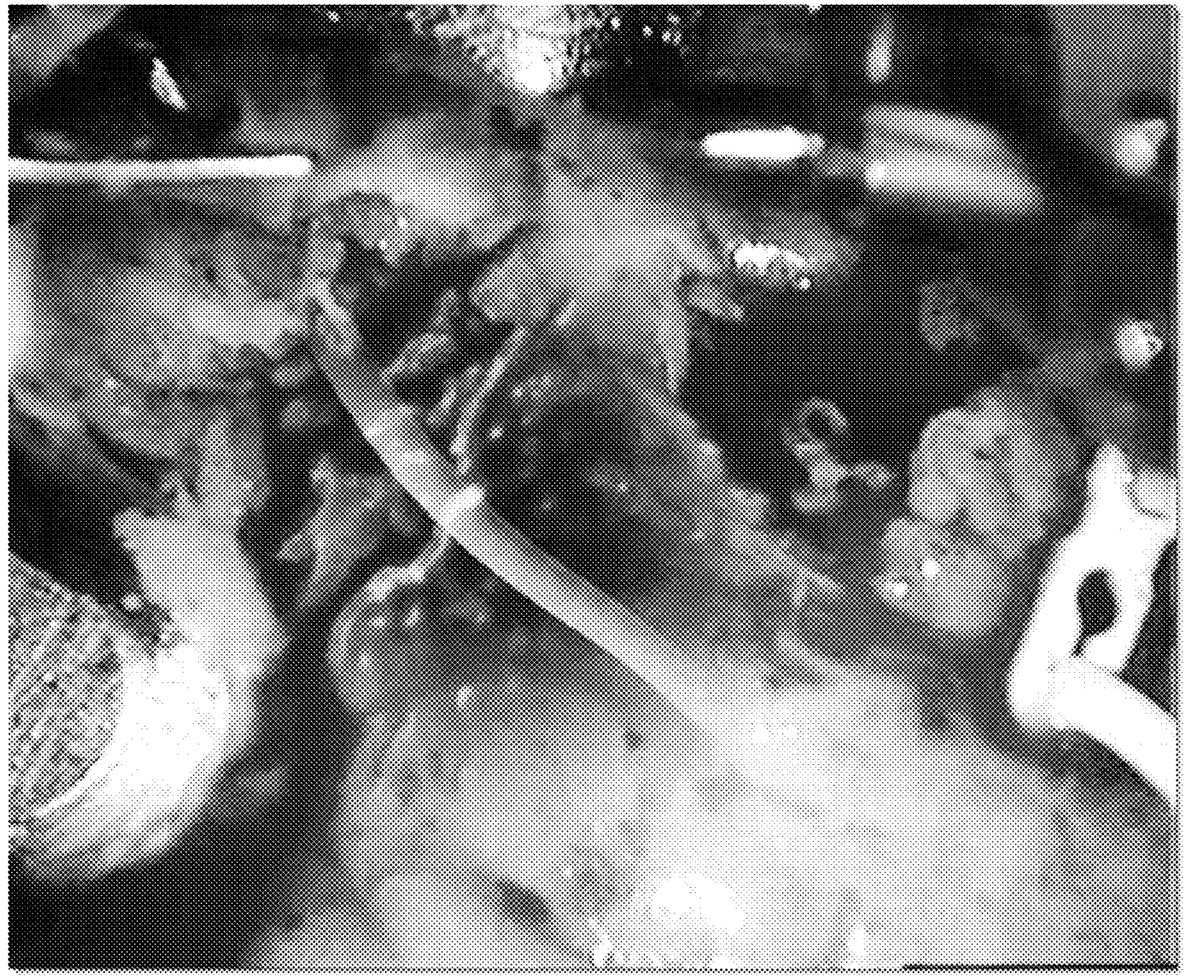
FIG. 52 depicts Imagery Guided Computer Assisted Surgery.

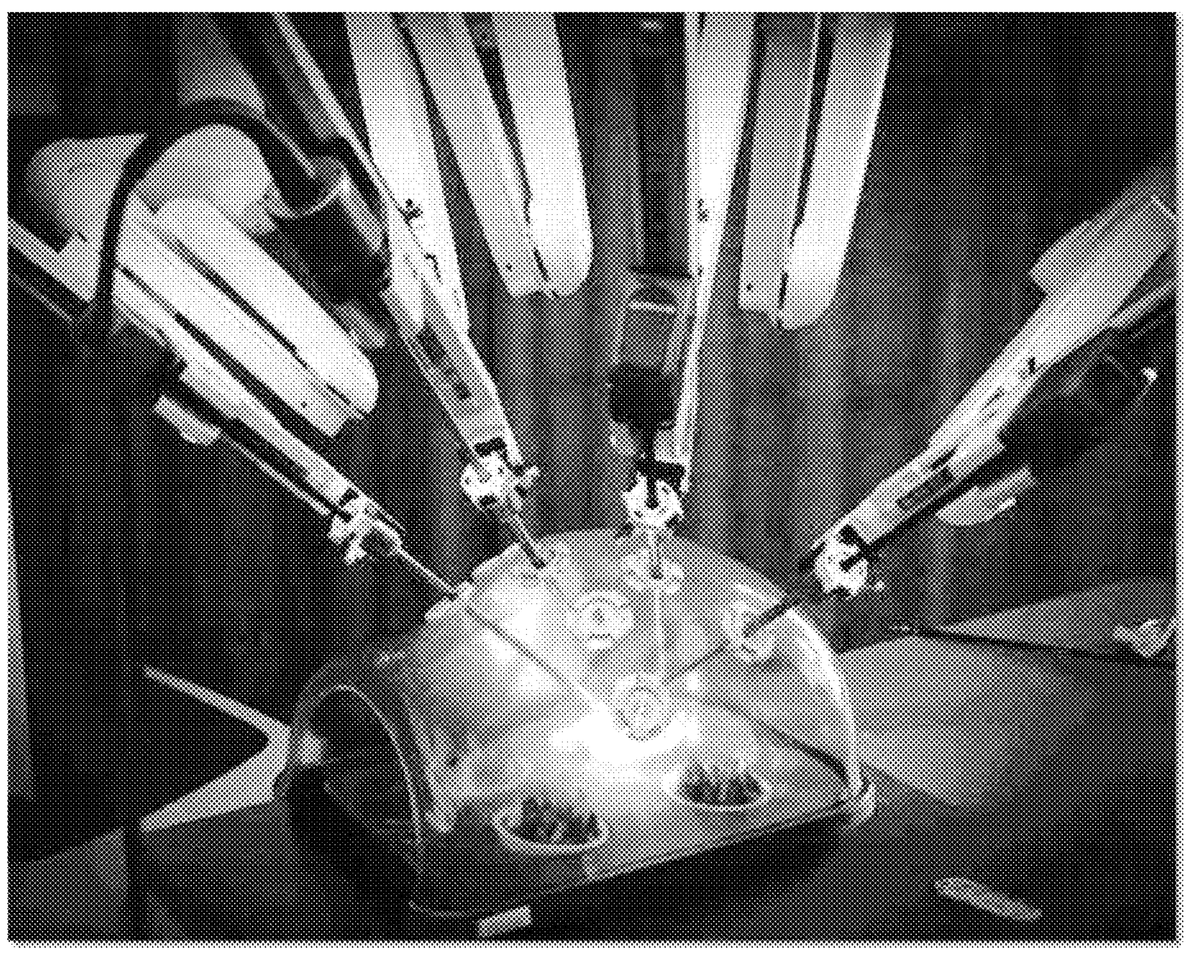
FIG. 53 depicts Informatics-Enriched Robotic Assisted Surgery.

FIG. 54 depicts Streaming Augmented Reality Surgical Instruction.

- Augmented reality visualizations
- Surgical guidance
- Simulation of surgical navigation
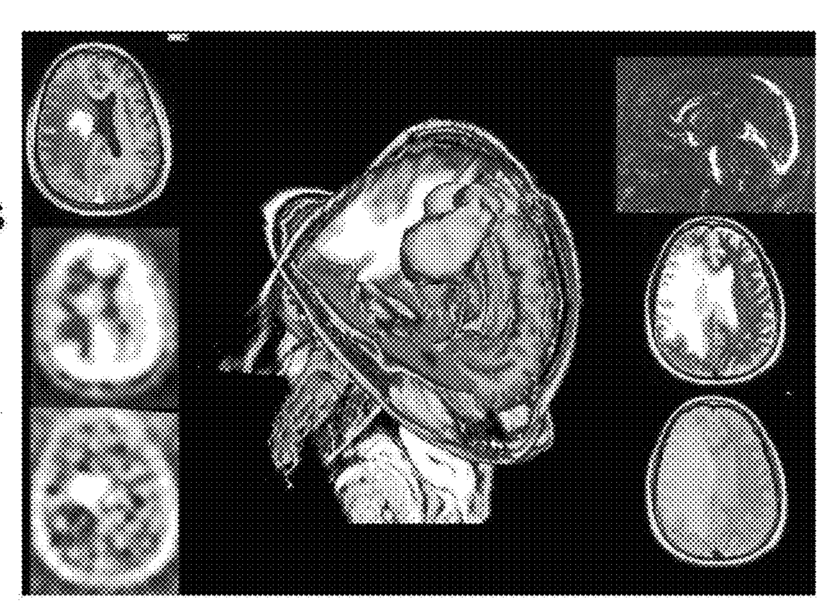
FIG. 55 depicts Surgical Navigation and Guidance with 3D Data Visualization and Streaming Augmented Reality.

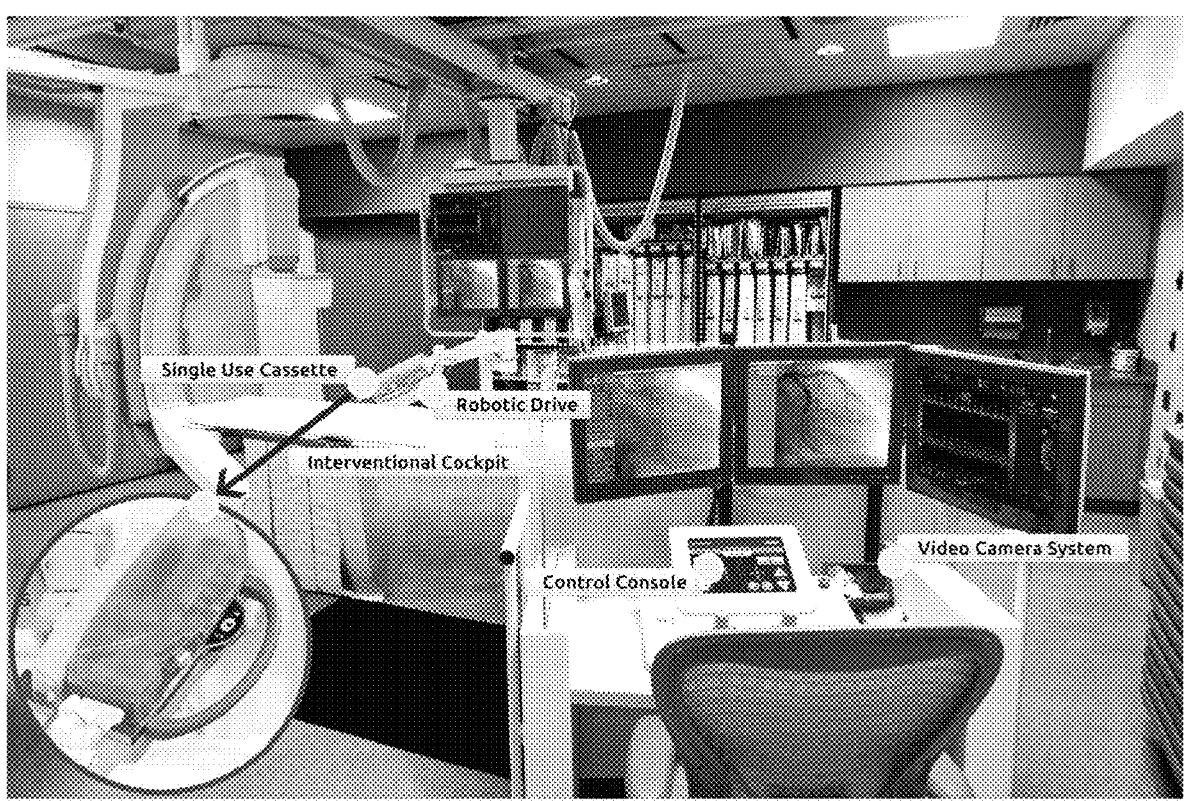
FIG. 56 depicts Visualizing the Surgical Site for Robotic Assisted Intervention.

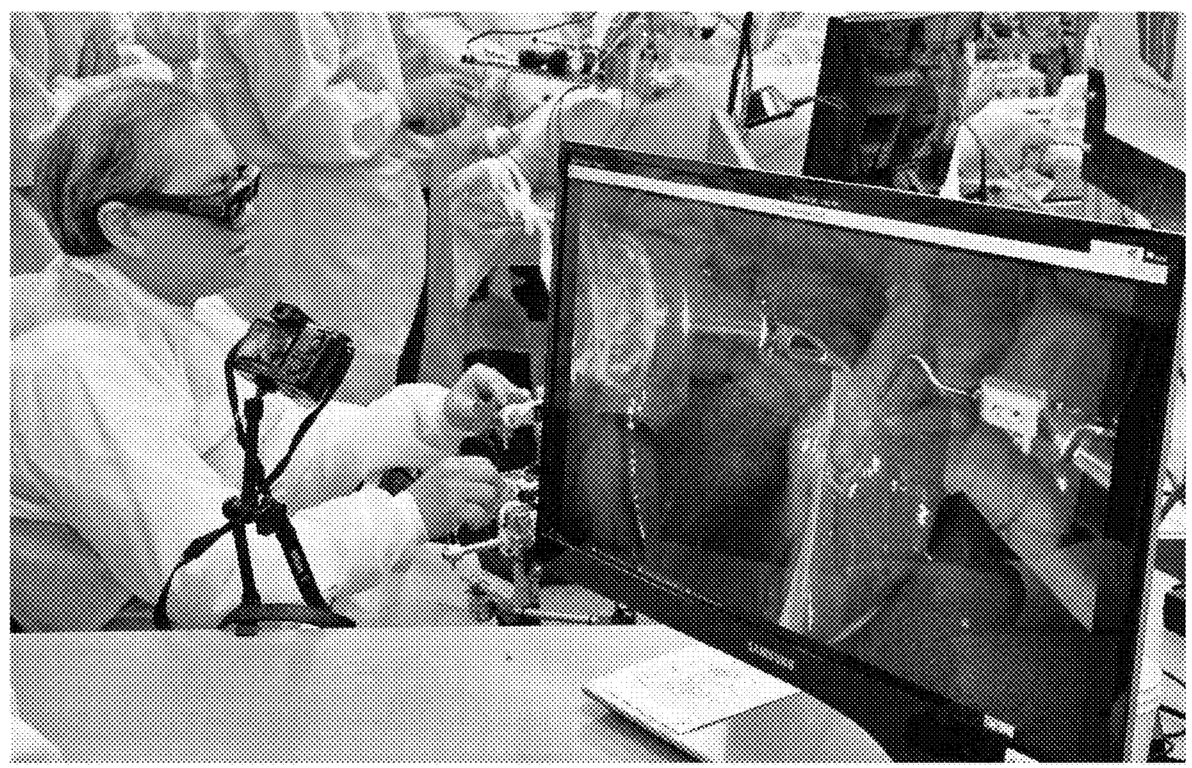
FIG. 57 depicts an Imagery Guided Minimally Invasive Surgical Robotic System.

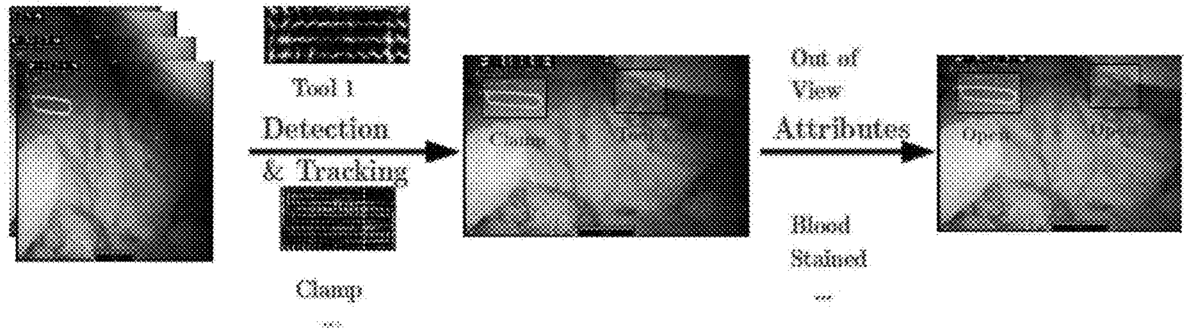

Figure 1: System pipeline of proposed algorithm

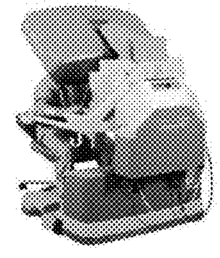

Figure 2: Intuitive Surgical's da Vinci SKILLS Simulator Si (dVSS-Si)

In Equation 2, the probabilities at each time step $P(x_t = 1|y_t)$ are directly given by probabilistic SVM classifier. This in effect weights the classification decision by not only the current observation but also by the decision in previous frames.

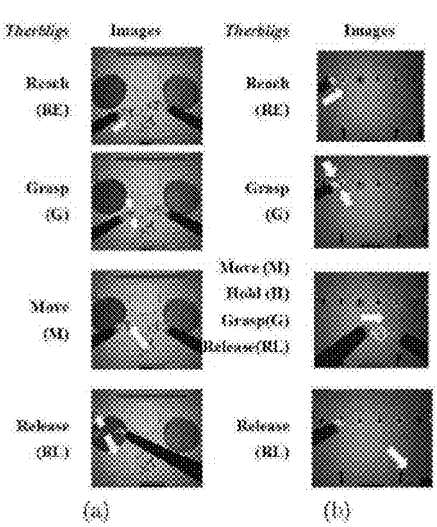

FIG. 58 depicts Visio-Spatial Algorithms Development for Precision Guided Surgery.

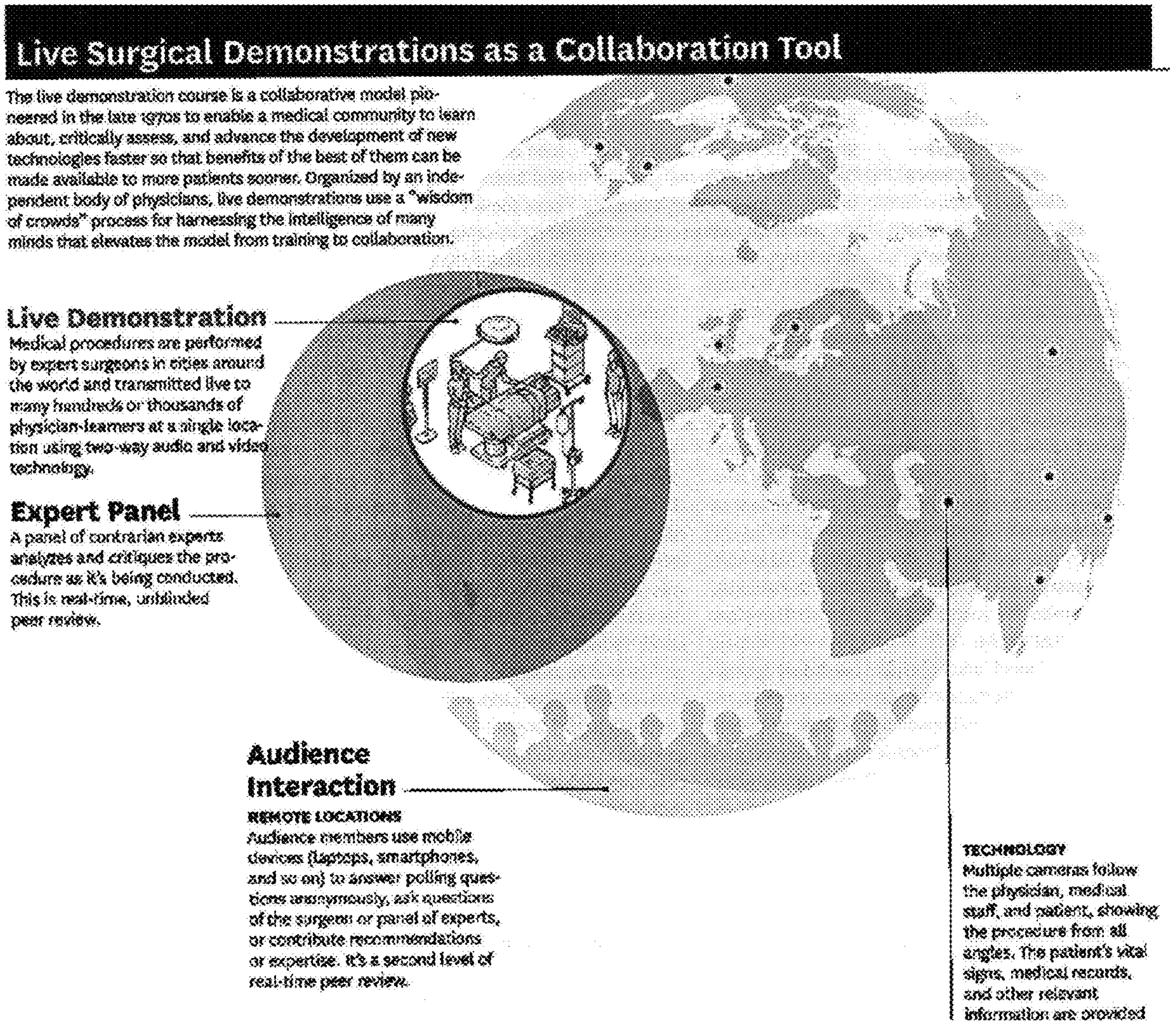
FIG. 59 depicts Live Surgical Demonstration with Expert Panels as Collaborative Teaching Tools.

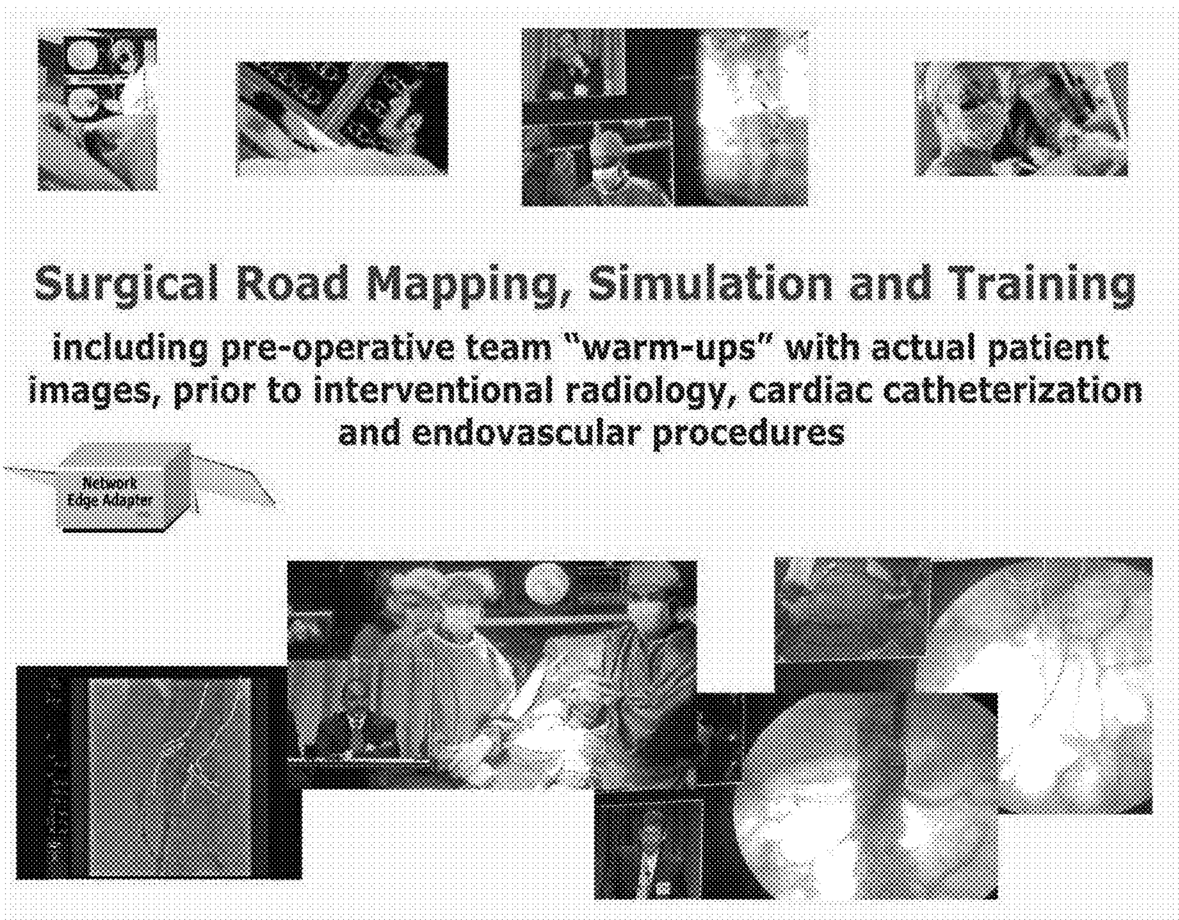
FIG. 60 depicts Live Remote Intraoperative Telesurgical Consultation during Aneurysm Repair.

Complex procedures don't need to be described, but can in fact be demonstrated.
Highlights:
- Realistic MIS instruments to demonstrate complex surgical procedures.
- The ability to cut, retract and suture a *live video feed.*
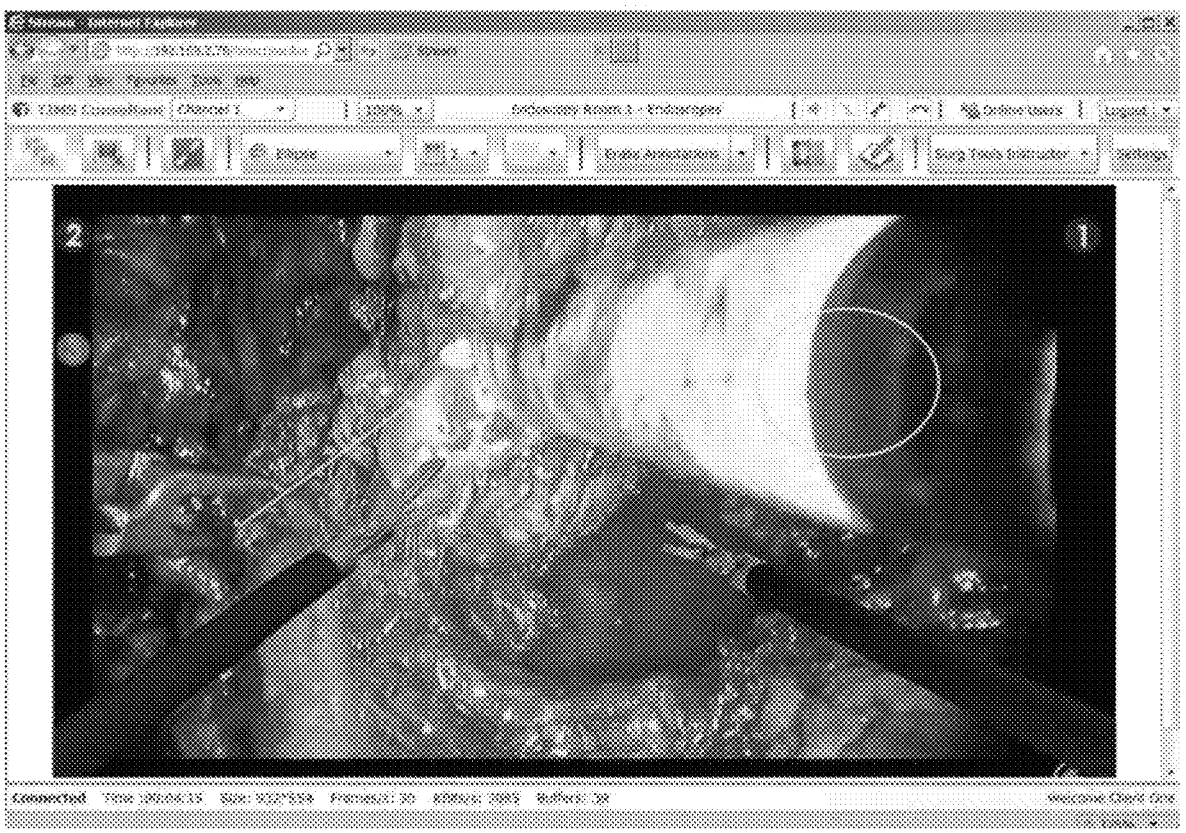
FIG. 61 depicts Live Remote Surgical Telementoring, Teamwork & Training with Interactive Streaming Video and Multisensory Augmented Reality.

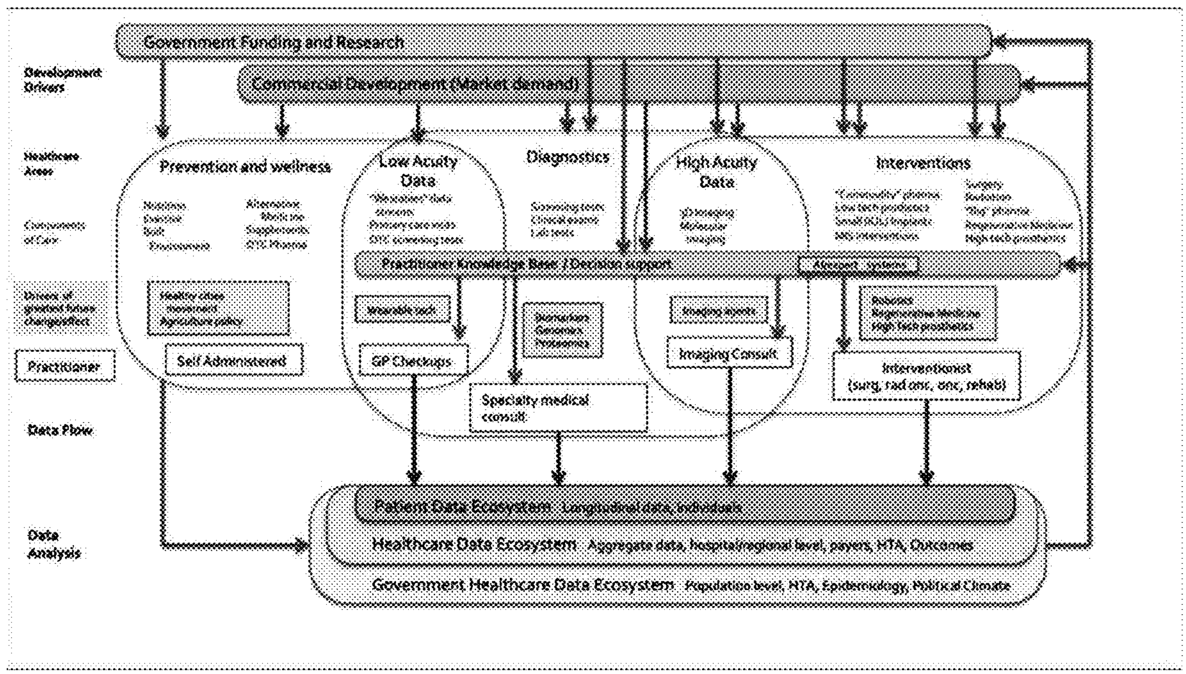
FIG. 62 depicts interconnected Ecosystems of the Future for Informatics-Enriched Imagery Guided Interventions.

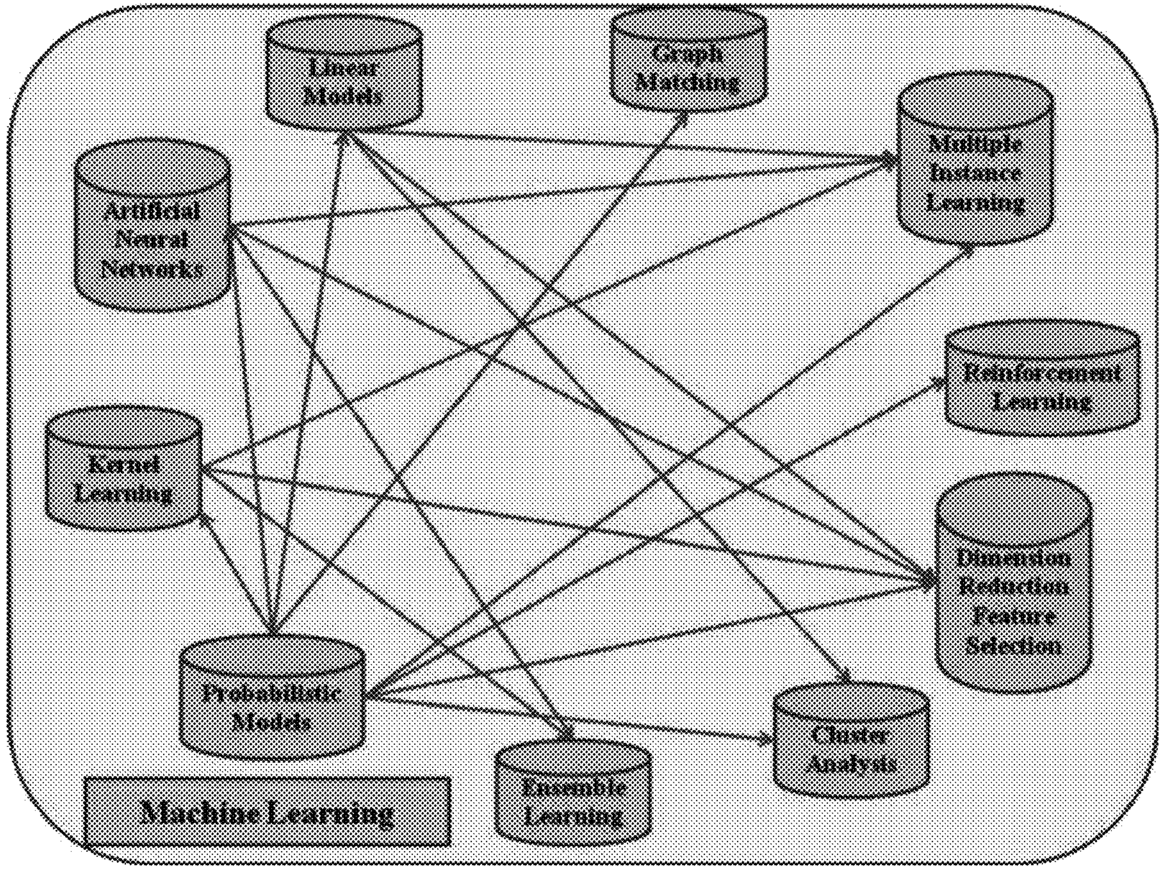
FIG. 63 depicts various techniques for Machine Learning with Medical Imaging.

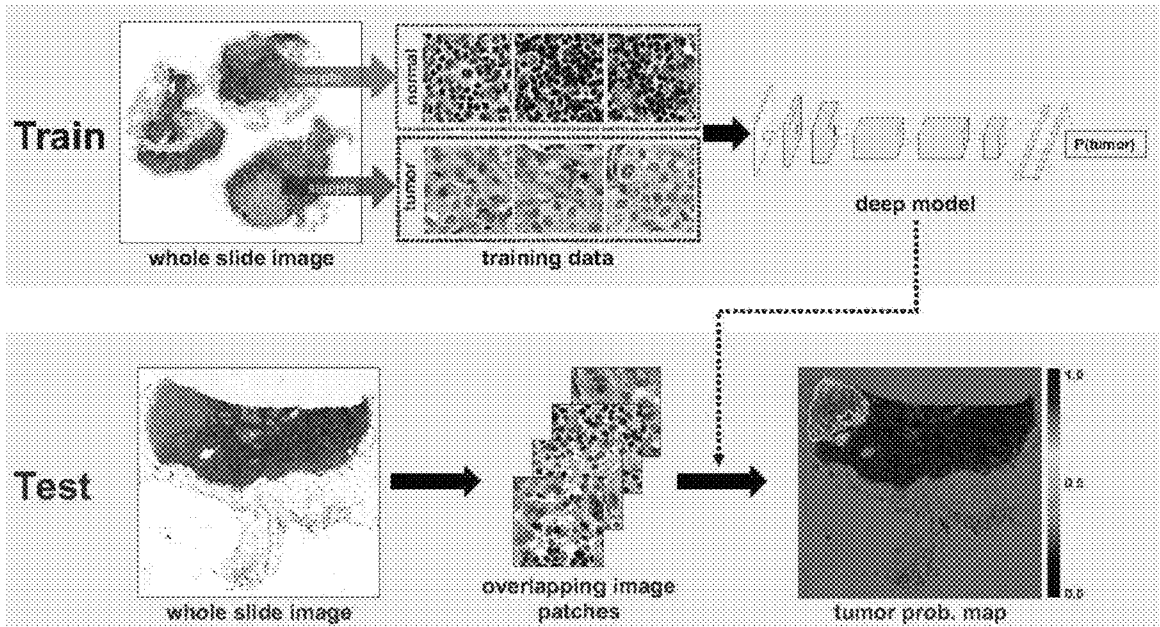
FIG. 64 depicts a Framework for Cancer Metastasis Detection with Deep Learning Models and Whole Slide Imaging.

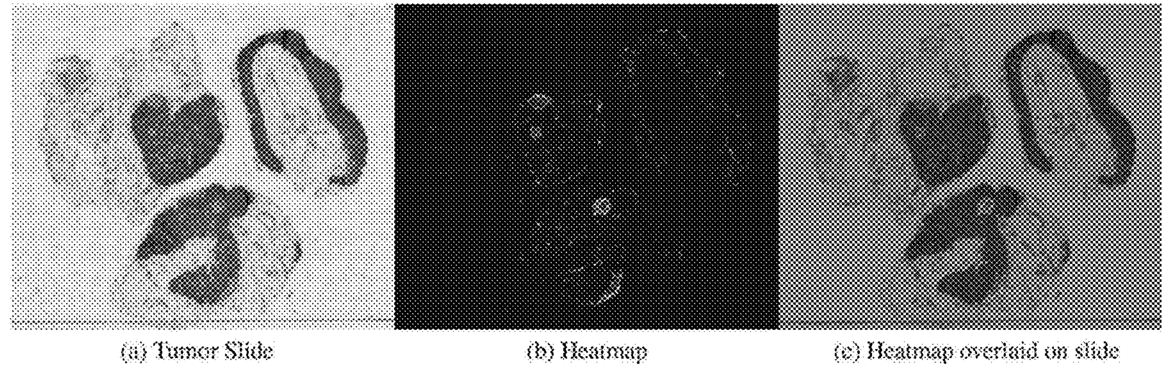
FIG. 65 depicts visualization of Tumor Region Detection with Slide/Heat Map Overlays.

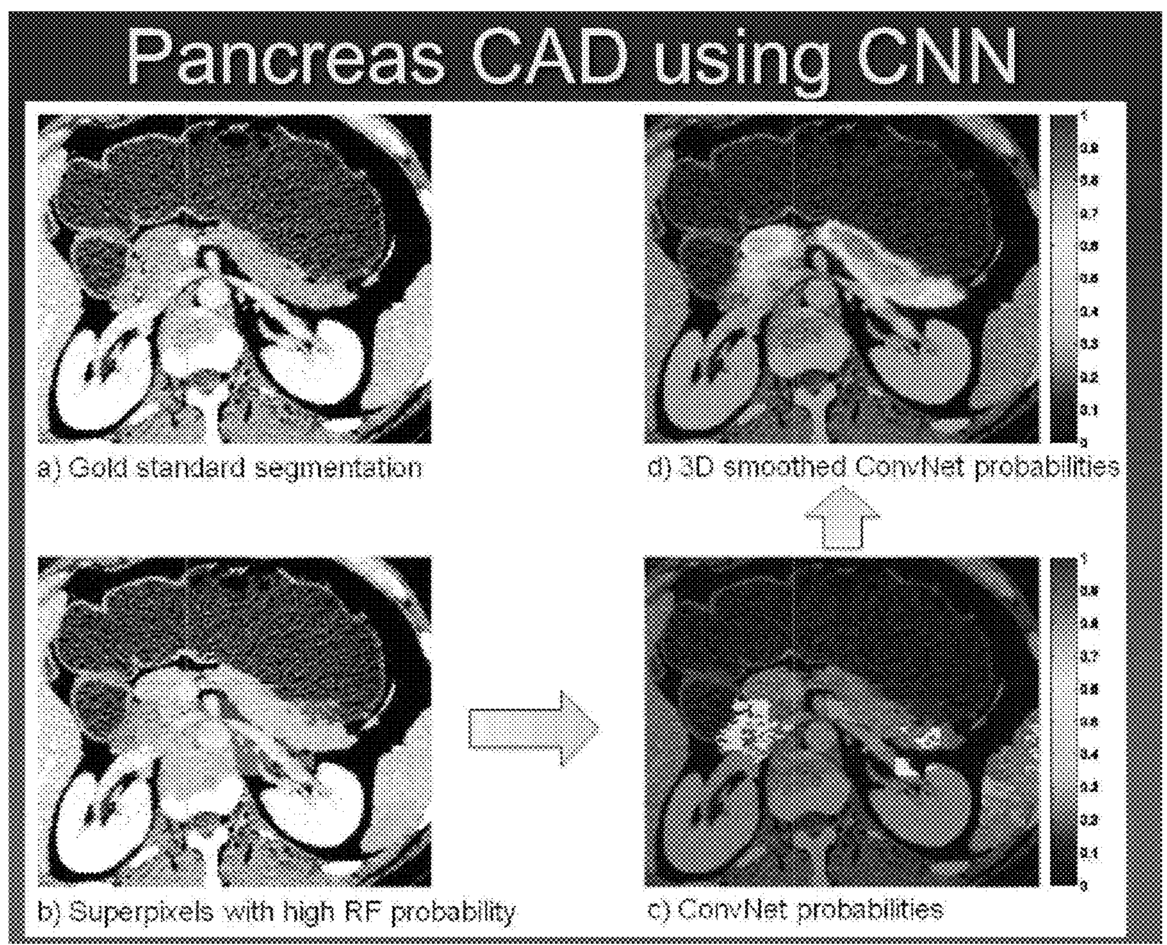
FIG. 66 depicts Pancreatic Cancer Computer Assisted Detection with Convolutional Neural Networks.

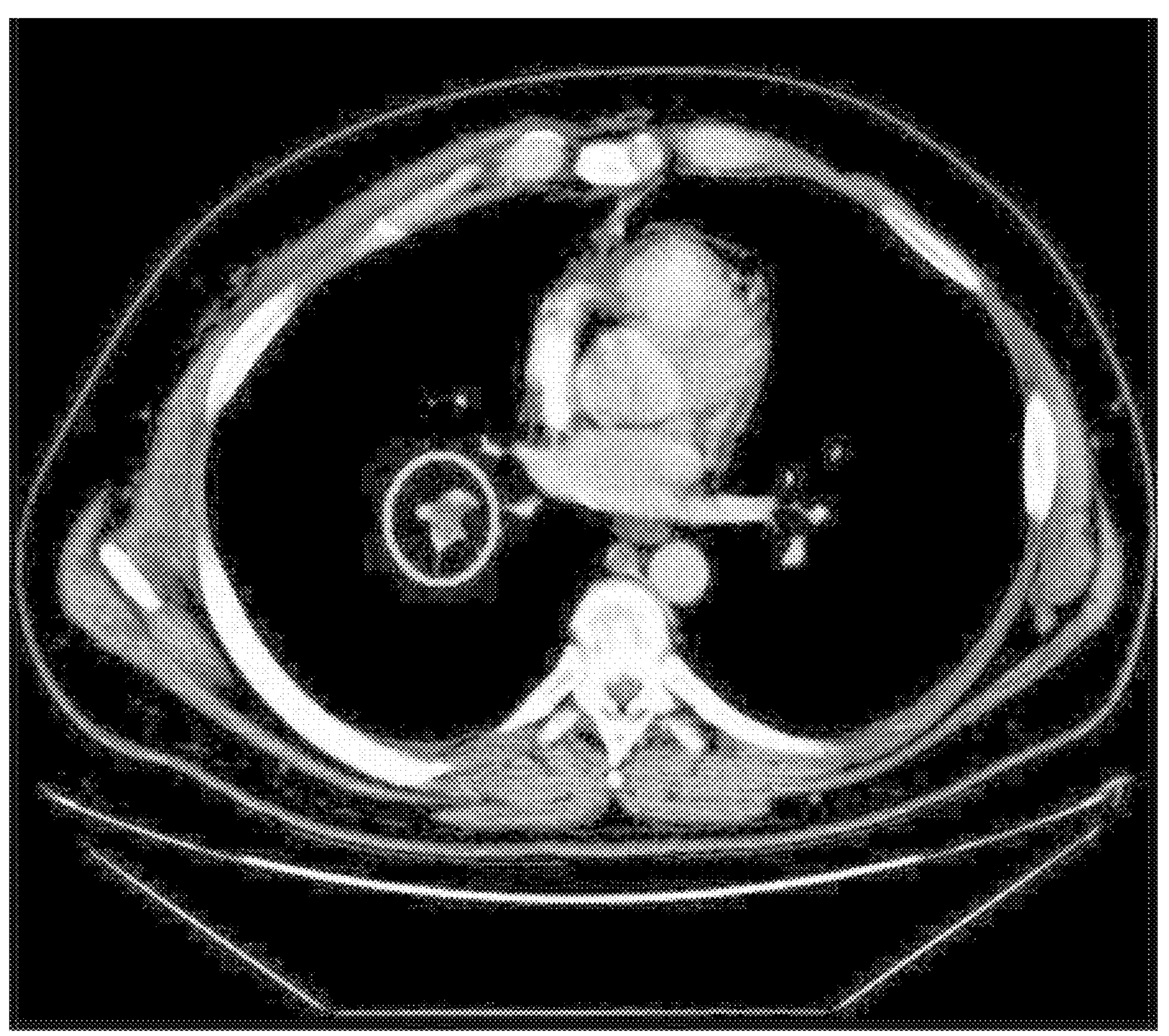
FIG. 67 depicts Pulmonary Embolism Identification with Machine Learning.

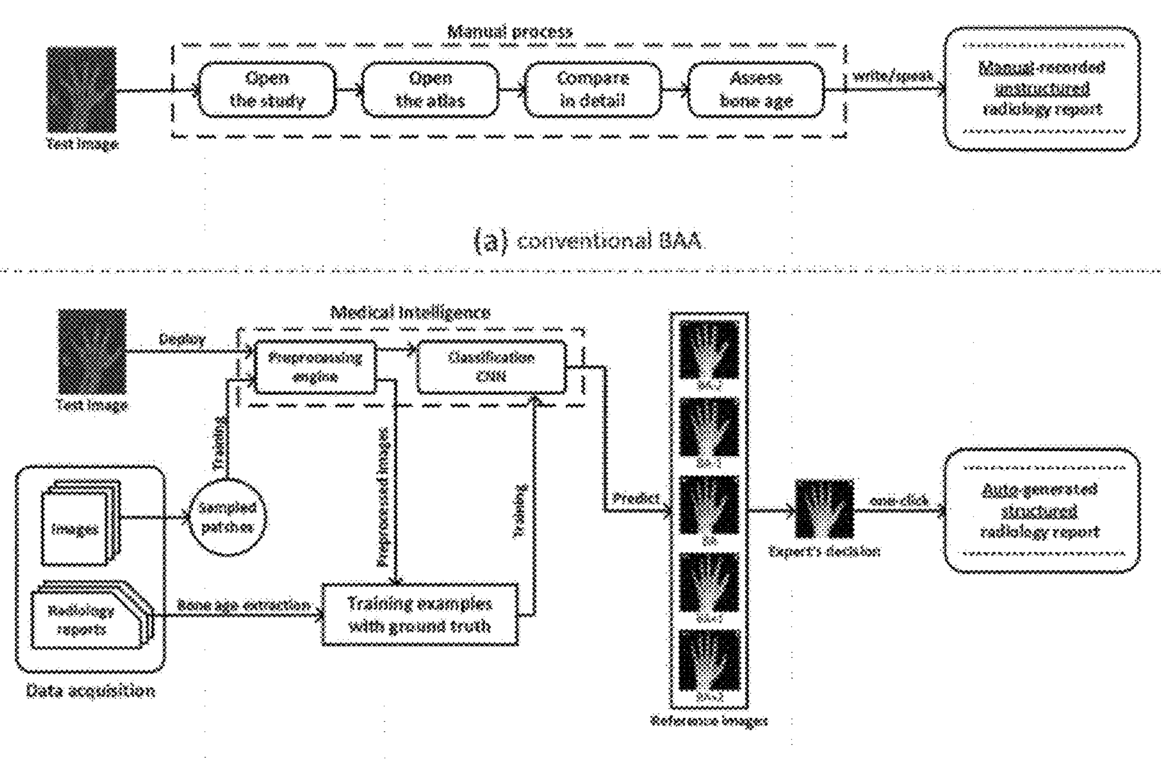
FIG. 68 depicts Bone Age Assessment with Deep Learning Systems.

Research Issue – Video-Based Attributes Labeling and Semantic Identification

A high level flow chart of our video-based framework for semantic identification (extended from our tracking implementation) is shown in the following figure.

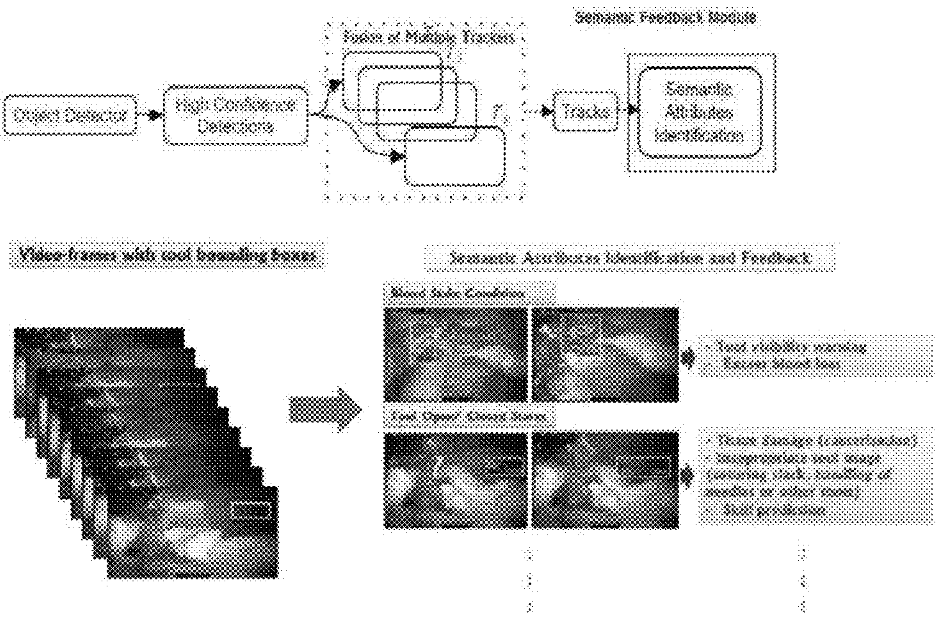

Video-Based Attributes Labeling and Semantic Identification Framework

By training and optimizing the classifiers using our training and test data (a subset of ground truth annotations), we were able to obtain promising results for attribute identification and semantic feedback compared to the state-of-art method. Though this framework can be generalized for arbitrary set of attributes, we focus our efforts for specifically two attributes tool open and close as well as blood stained/ non-stained condition of tool. The results obtained are summarized FIG. 69 depicts Video-based Attributes Labeling and Semantic Identification.

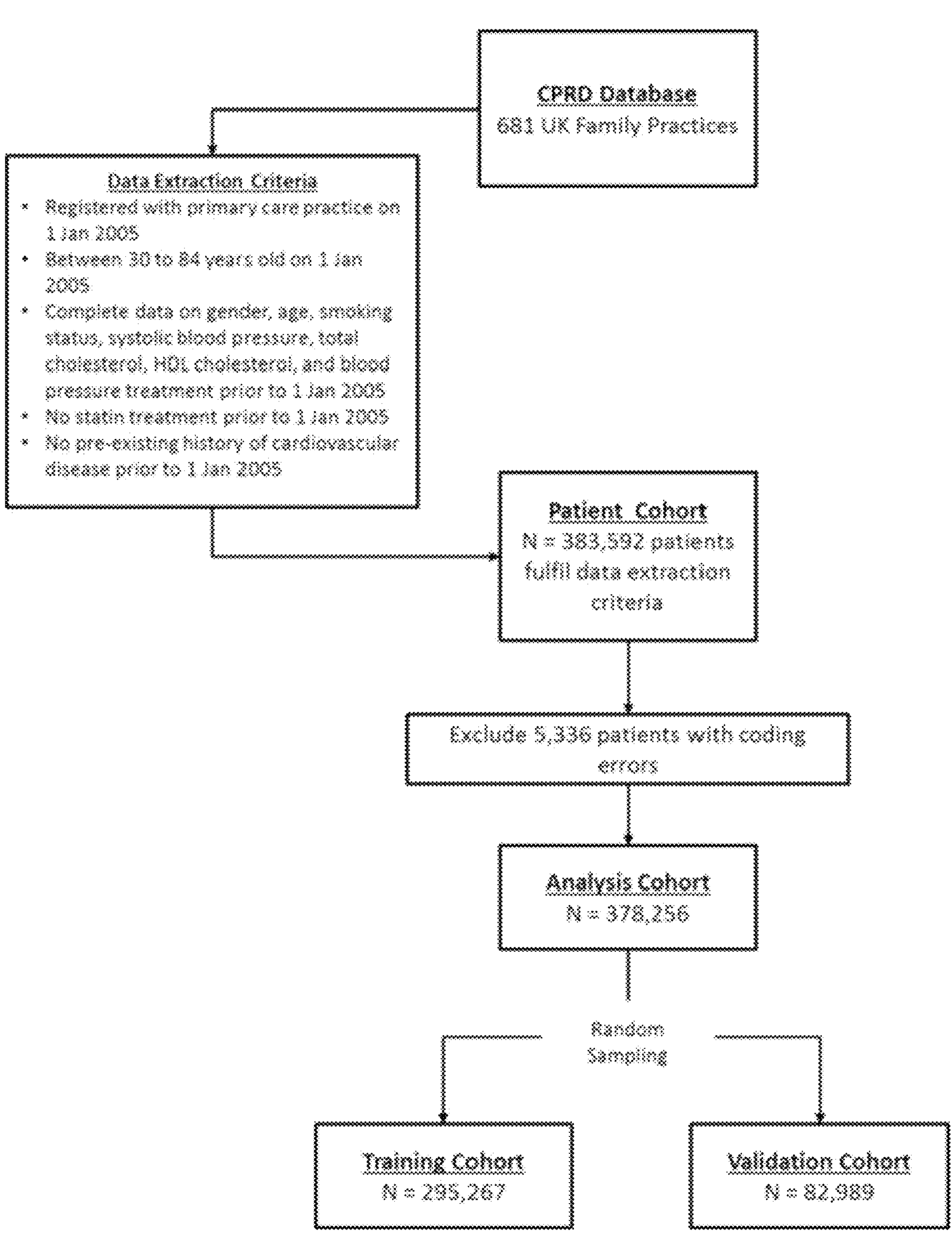
FIG. 70 depicts Data Extraction for Training Machine Learning Systems with Medical Outcomes.

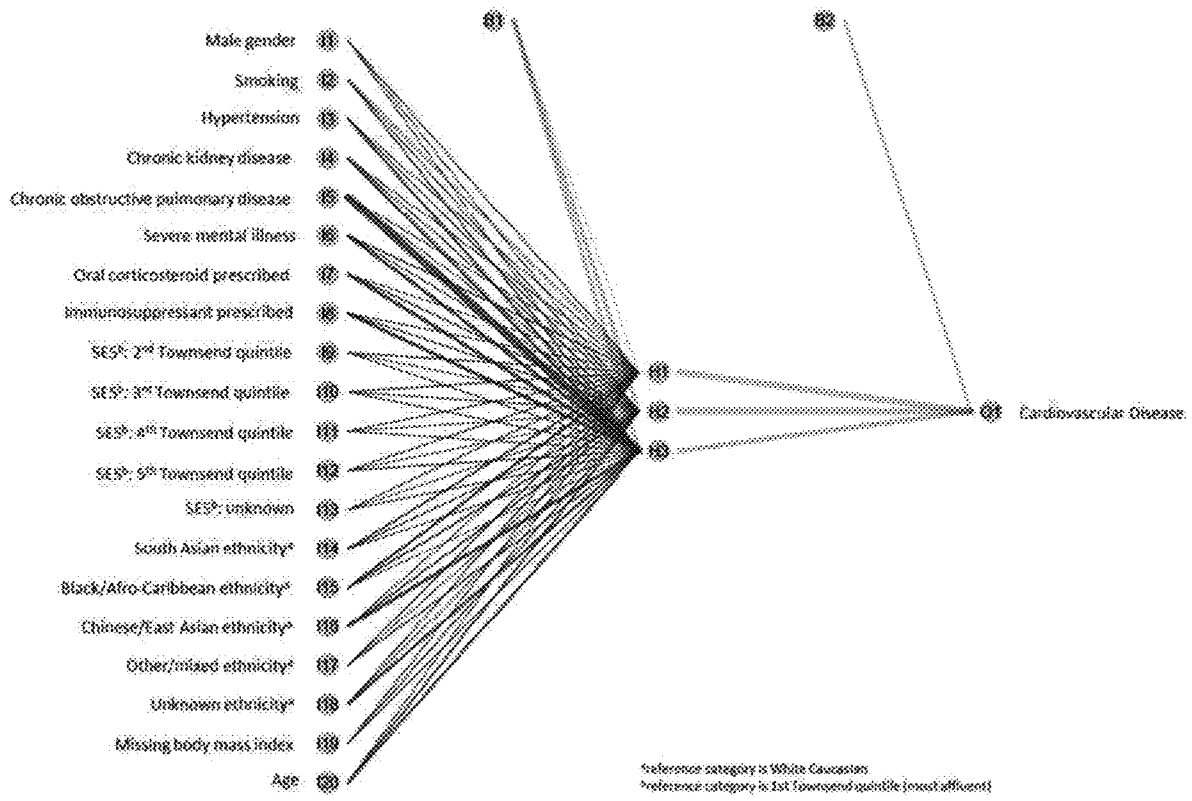
FIG. 71 depicts illuminating "black-box" understanding of Machine Learning results developed from Neural Networks `[e.g., XAI – Explainable Artificial Intelligence].

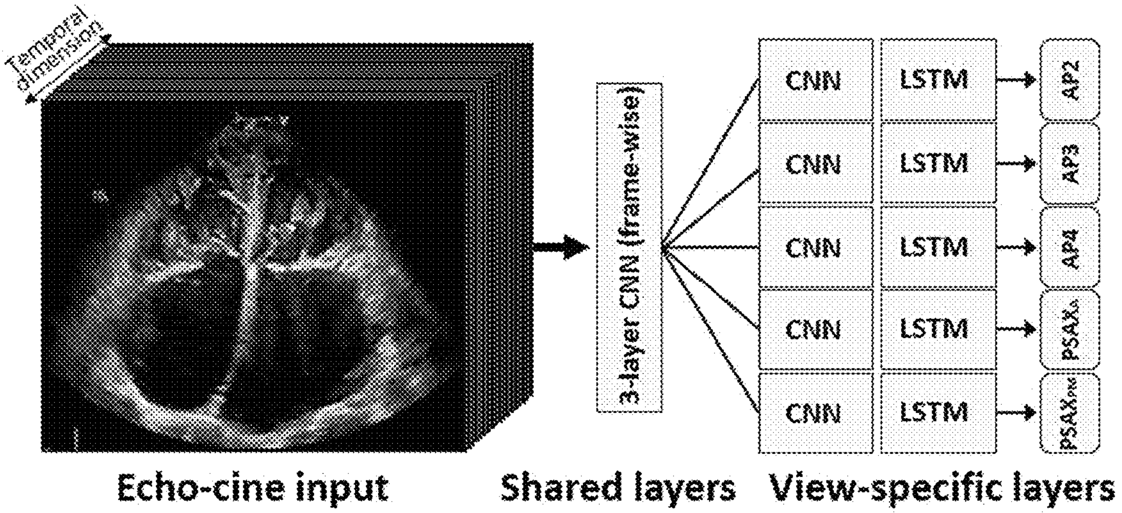
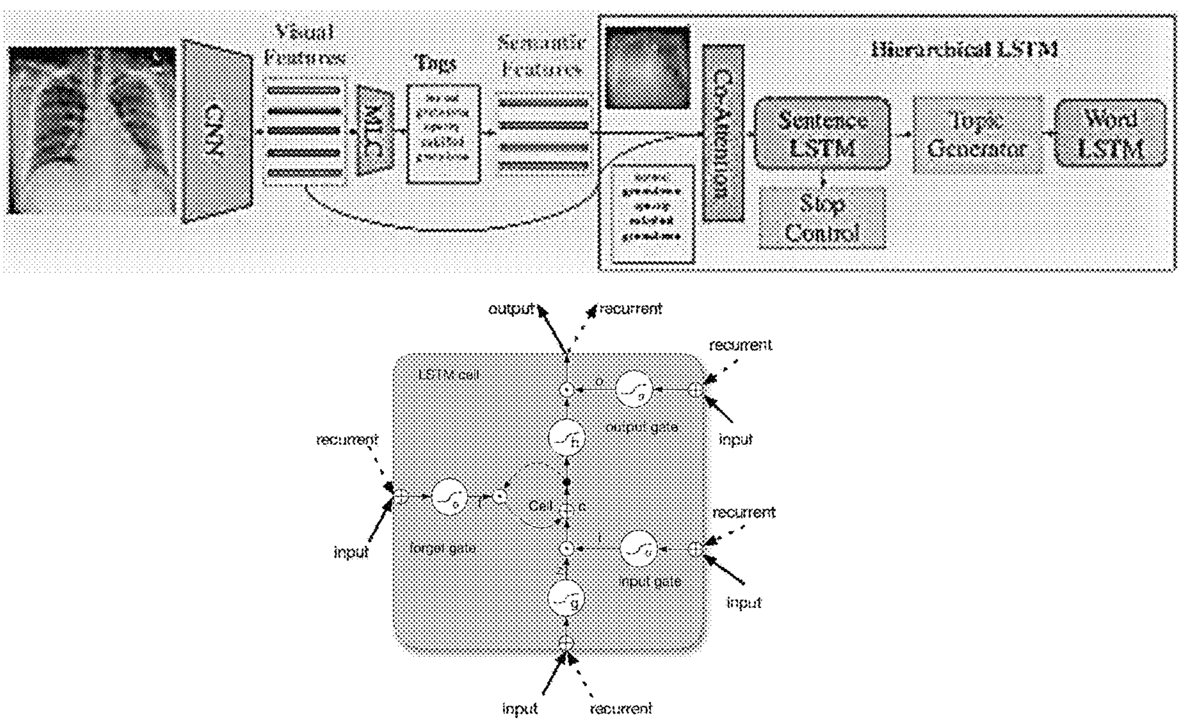
FIG. 72 depicts Convolutional and Recurrent Neural Networks with Long Short-Term Memory [LSTM] in Medical Imaging.

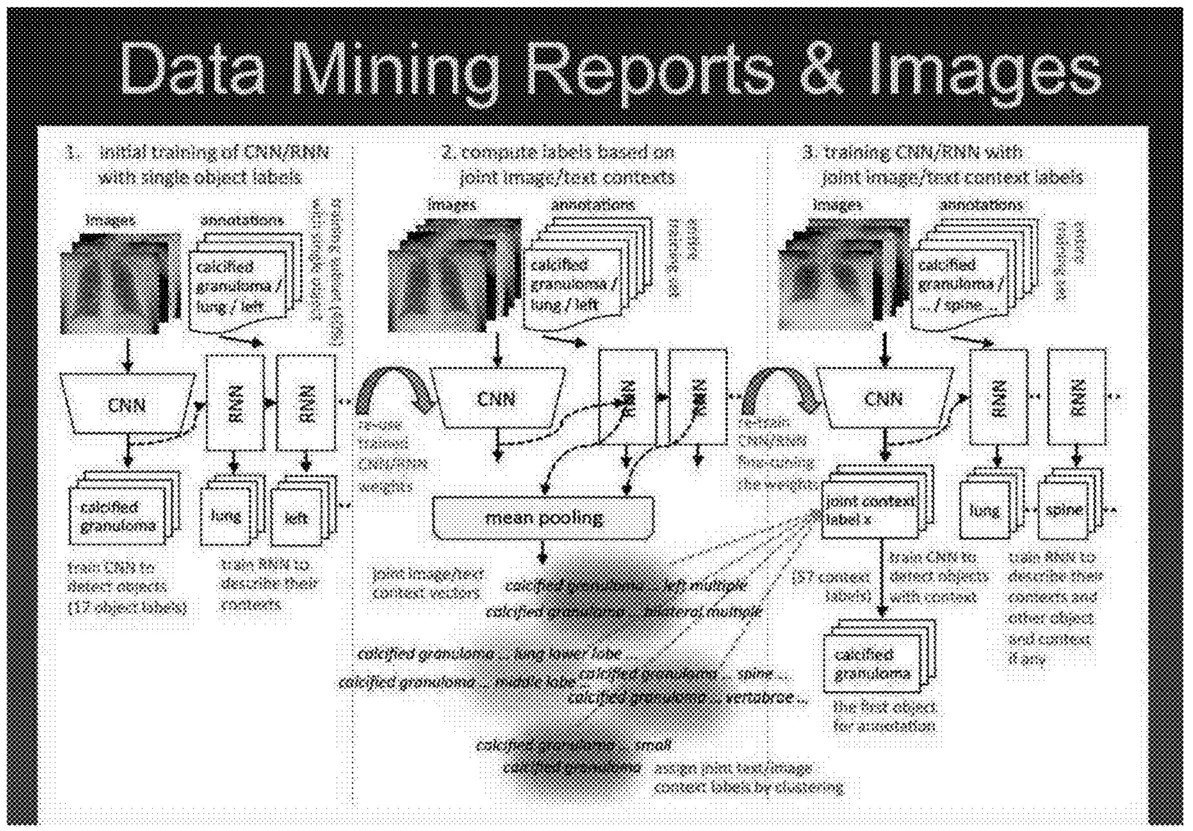
FIG. 73 depicts Data Mining, Training and Labeling with Annotated Medical Images using Convolutional and Recurrent Neural Networks with LSTM.

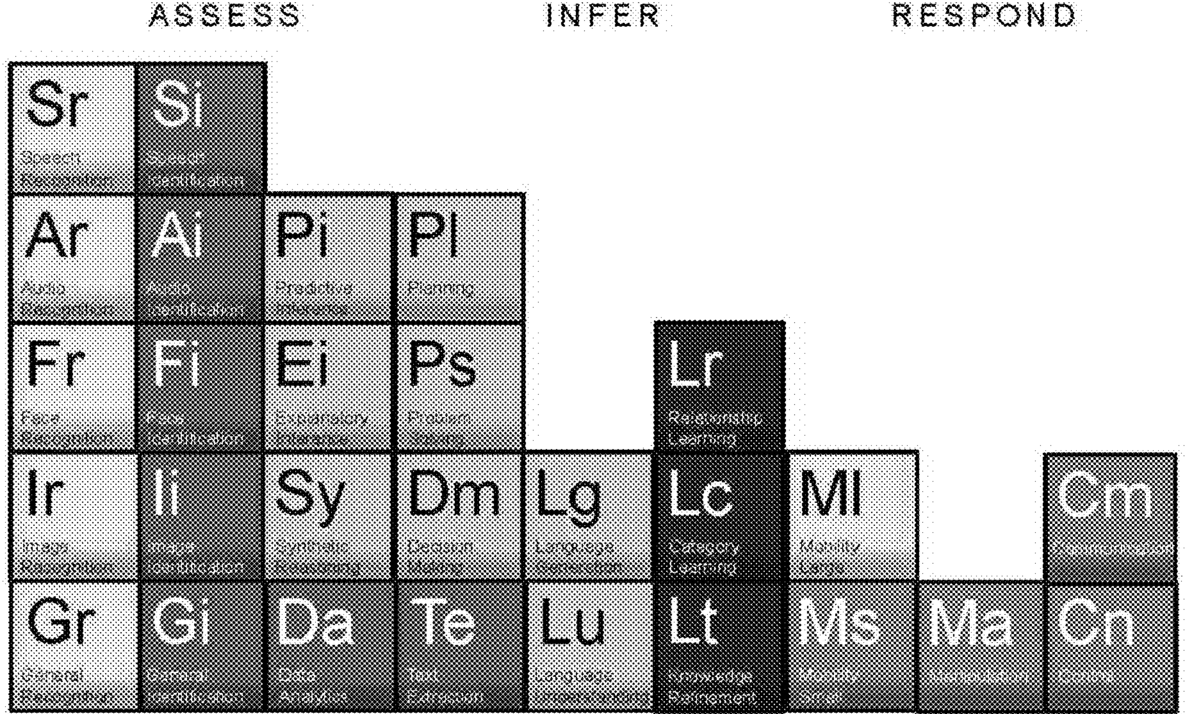
FIG. 74 depicts a Periodic Table of Artificial Intelligence with "Elementary" PAIR Techniques [Perceive-Assess-Infer-Respond].

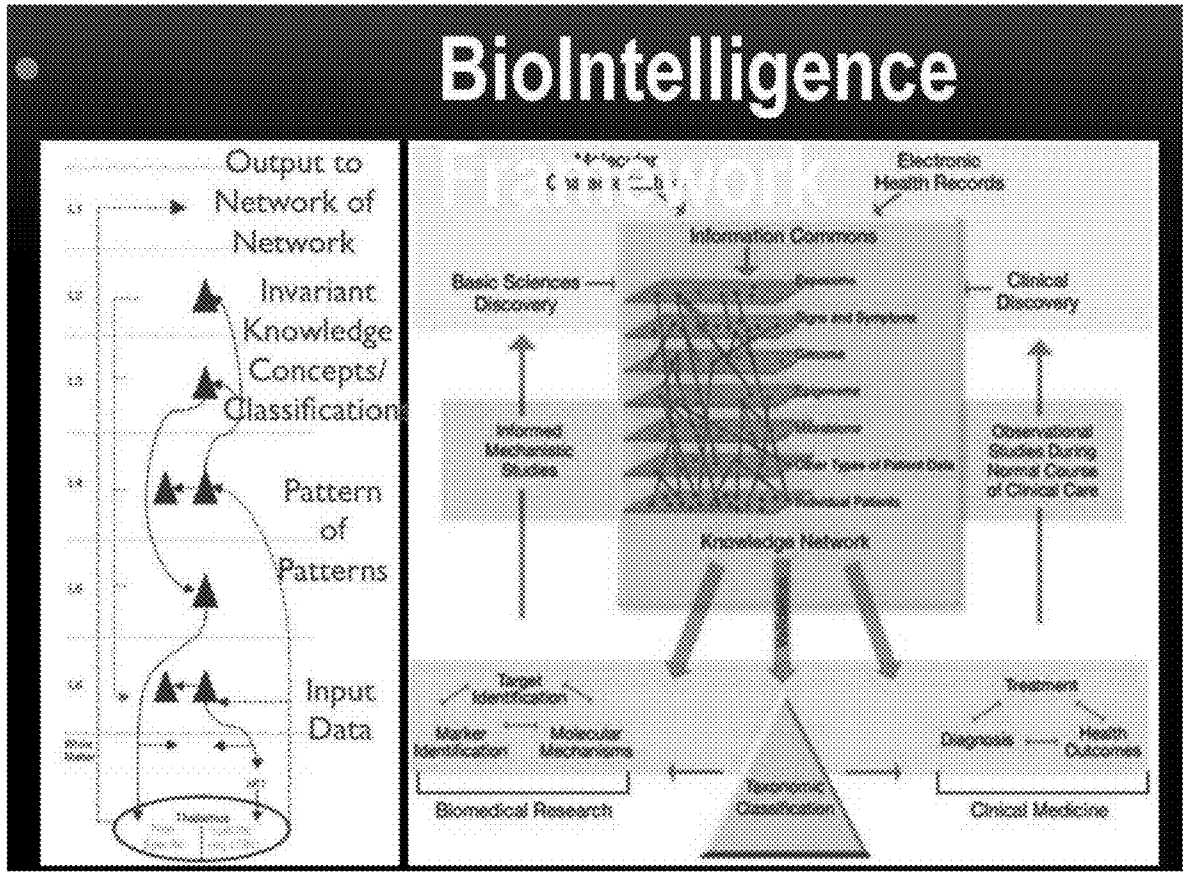
FIG. 75 depicts implementing Data-Information-Knowledge Networks with Machine Learning for BioIntelligence.

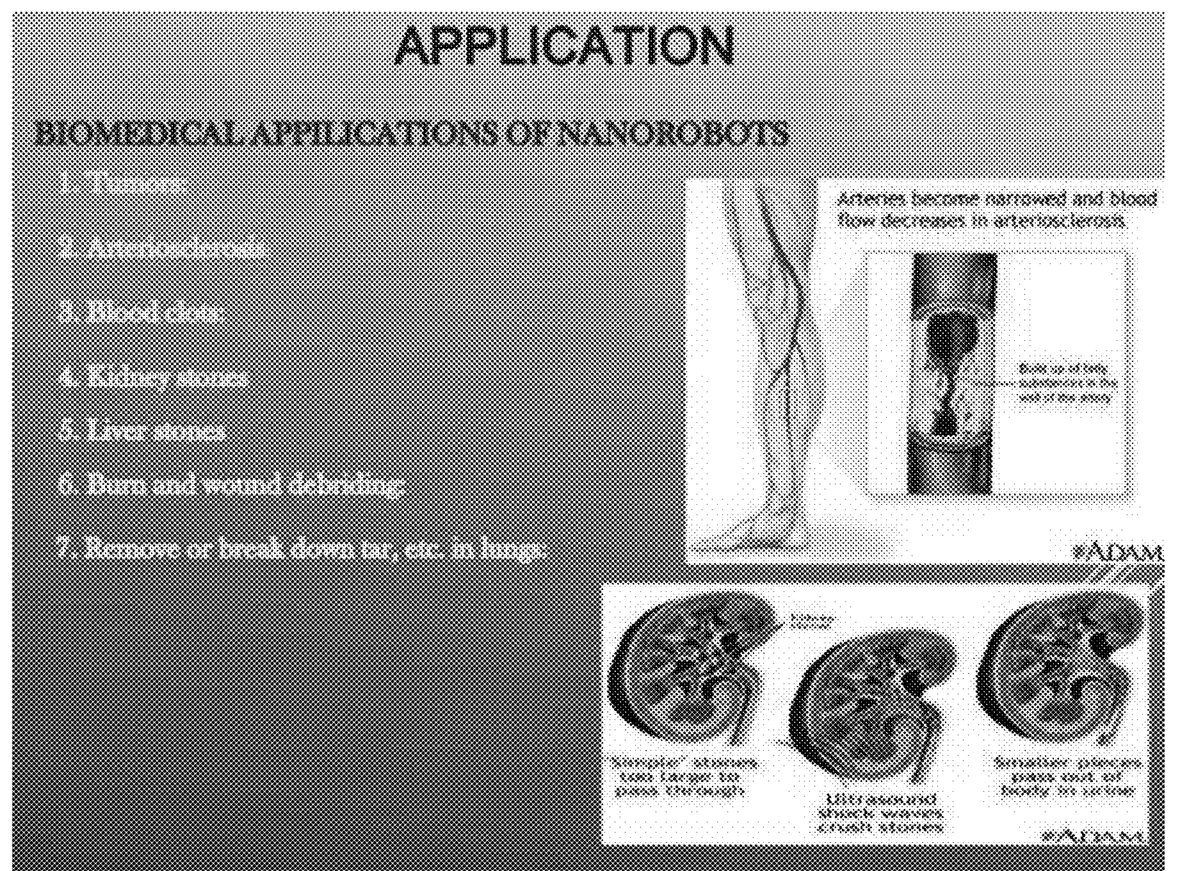
FIG. 76 depicts various biomedical applications for Nanorobotics.

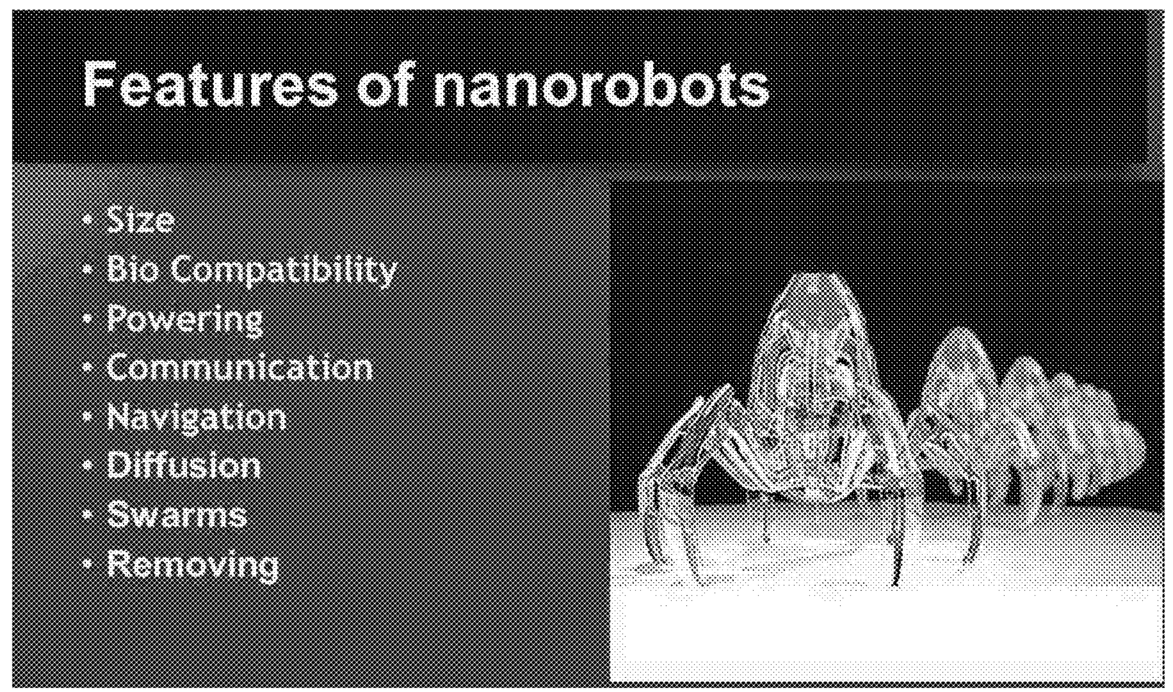
FIG. 77 depicts several typical features of Nanorobots.

FIG. 78 depicts monitoring Nanorobotic agents designed to treat cancer.

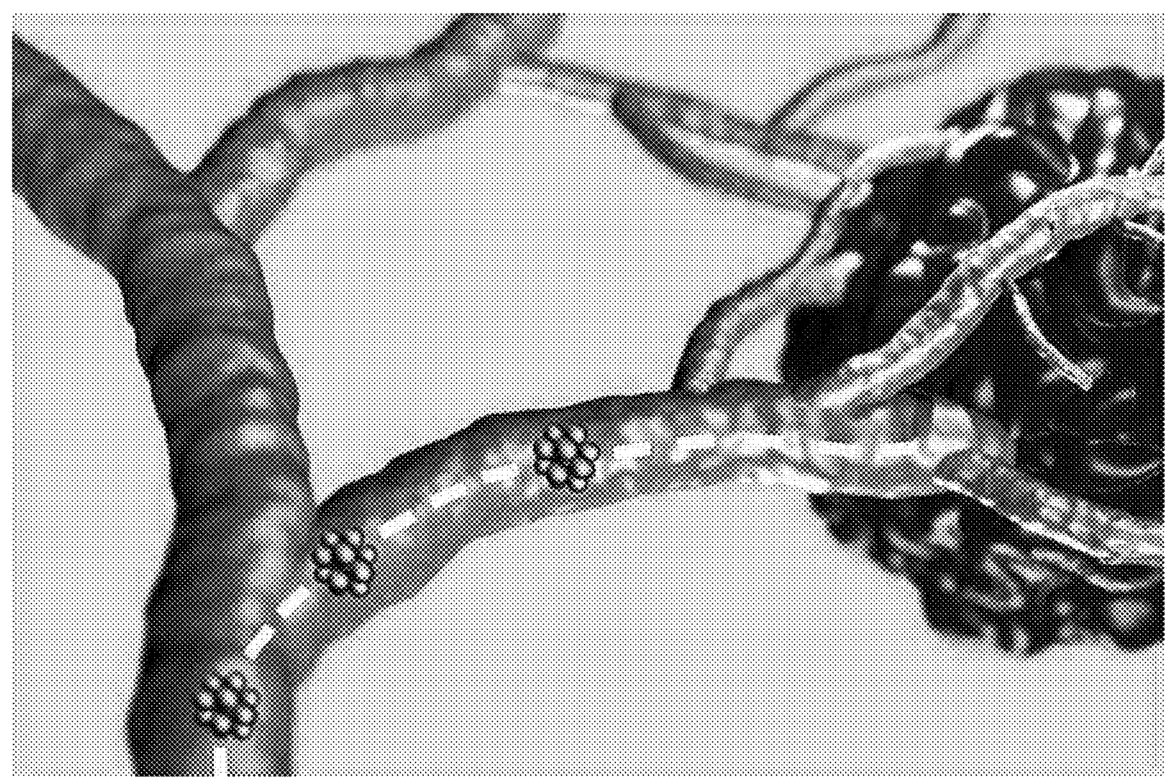
FIG. 79 depicts medical micro robots actuated by clinical MRI scanners.

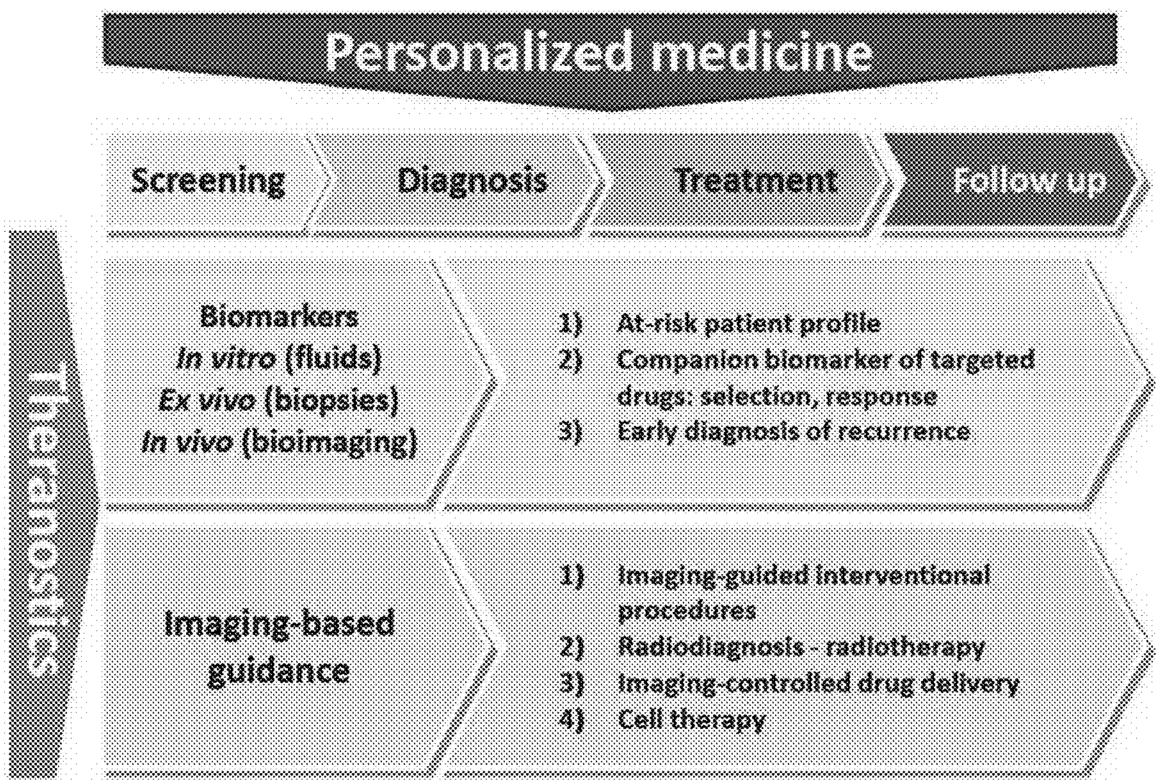
FIG. 80 depicts Personalized Precision Targeted Theranostic Nanomedicine.

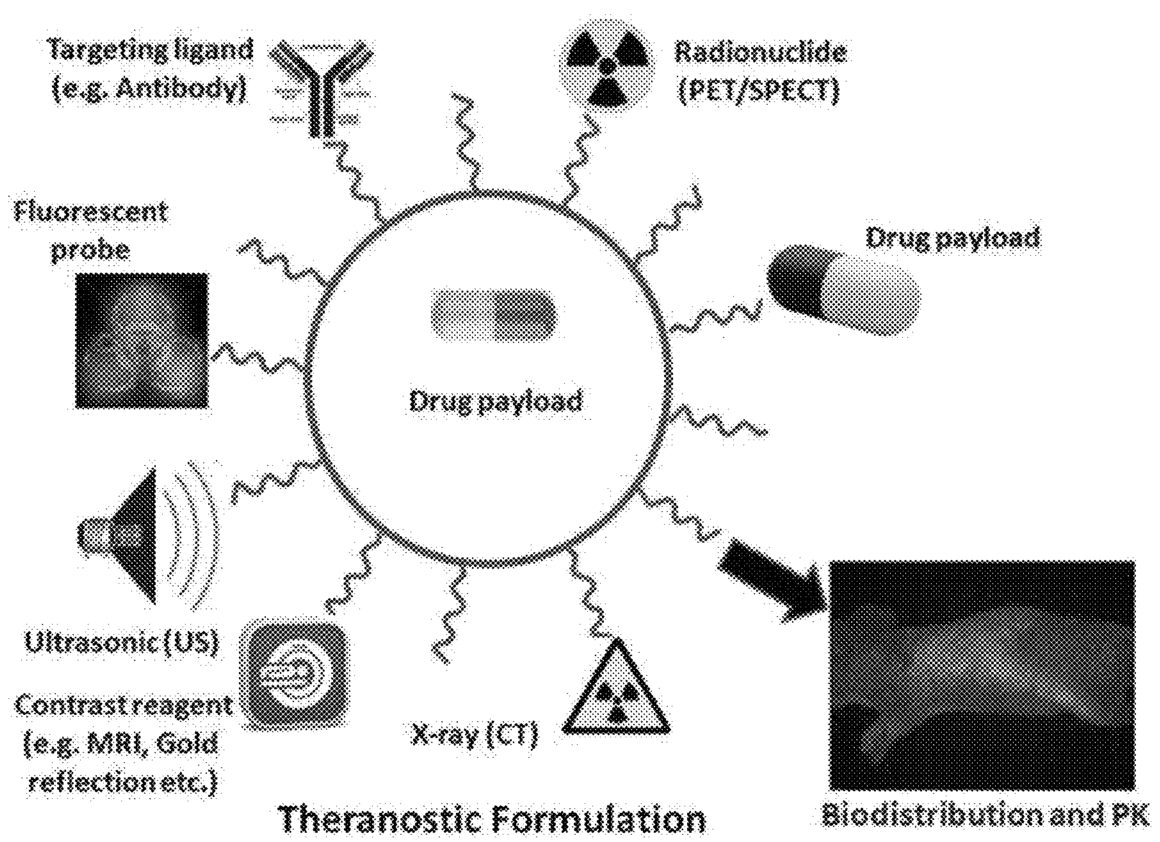
FIG. 81 depicts Imagery Guided Precision Theranostics with Targeted Drug Payloads.

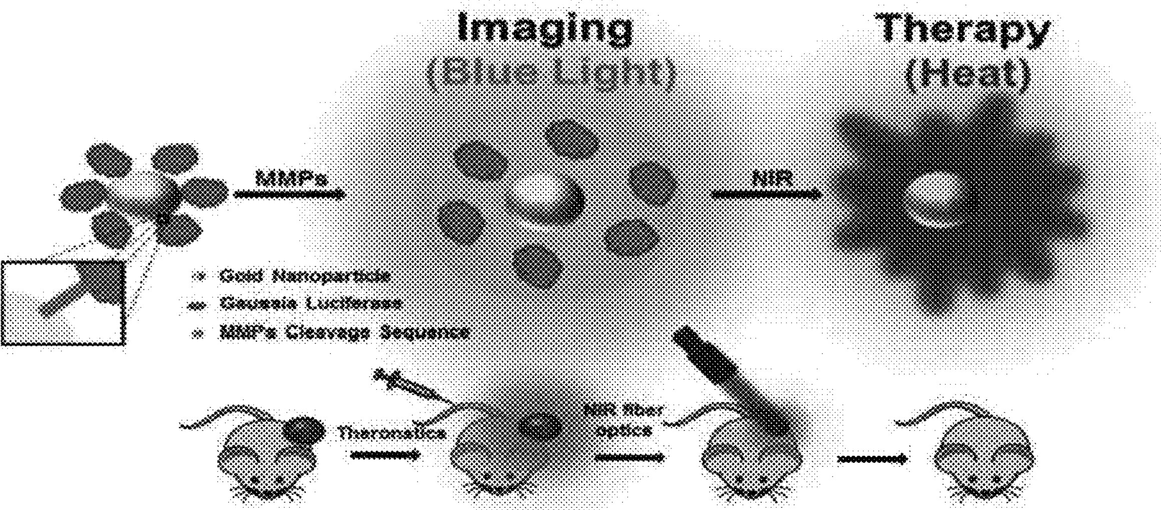
FIG. 82 depicts Nanoparticle-based Imaging Diagnostics and Therapy.

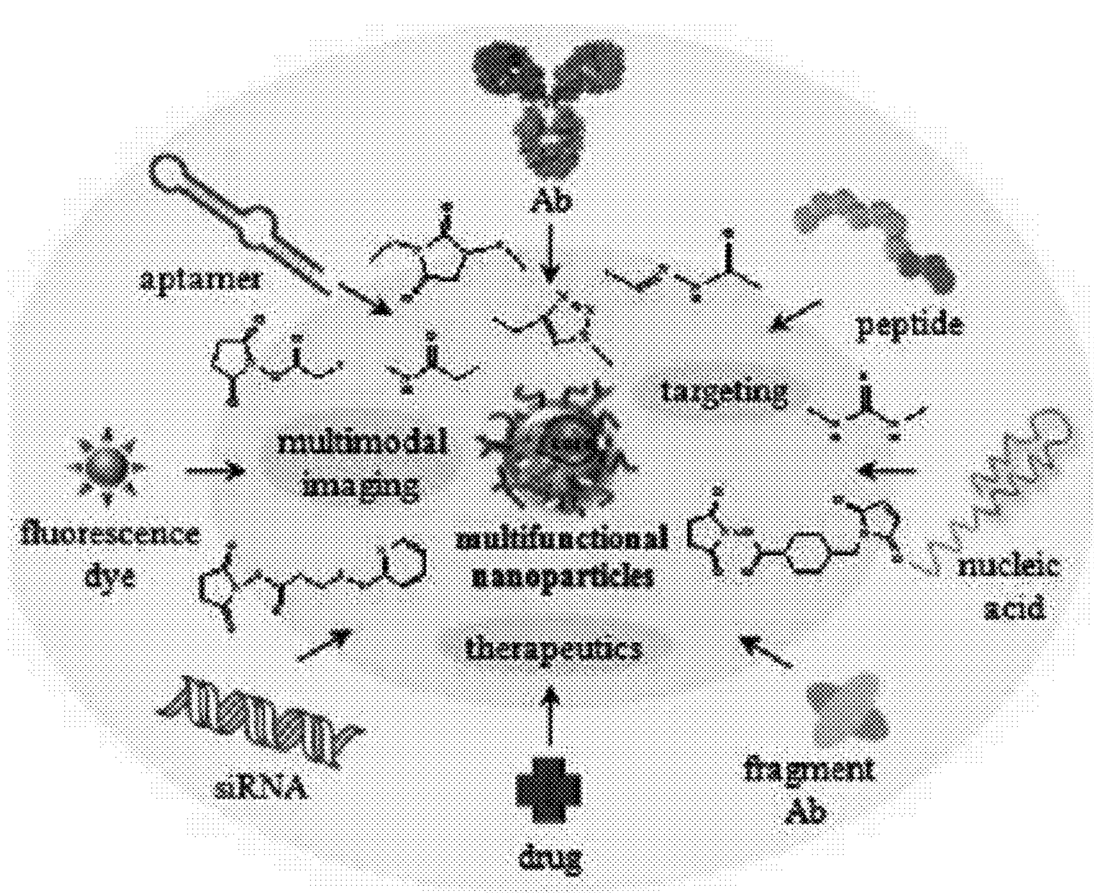
FIG. 83 depicts Multifunctional Nanoparticles for Theranostic Nanomedicine.

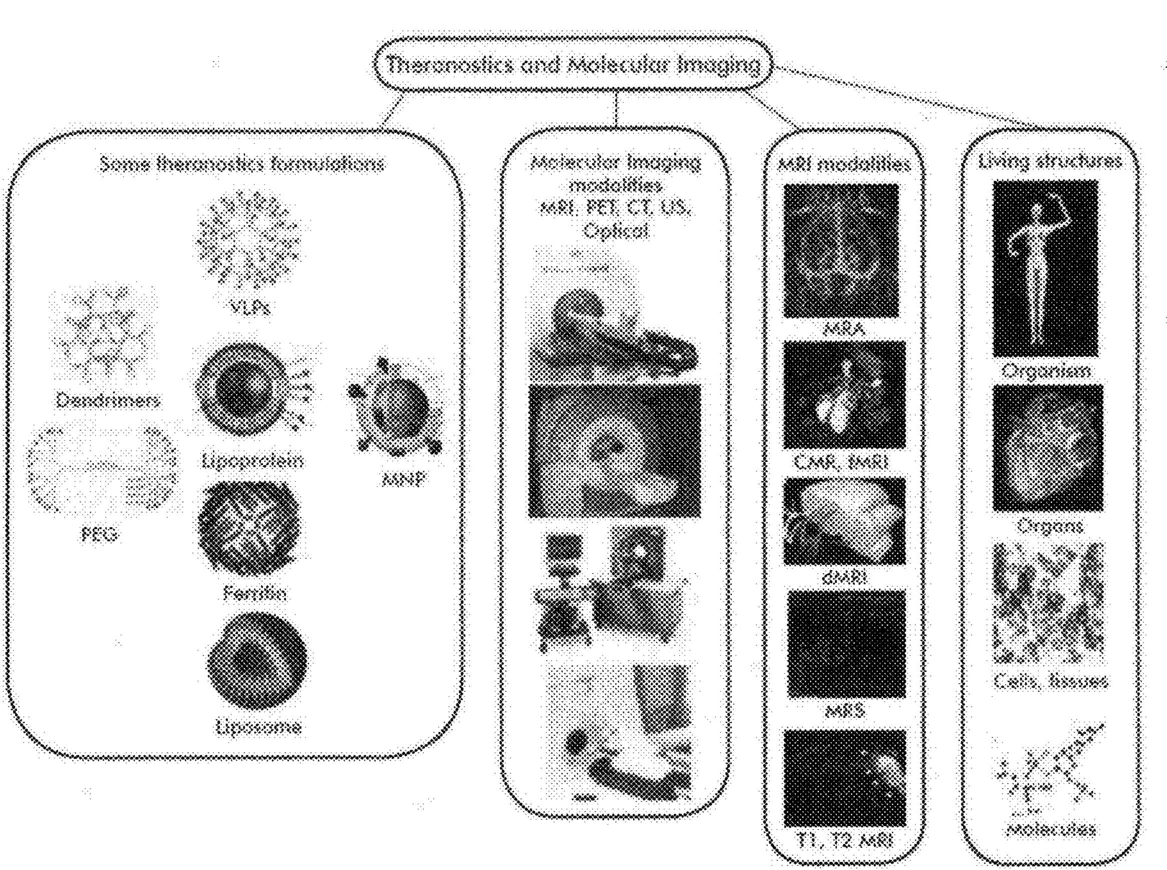
FIG. 84 depicts Integrating Theranostics Techniques with Molecular Imaging Modalities.

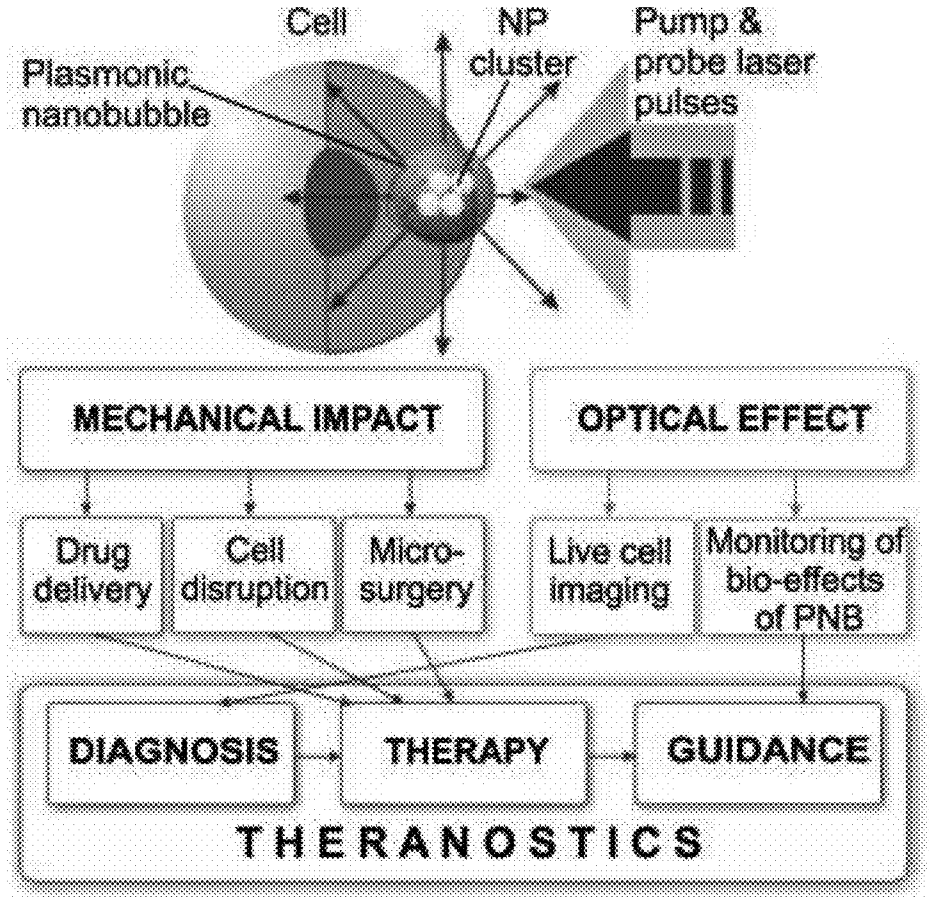
**FIG. 85 depicts Drug Delivery, Cell Destruction and Micro-Surgery with *in vivo* Imaging Theranostics.**

COGNITIVE COMMUNICATIONS, COLLABORATION, CONSULTATION, AND INSTRUCTION WITH ADAPTIVE AGENTIC AI, AUGMENTED GENERATIVE INTELLIGENCE AND NEUROSYNAPTIC COGNITION NETWORKS

FIELD

The invention generally relates to a network system and methods for receiving and transmitting streaming imagery data, including medical images, waveforms, audio and haptic signals, biomedical and clinical documents, both live and asynchronously, and allowing operators to concurrently curate, annotate, tag, encapsulate and save that imagery data, together with those annotations and searchable metadata tags in single file format structures. The invention acquires streaming imagery data through network-connected imagery-enabled devices, and allows a variety of cognitive collaborants, singly or together, to concurrently communicate, collaborate, consult and instruct, generally by curating, annotating and tagging, telestrating, sketching image overlays on streaming imagery data, and saving those images together with collaborated annotations and metadata, as streaming augmented intelligence for rapid adaptive learning, specialist skills acquisition and informatics-enriched innovation with multimodal clinical instruction and value chain knowledge exchange.

IMPROVEMENT OVER PRIOR ART

As used herein, “cognitive collaborant” refers to one or more cognitive collaborators, human or non-human, including persons, machines, devices, neural networks, robots and algorithms, as well as heterogeneous networked teams of persons, machines, devices, neural networks, robots and algorithms.

“Cognitive collaborant” will be described more fully below.

The invention enables multichannel multiplexed communications, collaboration, consultation and instruction with streaming imagery data by cognitive collaborants, including heterogeneous networked teams of persons, machines, devices, neural networks, robots and algorithms. The invention enables both synchronous and asynchronous multimodal clinical communications, collaboration, consultation and instruction during various stages of medical disease and injury management, including detection, diagnosis, prognosis, treatment, measurement, monitoring and reporting, as well as workflow optimization with operational analytics for outcomes, performance, results, resource utilization, resource consumption and costs.

The invention enables pluribus network encoding with multichannel multiplexed steaming imagery data from signals, sensors and devices, including packets, waveforms and streams, along with space shifting, time shifting and format shifting media synchronization. The invention enables heterogeneous networked teams of cognitive collaborants to recursively curate, annotate and tag, encapsulate, save and share multichannel multiplexed imagery data streams, including multisensory data stream visualizations, and bi-directional value chain knowledge exchange, with streaming imagery data from heterogeneous spatial and temporal sources, locations, modalities and scales. The invention can acquire both live stream and archived medical imagery data from network-connected medical devices, cameras, signals and sensors. The network system can also acquire multiomic data—phenotypic, genomic and metabolomic, as well as pathomic, radiomic, radiopathomic and radiogenomic—from structured reports and clinical documents, as well as biometric maps, movies, data stream visualizations, hapmaps and heat maps. The network system can also acquire packetized clinical informatics from imagery data repositories, from clinical workstations and mobile medical devices, as well as from wearable computing devices, signals and sensors.

The invention enables networked teams to interactively communicate, concurrently collaborate and bi-directionally exchange multichannel multiplexed imagery data streams, singly or together, in real time or asynchronously, generally by curating, annotating and tagging imagery information objects. The invention encapsulates and saves collaborated imagery data streams, together with collaborated clinical annotations, imaging metadata, as well as semantic metadata and annotations, and privacy protected metadata identifying personal health information [PHI], in standard known file formats as clinical cognitive vismemes—encapsulated packets, waveforms and streams. Clinical cognitive vismemes preserve packetized imagery information objects, clinical annotations and metadata tags in native file format structures, including PDF, MPEG, JPEG, XML, XMPP, TIFF, RDF, RDF/XML, QR, SVG and DAE, as well as DICOM. When clinical cognitive vismemes are encapsulated and saved in formats compliant with standards for digital communications in medicine [DICOM], they can also be referred to as medical dicom vismemes.

Clinical cognitive vismemes allow for recursive cognitive enrichment through recursive curation, annotation, tagging, encapsulation and saving, together with value chain knowledge exchange. Value chain knowledge exchange includes knowledge creation and acquisition, knowledge visualization and sharing, knowledge replication and integration, knowledge protection and destruction, as well as outcomes performance evaluation and learning, all of which can accelerate outcomes-driven innovation.

The invention also enables informatics-enriched innovation and value chain knowledge exchange with multimodal clinical communications and multisensory data stream visualization. Multimodal clinical communications, collaboration, consultation and instruction includes multisensory [sight-sound-touch]digital data exchange with vision, audition and sensation, including semiotics, semantics and somesthetics [haptics].

The invention enables live stream multicasting of N-way multi-party collaborations, including multisensory data stream visualization and bi-directional knowledge exchange, with multichannel multiplexed imagery data streams, and concurrent transmission of secure, encrypted clinical cognitive vismemes across collaborative file sharing data networks for informatics-enriched learning, specialist skills acquisition and accelerated knowledge exchange. Principal areas of clinical application include cognitively-enriched enterprise imaging with streaming imagery informatics, collaborative precision medicine with multiomic data analytics, informatics-enriched imagery guided intervention, including robotic-assisted surgery, along with newly-emerging disciplines for machine learning with medical imaging, including deep learning, transfer learning, reinforcement learning, convolutional neural networks, recurrent neural networks, long short term memory networks and natural language processing, along with emerging techniques for precision guided biomedical nanorobotics and precision targeted theranostic nanomedicine.

The novelty of the present invention enables multiparty networked clinical communications, collaboration, consultation and instruction with streaming imagery data by integrating videoconferencing systems technology with emerging applications and techniques for machine learning in medicine.

In addition to these, the present invention supports several additional improvements over prior art, including advances in Generative AI systems, advances in computer-assisted drug design and treatment, and incorporating multimodal media into Large Language Models (LLMs) in medicine, all of which are briefly described below.

1. Generative AI

Commonly Found References to "Generative AT" Include:

"Generative AI, or generative artificial intelligence, refers to a type of AI that is capable of generating new content such as text, images, videos, or other data types. It uses generative models which learn the patterns and structures from input training data and then produce new, similar data1.

This technology has seen significant advancements with the development of transformer-based deep neural networks and large language models (LLMs), leading to a boom in generative AI systems in the early 2020s1.

Examples include chatbots like ChatGPT and Copilot, text-to-image AI systems like Stable Diffusion and DALL-E, and text-to-video generators1.

Generative AI has a wide range of applications across various industries, including software development, healthcare, finance, entertainment, customer service, sales, marketing, art, writing, fashion, and product design1. However, it's important to be aware of potential concerns such as cybercrime, the creation of deepfakes, and the impact on employment1."

1.1 What is Generative AI?

Commonly Found References to "What is Generative AI" Include:

"The term generative AI refers to AI systems that can create new content, such as text, images, audio, video, visual art, conversation and code.

Generative AI models create content by learning from large training data sets using machine learning (ML) algorithms and techniques. For example, a generative AI model tasked with creating new music would learn from a training data set containing a large collection of music. By employing ML and deep learning techniques and relying on its recognition of patterns in music data, the AI system could then create music based on user requests."

"Generative AI models are built on several types of ML algorithms, each with different capabilities and features. The following are some of the most common:

Generative adversarial networks (GANs). Introduced in 2014, GANs are ML models in which two neural networks compete. The first network (the generator) creates original data, while the second (the discriminator) receives data and labels it as either AI-generated or real. By employing deep learning methods and a feedback loop that penalizes the discriminator for each mistake, the GAN learns how to generate increasingly realistic content.

Variational autoencoders (VAEs). Also introduced in 2014, VAEs use neural networks to both encode and decode data, enabling them to learn techniques for generating new data. The encoder compresses data into a condensed representation, and the decoder then uses this condensed form to reconstruct the input data. In this way, encoding helps the AI represent data more efficiently, and decoding helps it develop more efficient ways of generating data. VAEs can complete a variety of content generation tasks.

Diffusion models. Created in 2015, diffusion models are popular for image generation. These models work by gradually adding noise to input data over several steps to create a random noise distribution, then reversing this process to generate new data samples from that noise. Many image generation services, like OpenAI's Dall-E and Midjourney, apply diffusion techniques along with other ML algorithms to create highly detailed outputs.

Transformers. Introduced in 2017 to improve language translation, transformers revolutionized the field of natural language processing (NLP) through their use of self-attention mechanisms. These mechanisms enable transformers to process large volumes of unlabeled text to find patterns and relationships among words or sub-words in the data set. Transformers opened the door for large-scale generative AI models, especially LLMs, many of which rely on transformers to generate contextually relevant text.

Neural radiance fields (NeRFs). Introduced in 2020, NeRFs employ ML and artificial neural networks to generate 3D content from 2D images. By analyzing 2D images of a scene from various angles, NeRFs can infer the scene's 3D structure, enabling them to produce photorealistic 3D content. NeRFs show potential to advance multiple fields, such as robotics and virtual reality."

1.2 Features and Characteristics of Generative AI

Commonly found references to "Features and characteristics of Generative AI" include:

"Some of the main features and characteristics of generative AI are:

- Data-driven: It relies on large amounts of unlabeled or semi-labeled data to learn the patterns and structure of the input data.
- Neural networks: It uses deep neural networks, such as transformers, GANs, and VAEs, to model complex and high-dimensional data distributions and generate diverse outputs.
- Self-learning: It can learn from its own outputs and improve over time by adjusting its parameters and algorithms.
- Creative: It can generate original and surprising content that may not exist in the real world or may not be easily imagined by humans.
- Collaborative: It can interact with humans or other AI systems to co-create content or solve problems."

1.3 Transformer-Based Deep Neural Networks

Commonly Found References to "Transformer-Based Deep Neural Networks" Include:

"Key Points about Transformers:

1. Contextualization via Attention Mechanism:
   - Transformers excel at understanding context and dependencies in sequential data.
   - They employ a modern mathematical technique known as attention or self-attention.
   - This mechanism allows Transformers to identify how distant data elements influence and depend on one another.
2. Token-Based Representation:
   - Text input is converted into numerical representations called tokens.
   - Each token is then transformed into a vector using a word embedding table.
   - This process enables the model to capture semantic meaning.
3. Multi-Head Attention:
   - At each layer, tokens are contextualized within a context window.
   - The parallel multi-head attention mechanism amplifies the signal for key tokens and diminishes less important ones.

Unlike recurrent neural networks (RNNs), Transformers have no recurrent units, leading to faster training times.

4. Applications and Pre-Trained Models:

Initially used for natural language processing (NLP), Transformers have expanded to other domains such as computer vision, audio, and multi-modal processing.

Notable pre-trained systems include GPTs (Generative Pre-trained Transformers) and BERT (Bidirectional Encoder Representations from Transformers)."

1.4 Large Language Models (LLMs)

Commonly found references to "Large Language Models (LLMs)" include:

"Large Language Models (LLMs) are advanced AI systems capable of understanding and generating natural language, as well as performing a variety of other tasks. They are trained on vast amounts of data, which enables them to recognize patterns in language and generate coherent, contextually relevant responses. LLMs can be used for text generation, summarization, translation, question answering, and even creative writing or code generation tasks1.

These models have billions of parameters that help them capture the intricacies of language. They are a significant breakthrough in natural language processing (NLP) and have a wide range of applications, from chatbots and virtual assistants to content generation and language translation2. As technology evolves, LLMs continue to reshape our interaction with digital platforms and access to information123."

"Recent LLMs like GPT-4 offer multimodal capabilities, meaning that the model is able to work with other mediums, such as images and audio, along with language."

1.5 Small Language Model (SLMs)

Commonly found references to "Small Language Models (SLMs)" include:

"A Small Language Model (SLM) is a lightweight generative AI model. The term "small" in this context refers to the size of the model's neural network, the number of parameters the model uses to make decisions, and the volume of data the model is trained on1. Unlike their resource-intensive counterparts, such as ChatGPT and Google Bard, SLMs are designed to operate with fewer computational resources and memory.

Here are some key aspects of Small Language Models:

1. Size: SLMs can have less than 15 million parameters, making them compact compared to large language models (LLMs) with hundreds of billions of parameters.
2. Computational Requirements: SLMs can run on mobile device processors, whereas LLMs often require substantial GPU infrastructure.
3. Performance: SLMs excel at handling simple tasks, while LLMs can tackle more complex and diverse tasks.
4. Deployment: SLMs are easier to deploy in resource-constrained environments, such as Internet of Things (IoT) edge devices.
5. Training Time: SLMs can be trained in a matter of weeks, whereas LLM training can take months.

Keep in mind that while SLMs offer advantages like local data processing and reduced resource demands, their knowledge bases may be more limited than those of larger models, leading to potentially less accurate or nuanced responses1."

As used herein, Generative AI refers to systems of artificial intelligence incorporating machine learning (ML) algorithms, models and systems, including Generative adversarial networks (GANs), Variational autoencoders (VAEs), Diffusion models, Transformers, Neural radiance fields (NeRFs), Large Language Models (LLMs) and Small Language Models (SLMs).

2. Computer-Assisted Drug Design (CADD)

Commonly found references to "Computer-Assisted Drug Design (CADD)" include:

Computer-assisted drug design (CADD) is a comprehensive term that encompasses the application of computational techniques and artificial intelligence-based systems in the process of designing new therapeutics. These techniques aim to enhance the drug discovery process and improve clinical responses to drugs.

Let's delve into some aspects of CADD:

1. Computational Chemistry: This field employs mathematical models and simulations to predict molecular properties, interactions, and behavior. By analyzing chemical structures and their properties, researchers can identify potential drug candidates.
2. Molecular Modeling: Through molecular dynamics simulations and quantum mechanics calculations, scientists gain insights into how molecules interact with biological targets. This aids in predicting binding affinities and optimizing drug-receptor interactions.
3. Rational Drug Design: In this approach, researchers use structural information about target proteins (such as enzymes or receptors) to design molecules that specifically interact with them. Rational drug design aims to create compounds with desired properties, such as improved efficacy and reduced side effects.
4. Virtual Screening: CADD tools perform virtual screening by analyzing large databases of chemical compounds. By simulating their interactions with target proteins, researchers identify potential drug candidates for further investigation.
5. Anthraquinones: These naturally occurring compounds possess a unique scaffold and exhibit various biological properties, including anticancer activities. Researchers have used CADD to explore anthraquinone-based drug design for cancer treatment. By employing virtual screening methods, they aim to discover novel anthraquinone-derived drugs with enhanced efficacy and safety profiles1.

In summary, CADD plays a crucial role in streamlining drug development, optimizing resources, and guiding research toward innovative therapeutic solutions."

2.1 Computer-Aided Drug Design (CADD)

Commonly found references to "Computer-Aided Drug Design (CADD)" include:

"Computer-Aided Drug Design (CADD) is a powerful and interdisciplinary field that plays a pivotal role in modern drug discovery. It combines computational techniques with biological knowledge to identify and optimize potential drug candidates. The primary objective of CADD is to screen, optimize, and evaluate the activity of compounds against specific targets. This approach is used by both academic researchers and major pharmaceutical companies to enhance drug efficacy while minimizing side effects1."

"There are two main types of CADD:

1. Structure-Based Drug Designing (SBDD):

SBDD is the most efficient and powerful process in drug discovery.

It relies on information about the target, small molecules, genetic sequences, binding interactions, cytotoxicity, absorption, metabolism, excretion (ADMET) data, and other biological details. SBDD aims to design molecules that are complementary in shape to the biological target sites, allowing them to interact and bind effectively. This approach accelerates the drug discovery process by leveraging structural information1.

2. Ligand-Based Drug Designing (LBDD):

LBDD focuses on the ligands (small molecules) themselves rather than the target structure. It uses pharmacophore models to map key features of ligands and predict their biological activity. LBDD is particularly useful when detailed structural information about the target is lacking1."

"In summary, CADD harnesses computational methods to identify active compounds, optimize lead molecules, and improve drug efficacy while considering various pharmacokinetic parameters1."

2.2 Spatial Multiomics

Commonly found references to "Spatial multiomics" include:

"Spatial multiomics is an interdisciplinary field that combines genomics, transcriptomics, and proteomics with advanced imaging techniques. It aims to comprehensively analyze cells in tissues by enabling the joint analysis of multiple data modalities such as the transcriptome, epigenome, proteome, and metabolome.

These analyses can be performed in parallel or even on the same tissue section1. This approach is particularly useful for studying the complexity of diseases like cardiovascular diseases and understanding the molecular circuits and mechanisms that govern cell biology1."

"Spatial multiomics methods can resolve up to tens of thousands of individual molecules at a subcellular level, providing insights into the spatial organization of tissues and organs, which is crucial for maintaining their functions across various distances1."

"The field holds tremendous potential in revolutionizing our understanding of human disease processes and could contribute significantly to the advancement of personalized medicine1."

2.3 Morpholomics

Commonly found references to "Morpholomics" include:

"Morpholomics is a term used in cell biology to refer to the study of the morphology of differentiated cell types1. Morphology, in general, is a branch of biology that deals with the form and structure of organisms or any of their parts23. It's an important field for understanding how the structure of cells relates to their function and development."

3. Incorporating Multimodal Media into Large Language Models in Medicine

Commonly found references to "Incorporating Multimodal Media into Large Language Models in Medicine" include:

"A multimodal system can process and interpret multiple types of input data, such as text, images, audio, and video, simultaneously. Current medical AIs only process one type of data, for example, text or X-ray images.

The development of M-LLMs will have at least three significant consequences."

3.1 AI Will Handle Multiple Types of Content, from Images to Audio

"An M-LLM will be able to process and interpret various kinds of content, which is crucial for a comprehensive analysis in medicine. We could list hundreds of examples regarding the benefits of such a system but will mention only a few in the following five categories:

Text analysis: M-LLMs will be capable of handling a vast amount of administrative, clinical, educational and marketing tasks, from updating electronic medical records to solving case studies Image analysis: another broad area in terms of potential use cases, which spans from reading handwritten notes to analysing radiology (ophthalmology, neurology, pathology, etc.) images Sound analysis: M-LLMs will eventually become competent in disease monitoring such as checking heart and lung sounds for abnormalities to ensure early detection, but sounds can also provide valuable info in mental health and rehabilitation applications Video analysis: an advanced algorithm will be able to guide a medical student in virtual reality surgery training regarding how to aim precisely, move, proceed but videos could also be used to detect neurological conditions or to support patients communicating with sign language."

3.2 It Will Break Language Barriers

"These M-LLMs will easily facilitate communication between healthcare providers and patients who speak different languages, translating between various languages in real time."

3.3 Finally, the Arrival of Interoperability can Connect and Harmonise Various Hospital Systems "An M-LLM could serve as a central hub that facilitates access to various unimodal AIs used in the hospital, such as radiology software, insurance handling software, Electronic Medical Records (EMR), etc. The situation today is as follows:

One company manufactures software for the radiology department which use a certain format of AI in their daily work. Another company's algorithm works with the hospital's electronic medical records, and yet another third-party supplier creates AI to compile insurance reports. However, doctors typically only have access to the system strictly related to their field, for example, a radiologist has access to the radiological AI, but a cardiologist does not. And of course, these algorithms don't communicate with each other. If the cardiology department used an algorithm that analysed heart and lung signs, gastroenterologists or psychiatrists very likely wouldn't have access to it—even though its findings may be useful for their diagnosis as well.

The significant step will be when M-LLMs—eventually—become capable of understanding the language and format of all these software applications and help people communicate with them. An average doctor will then be able to easily work with the radiological AI software, the AI software managing the EMRs, and the fourth, and eighth (etc.) AI used in the hospital.

This potential is very important because such a breakthrough won't come about in any other way. No single company will come up with such software because they don't have access to the AI data developed by individual companies. The M-LLM however will be able to communicate with these systems individually and, as a central hub, will provide a tool of immense importance to doctors."

Improvements over prior art in the current invention also enhance previous improvements incorporated into prior versions of the current invention, described as follows:

4. Federated Learning (FL) is a Machine Learning Setting where Many Clients Collaboratively Train a Model Under the Orchestration of a Central Server, while Keeping the Training Data Decentralized.

"Federated learning is a machine learning setting where multiple entities (clients) collaborate in solving a machine learning problem, under the coordination of a central server or service provider. Each client's raw data is stored locally and not exchanged or transferred; instead, focused updates intended for immediate aggregation are used to achieve the learning objective."

Cross-silo applications for electronic health records mining and medical data segmentation Cross-Silo Federated Learning, Fully Decentralized/Peer-to-Peer Distributed Learning and Federated transfer learning Federated learning with edge computing, which affords greater data security, where its data is separately stored and processed in the edge node, as well as containerization, that provides management of all the various execution environments that devices in the edge federated learning setting will utilize.

The combination of edge computing and federated learning, together with Small Language Models (SMLs) deployed in network edge devices, along with more collaborative training methods for edge federated learning, can provides for better user experience and privacy protection.

5. Integration with Imaging Analytics for Preparing Medical Imaging Data for Machine Learning Image analysis is one of the most promising applications of artificial intelligence (AI) in health care, potentially improving prediction, diagnosis, and treatment of diseases. Federated artificial intelligence (AI)-based medical image analysis for the application of AI to large-scale clinical imaging data with decentralized local execution of data analyses can solve many obstacles of cross-site collaboration.

Supervised artificial intelligence (AI) methods for evaluation of medical images require a curation process for data to optimally train, validate, and test algorithms. The chief obstacles to development and clinical implementation of AI algorithms include availability of sufficiently large, curated, and representative training data that includes expert labeling (e.g., annotations).

New approaches such as federated learning, interactive reporting, and synoptic reporting may help to address data availability in the future; however, curating and annotating data, as well as computational requirements, are substantial barriers.

Advanced imaging analytics and the extraction of high-dimensional data from medical images, called radiomics, is emerging as the other side of the personalization coin. By adding an individual patients' tumor phenotypic (structural) information coupled with the patients' genetic data, drug developers can create more precise therapies.

By using artificial intelligence (AI), together with advances in computer-assisted drug design (CADD), to discern and compute data from medical images, radiomics enables drug developers to profile a patient, tumor, and therapy across multiple dimensions to find patterns and similarities that would otherwise be unobtainable.

6. Support for Interactive ("Visually Embedded") Annotations, as Well as Semantically Meaningful Segmentation, Parametric Maps and Structured Reports Traditionally, different annotation mechanisms have been provided in DICOM for the purpose of encoding, transporting and querying for clinically generated and machine generated image-related results. Some of these are purely focused on consistent rendering and appearance, and require visual human interpretation, while others are structured, coded and semantically meaningful, but require more work on the authoring side.

Modem AI workflow scenarios require more complex semantically meaningful payloads and interactions with the users, for training and testing, as well as for clinical operation. To the extent that DICOM payloads and protocols can be reused for both types of scenarios, the existing standard should be leveraged to implement new AI applications and existing templates and code sets.

The workflow has traditionally focused on human creation and display rather than automated analysis and consumption. Identify the workflow of annotation creation and use in AI using DICOM protocols and payloads.

Incorporating multimodal media into Large Language Models (LLMs) in medicine will enable more diagnostic and evidential static image, video clip, and sound multimedia to be captured during routine clinical care in cardiology, dermatology, ophthalmology, pathology, physiatry, radiation oncology, radiology, endoscopic procedural specialties, and other medical disciplines.

7. Interactive Multimedia Report (IMR) Creation and Ingestion into Electronic Health Records.

One Consensus Definition of IMR is

"interactive medical documentation that combines clinical images, videos, sound, imaging metadata, and/or image annotations with text, typographic emphases, tables, graphs, event timelines, anatomic maps, hyperlinks, and/or educational resources to optimize communication between medical professionals, and between medical professionals and their patients."

Providers typically describe the multimedia findings in contemporaneous electronic health record clinical notes or associate a textual interpretative report. Visual communication aids commonly used to connect, synthesize, and supplement multimedia and descriptive text outside medicine remain technically challenging to integrate into patient care.

Incorporating multimodal media into Large Language Models (LLMs) in medicine may eventually enable beneficial interactive data elements that include hyperlinks between text, multimedia elements, alphanumeric and geometric annotations, tables, graphs, timelines, diagrams, anatomic maps, and hyperlinks to external educational references that patients or provider consumers may find valuable.

8. Augmented Intelligence

Commonly Found References to "Augmented Intelligence "Include:

"Augmented intelligence is a subset of artificial intelligence (AI) that focuses on AI's assistive role, specifically designed to enhance human decision-making and cognitive performance rather than replace it. It leverages machine learning and deep learning to analyze vast amounts of data, which humans can then use to make more informed decisions and take action. Augmented intelligence aims to create a human-centered partnership model where humans and AI work together to improve tasks and decision-making processes1234."

"Here's a more detailed look at what augmented intelligence involves:

Human-AI Collaboration: It centers on the ways humans and machines can work together, enhancing human capabilities rather than removing the human element from certain work1.

Data Analysis and Decision Support: It uses machine learning to analyze data and help humans make smarter decisions. For instance, in retail, it can suggest optimal store layouts based on shopper data1.

Enhancing Cognitive Performance: Augmented intelligence is designed to improve learning, decision-making, and the creation of new experiences by working with humans3.

Continuous Learning Loop: Humans and machines are intertwined in a continuous learning and improvement loop, where both benefit from each other's strengths4.

In essence, augmented intelligence is about empowering humans with AI-driven insights and tools to enhance their natural abilities and productivity1234."

9. Augmented Generative Intelligence

Commonly found references to "Augmented Generative Intelligence" include:

"Augmented generative intelligence refers to the use of artificial intelligence (AI) to enhance and support human creativity and decision-making. It combines advanced machine learning algorithms, such as neural networks and deep learning, with human input to create new content like text, images, and videos.

This form of AI is designed not to replace human intelligence but to augment it, providing tools that help humans work smarter and more efficiently12."

"In the context of generative AI (GenAI), which focuses on creating content, augmented generative intelligence emphasizes the collaborative aspect where AI-generated insights, predictions, and recommendations are used alongside human expertise to foster innovation and improve performance2. It's a partnership between humans and AI, where the AI assists in the creative process, but the human remains in control of the final output and decisions12."

10. Augmented Generative AI

Commonly Found References to "Augmented Generative AI" Include:

"Augmented Generative AI refers to a fascinating intersection of artificial intelligence techniques that combines the power of generative AI with additional context and information. Let's break it down:

1. Generative AI:

Generative AI focuses on creating content, such as text, images, and videos, by leveraging techniques like neural networks and deep learning. These models aim to mimic human creativity and generate new, original content.

2. Retrieval-Augmented Generation (RAG):

RAG is a specific approach within generative AI that enhances the accuracy and reliability of AI models. It achieves this by fetching facts and information from external sources beyond the model's original training data.

Unlike fine-tuning, which adjusts model weights for specific tasks, RAG doesn't require weight adjustments. Instead, it retrieves relevant data from various sources to augment the model's responses.

By doing so, RAG keeps AI models fresh with up-to-date information and organizational knowledge.

Organizations find RAG valuable because it makes AI tools aware of proprietary data without the need for custom model training12.

3. Context and Context Windows:

Just like humans need context to make informed decisions, AI models also require context. Large language models (LLMs), structured as transformers, have a context window the amount of data they can process in a single prompt. RAG allows AI tools to use context beyond their training data, resulting in more contextually relevant responses for end users1.

In summary, augmented generative AI combines the creativity of generative models with the richness of external information, leading to more informed and context-aware AI responses."

As used herein, "cognitive collaborant" refers to persons, machines, devices, neural networks, robots or algorithms, including Augmented Generative AI algorithms, models and systems, learning through bidirectional communications, collaboration, consultation or instruction from at least one, or more persons, machines, devices, neural networks, robots or algorithms, including Augmented Generative AI algorithms, models and systems, as well as heterogeneous networked teams composed thereof.

As used herein, "Augmented Generative Intelligence" refers to cognitive collaborants learning through bidirectional communications, collaboration, consultation or instruction with Augmented Generative AI algorithms, models or systems.

BACKGROUND

Machine Learning in Medicine

Digital clinical data, captured and stored on electronic medical records by hospitals and clinics, along with ever growing volumes of medical imaging data, have sparked growing interest and applications of machine learning in medicine.

In recent years there has been a proliferation of artificial intelligence (AI) tools and resources available in medicine, especially with ever increasing computing power and a growing acceptance of cloud computing by hospitals and clinicians. Imaging analysis and clinical decision support are two particularly popular applications of machine learning in medicine, with tools that support diagnosis, treatment, care coordination and remote monitoring.

There is much promise in the utilization of AI methodologies such as machine learning and deep learning for augmented biomedical image interpretation in radiology, cardiology, pathology, dermatology, ophthalmology and genomic medicine.

One example of machine learning for medical imaging involves differential diagnosis of breast cancer enabled by joint analysis of functional genomic information and pathology images (pathogenomics) within a biomedical imaging informatics framework consisting of image extraction, feature combination, and classification.

Algorithms based on deep convolutional neural networks have been used to detect diabetic retinopathy in retinal fundus photographs with high specificity and sensitivity, as good as with board-certified ophthalmologists in making diagnoses.

Personalized precision medicine with all its complexity and enormity of data to be analyzed is particularly well suited for the portfolio of AI methodologies, including deep learning, which can be used to identify and assess patients with similar genotype-phenotype characteristics. In genomic diagnostics, clinicians are often frustrated by the tedious nature of searching for genotype-phenotype interrelationships among syndromes, especially for extremely rare diseases. Now, geneticists may be able to use visual diagnostic decision support systems that employ machine learning algorithms and digital imaging processing techniques in a hybrid approach for automated detection and diagnosis in medical genetics.

An essential part of the precision medicine paradigm is individualized therapy based on genotype-phenotype coupling and pharmacogenomic profiles. There are many potential applications of deep learning for large datasets in pharmaceutical research, such as physicochemical property prediction, formulation prediction, and properties such as absorption, distribution, metabolism, excretion, toxicity, and even target prediction.

Surgical robotics have advanced to include 3D visualization and informatics-enriched imagery guided interventions.

Machine learning algorithms can also be applied to large-scale wearable sensor data in neurological disorders such as Parkinson's disease to significantly improve clinical diagnosis and management. Sensor-based, quantitative and objective systems for assessing Parkinson's disease have the potential to replace traditional qualitative and subjective ratings by human interpretation.

An essential part of digital medicine and wearable devices is the data mining of the incoming data for anomaly detection, prediction, diagnosis and clinical decision making. Data mining processes for data streams from wearable devices typically include feature extraction/selection processes to improve detection, prediction, and decision making by clinicians.

Machine learning techniques include supervised methodologies such as neural networks, support vector machines, naïve Bayesian classifiers, and hidden Markov models, as well as semi-supervised methods that can be used with less labeled data. These techniques can be applied to molecular imaging modalities with promising application for clinical diagnosis.

Four types of machine learning—deep learning, reinforcement learning, transfer learning and one-shot learning—may figure prominently in future applications of AI in medicine.

Deep learning with all its myriad capabilities may well be used for many applications in medical data analytics. The multiple layers of neural nets can be assigned to the many phenotypic as well as genomic expressions of conditions such as clinical measurements, biomarkers, imaging data, genomic information and disease subtypes.

Reinforcement learning is ideally designed for the many decision-making aspects of medicine since it readily accommodates recognition of complex patterns, long-term planning, and many decision-making processes in clinical practice.

Transfer learning occurs when a network that is trained for one task is then used to configure the network for another task.

One-shot learning can bring a special dimension to unique cases in medicine as it does not require the usual large dimensionality of data that the other types of machine learning techniques typically require.

Natural language processing [NLP] includes machine learning techniques for speech recognition and identification, as well as language understanding and generation. Medical NLP may become increasingly useful for collaborative curation, annotation and tagging of medical imagery data by heterogeneous teams of medical minds and machines. Curated medical images, annotated and tagged as medical "ground truth", will become increasingly important not only for clinical detection, diagnosis and decision support, but also for the training, testing and validation at scale of machine learning algorithms requiring voluminous imagery data sets. Recurrent Neural Networks [RNN] and Long Short-Term Memory [LSTM] networks have been successfully applied to a variety of problems in speech recognition, language modeling and translation, image captioning and image annotation.

Personalized precision medicine may require disruptive computational platforms for new biomedical knowledge discovery, and scalable computational frameworks that can leverage hypergraph-based data models and query languages that may be well-suited for representing complex multilateral, multi-scalar, and multi-dimensional relationships. Hypergraph-like stores of clinical information (e.g., from disease registries) can be combined with an individual patient's genomic and other phenotypic information (such as imaging data) to create more precise and personalized genome-based knowledge stores for clinical translation and discovery. Patients of very similar genomic and clinical elements could then be better discovered and matched for diagnostic and therapeutic strategies.

Cloud computing and storage can facilitate a full range of AI techniques for multi-institutional collaborations that may become essential to driving future applications of AI in biomedicine and healthcare. The internet of medical things (IoMT) may also provide the critical data sources for medicine in the form of wearable and monitoring devices from both hospital and home.

Clinical data analytics will increasingly rely on machine learning tools and techniques to answer many clinical questions for intelligence-based medicine, rather than current best practices of principally relying upon published medical reports for evidence-based medicine.

There is a compelling need for informatics-enriched innovation with AI-powered technologies that can improve diagnostics and therapeutics, and help deliver value-based care. The convergence of "big data" stores, improved AI algorithms, increasing use of graphical processing computational power (GPU), and cloud storage has begun to produce some intriguing machine learning projects with promising results for biomedicine and healthcare. Perhaps more importantly, continuing advances with AI-powered tools and techniques in healthcare will require efforts to ensure more collaborative teamwork and better sharing of curated datasets among the various stakeholders.

Productive AI strategies may involve synergistic collaborations of humans and machines—clinicians and data scientists, empowered with AI—so that machine learning in medicine may become a key enabler of new clinical knowledge and augmented clinical intelligence for learning health care systems.

Collaborative Clinical Workflows with Enterprise Imaging

The HIMSS-SIIM Collaborative Workgroup has defined Enterprise Imaging as:

"The management of all clinically relevant content, including imaging and multimedia, for the purposes of enhancing the electronic health record through a set of strategies and initiatives designed and implemented across the healthcare enterprise. These strategies and initiatives are based on departmental and specialty workflows for all clinical imaging content, and include methods for capture, indexing, management, storage, access for retrieval, viewing, exchange and analytics."

Enterprise imaging (EI) platforms typically provide the infrastructure, modalities, devices, and integration points, as well as a standards-based repository for storage of both DICOM and non-DICOM clinical images and video. Those centralized image repositories—e.g., a vendor neutral archive or an enterprise wide PACS system—typically include indices of both image and metadata-information contents held in the archive.

Medical imaging archives are increasingly becoming modality agnostic, modality vendor agnostic, specialty and service line agnostic, and viewer agnostic. Standards-based interfaces and communications, including DICOM, HL7, and standards-based Web Services, connect, enable, and support image acquisition workflows across modalities and departments. Image acquisition devices that support these standards may store their images, with meta-information, into the VNA. Acquisition devices that are supported include departmental DICOM imaging modalities, point-of-care acquisition modalities, handheld device photo or video apps, digital capture systems in procedure rooms, image exchange gateways, and software designed to import content saved on a disk or received by referring or patient portals.

Clinical content and multimedia content span four broad categories of medical workflows within Enterprise Imaging: diagnostic imaging, procedural imaging, evidence imaging, and image-based clinical reports.

Medical workflows across many departments capture and create a variety of types of "multimedia" information that is important to preserve, correlate with the images, and make accessible via the patient medical record. Multimedia content includes waveforms, audio or video clips, as well as other forms of graphical content that summarize imaging results with the results from other medical procedures and tests. Non-radiological examples can be found in many specialties including Cardiology, Neurology, Gastroenterology, Ophthalmology and Obstetrics. Graphical "report-style" results from various medical departments are increasingly being created and saved as PDF objects. These can include embedded images that show key findings, graphical diagrams that show the area of interest, or other measurement or test result information that correlates with the images.

Other examples of related multimedia content include time-based waveforms such as those produced by ECG or EEG devices. These may be treated as documents or image-like objects. Waveforms may be recorded and stored in a raw or processed form that requires an application to display them, or in some human-readable rendered form (like a PDF or screenshot). Like images, waveforms too can be classified as both evidence and diagnostic. Waveforms are the graphical representation of discrete data points but may be used as the sole basis of interpretation when other tools for analysis of discrete data points are not available or routinely incorporated within the interpretation protocol.

Most types of multimedia content, including waveforms, PDF reports, MPEG video clips, and JPEG photos, can be DICOM wrapped and stored as DICOM objects or they can be treated as a native document type (e.g., PDF, JPEG, MPEG, etc.) and saved in systems that can manage them as native objects. An important consideration is how this information will be managed, correlated, accessed, and viewed by physicians and patients. Wherever possible, related patient images and multimedia content could be made readily discoverable and shown together in a useful, natural way.

DICOM provides support for encoding both generic identification and modality and specialty-specific acquisition context for all enterprise imaging modalities. DICOM-like metadata can also be added to other image file formats like JPEG or TIFF. Other alternatives include encapsulating the image in a different standard format, such as HL7 Clinical Document Architecture (CDA), as is defined by the IHE Scanned Document (XDS-SD) profile, so that metadata remains directly associated with their related medical images. The invention described herein supports both approaches to encapsulating and saving medical metadata together with their associated medical imagery.

Video Collaboration with Medical Imaging

This invention relates to a videoconferencing system for 'live', i.e., real time, near real time or minimally latent, viewing of streaming medical imagery, and more particularly, to a network system and methods of using said videoconferencing system with both medical and non-medical imagery, and multiple input operators (participant "cognitive collaborants"), each viewing the other's inputs collaboratively and concurrently.

In the past, video conferencing systems could be summarized as enabling a plurality of users systems connected to each other, each being adapted to display a work area on a display screen or connected through a computer network. Collaboration of work is done on each system by use of a management table for registered node identification codes given for each system user. That is, every computer system, or one system, requires storage of collaboration user identifier in at least one of the user's computer system. The novelty of the current invention—a system and methods of multimodal clinical communications, collaboration, consultation and instruction for use with medical imagery—has improved upon prior art by allowing modular and scalable network clusters of gateway streamer servers that enable dynamic control allowing for faster and more efficient performance, as well as enabling multiparty cognitive collaboration with medical imagery in a Digital Imaging and Communications in Medicine environment, hereinafter referred to as DICOM.

The DICOM Standard pertains to the field of medical imaging informatics. The DICOM Standard is well known in the arts and facilitates interoperability of medical imaging equipment by specifying a set of protocols to be followed by devices claiming conformance to the standard. The DICOM Standard outlines syntax and semantic of commands and associated information which can be exchanged using these protocols. For media communication, it provides a set of media storage services to be followed by devices claiming conformance to the DICOM Standard, as well as a file format and medical dictionary structure to facilitate access to the images and related information stored on interchange media. DICOM data file format is data formatted in groups of information, known as Data Sets. The DICOM Standard provides a means to encapsulate in a single file format structure the Data Set related to a DICOM information object. The DICOM Standard requires a single file format structure, as the DICOM Standard specifies that each DICOM file contain both File Meta Information and a properly formatted Data Set (as specified in DICOM Standard 3.10). The DICOM Standard further specifies that the byte stream of the DICOM Data Set be placed into the file after the DICOM File Meta Information (as specified in PS 3.10 DICOM Part10: Media Storage and File format for Media Interchange).

The DICOM Standard specifies the rules for encapsulating DICOM Data Sets in the requisite DICOM File format. The DICOM Standard requires that a file meta information header be present in every DICOM file, and that the file meta information includes identifying information of the Data Set (PS 3.7-1). The DICOM Standard requires that the Data Set conform to the service-object pair (SOP) Class specified in the file meta information. "The DICOM File format provides a means to encapsulate a File the Data Set representing a SOP Instance relating to a DICOM Information Object." The DICOM Standard provides for the encapsulation of waveform data (PS 3.5 Part 5: Data Structures and Encoding), and for the encapsulation of structured reports (Supplement 114: DICOM Encapsulation of Clinical Document Architecture Documents) within imagery bit streams to facilitate the interchange of information between digital imaging computer systems in medical environments.

The DICOM File Meta Information includes identifying information on the encapsulated DICOM Data Set. The DICOM Standard requires that a file header of identifying information be present in every DICOM file. The DICOM file header consisting of a 128-byte File preamble, followed by a 4-byte DICOM prefix, followed by the File Meta Elements. This means, for example, that a DICOM file of a chest x-ray image actually contains the patient identification within the file, so that the image can never be separated from patient information by mistake. A DICOM file contains both the image and a large amount of patient information about whom, where, and how the image was acquired, known in the arts as patient metadata.

However, DICOM files often contain little information about the content of the imagery or meaning of the imagery pixels, the encapsulated waveform data used for audio clinical notes, or the encapsulated structured reports used for clinical documents, all of which are used for clinical detection, diagnosis and treatment of disease. This network system improves upon and applies in a collaborative environment which provides for capture, retrieval and concurrent viewing of both live and archived medical imagery streams for communication, collaboration and consultation with one or more sources of streaming imagery data by one or more users, also known as participant cognitive collaborants. Collaborated medical imagery streams comprise one or more sources of streaming imagery data, including DICOM imagery files. As used herein, DICOM imagery files include modality information objects, (e.g., streaming video), waveform information objects (e.g., voice audio, echocardiogram), and structured report document information objects (e.g., clinical documents), as specified in PS 3.3 Part 3: Information Object Definitions of the DICOM Standard.

Medical imagery streams include DICOM imagery files. This network system allows for each user to collaborate simultaneously with all users viewing every other users' work product, as the work product is being created, all coincident with one or more streams of streaming imagery data wherein each server manages streams of medical imagery together with participant cognitive collaborant input illustrations for use with DICOM imagery files. The network system provides live video and audio communication, as well as a method of viewing, recording and transmitting streaming imagery data, which include DICOM imagery files, in DICOM format, which requires a single file format structure. Streaming imagery data includes both live and archived imagery data. As used herein, multi-channel streaming imagery data is defined as a collection of one or more sources of streaming imagery data each of which comprise at least one image frame that defines a time progression of output from various sources, which include video, encapsulated waveform data, and encapsulated structured reports.

The network system provides multi-channel multiplexed capability for capture, retrieval and concurrent viewing of both live and archived medical imagery streams for communications, collaboration, consultation and instruction with one or more sources of streaming imagery data by participant cognitive collaborants. Participant cognitive collaborant input illustrations as defined herein include, but are not limited to telestrations, drawings, sketches, text annotations, including letter character text and numeric character text, image annotations, wave form annotations, voice annotations, video annotations, augmented reality imagery annotations, 3D/4D imagery annotations, outcomes annotations, costs annotations, resource consumption/utilization annotations, haptic annotations, patient metadata, imagery metadata, semantic metadata and annotations, appended patient metadata, appended imagery metadata and appended semantic metadata and annotations. The network system appends participant cognitive collaborant input illustrations to streaming imagery data, and encapsulates and saves those input illustrations, together with streaming imagery data, and relevant imagery metadata and semantic metadata and annotations, including appended imagery metadata and appended semantic metadata and annotations, from the collaboration session in single file format structures, known as collaborated imagery files. The 'single file encapsulate and save' functionality of the network system encapsulates and saves collaborated imagery files in single file format structures, as may be required or allowed by standards for clinical documentation or medical records storage, including those as specified in the DICOM Standard (e.g., as DICOM files).

The network system appends metadata tags to participant cognitive collaborant input illustrations and encapsulates and saves those tagged input illustrations together with the Data Set from the streaming imagery data and relevant metadata information from the metadata header in single file format structures for use within a DICOM imagery environment, including those as specified in the DICOM Standard. The network system appends metadata tags to alpha-numeric text annotations, image annotations, wave form annotations, voice annotations, video annotations, augmented reality imagery annotations, 3D/4D imagery annotations, outcomes annotations, costs annotations, resource consumption/utilization annotations, haptic annotations and clinical documents and encapsulates those alpha-numeric text annotations, image annotations, wave form annotations, voice annotations, video annotations, augmented reality imagery annotations, 3D/4D imagery annotations, outcomes annotations, costs annotations, resource consumption/utilization annotations, haptic annotations and clinical documents and saves those as DICOM files. The network system can also append annotation files encapsulated as DICOM files to the Data Set for streaming imagery data, and encapsulate them together with relevant metadata information from the metadata header for streaming imagery data, and save in single file format structures as collaborated imagery files (CIF).

Collaborated imagery files, also known as CIFs, conform to the DICOM Standard and can be stored, archived, queried, and retrieved as DICOM files. CIFs can be stored locally in media libraries and later retrieved for subsequent use in collaboration sessions. CIFs conform to the DICOM Standard [3.10] and can be encrypted and/or transmitted over networks for remote viewing, communication and collaboration. CIFs conform to specifications of the DICOM Standard for secure encapsulation of DICOM objects in a clinical document architecture (CDA). As such CIFs can be stored as in archives conforming to health level seven (HL7), integrating the healthcare enterprise (IHE), cross-enterprise document sharing (XDS), cross-enterprise document sharing for imaging (XDS-I), Extensible Markup Language (XML), in Tagged Image file format (TIFF), as well as in RDF triples and RDF/XML for metadata model specification.

CIF's can also contain encapsulated and saved haptic imagery and annotations in COLLADA-compliant .dae files. COLLADA (collaborative design activity) is an interchange file format for interactive 3D applications that has been adopted by ISO as a publicly available specification, ISO/PAS 17506. COLLADA defines an open standard XML schema for exchanging digital assets among various graphics software applications that might otherwise store their assets in incompatible file formats. COLLADA documents that describe digital assets are XML files, usually identified with a .dae (digital asset exchange) filename extension.

CIFs conform to specifications of the DICOM Standard for encapsulation of audio with imagery data sets. CIFs conform to specifications to the DICOM Standard for DICOM structured reporting. CIFs can be viewed as stand-alone medical imagery, or embedded into other CIFs as video, audio and haptic annotations. The network system can create collaborated imagery studies, also known as CIS's, which include one or more collaborated imagery files, encapsulated and saved in single file format structures, as may be required or allowed by standards for clinical documentation or medical records storage, including those as specified in the DICOM Standard format. Collaborated Imagery Studies, also known as 'Clini-DOCx' are visual story boards can be used for capture, display, file exchange, publication and distribution of collections of clinical cognitive vismemes.

The DICOM Standard defines the characteristics of a medical study performed on a patient as, "a collection of one or more series of medical images, presentation states, SR documents, overlays and/or curves that are logically related for the purpose of diagnosing a patient. Each study is associated with exactly one patient" (PS 3.3 A.1.2.2 STUDY IE). Streaming imagery data can include both collaborated imagery files and collaborated imagery studies. Both CIFs and Clini-DOCx can be incorporated into medical image streams of live or archived streaming imagery data for use during synchronous or asynchronous collaboration sessions.

The traditional way of capturing an image from a medical imaging device commonly called a modality, generally consisted of an operator or technician first conducting a scan. Then, using the modality to save the image, in still or motion video format, into the modality memory or into a main image storage database. The next step in the process typically involved downloading the image into a hospital database, known in the arts as a Picture Archiving and Communications System, hereinafter referred to as PACS or PACS server. PACS is a medical imaging technology which provides economical storage of, and convenient access to, images from multiple modalities (source machine types). Electronic images, including patient information known in the arts as patient metadata, are transmitted digitally to and from PACS, eliminating the need to manually file, retrieve or transport film jackets. The universal form of PACS image file storage and transfer is the DICOM Standard, and is well known in the arts. PACS can be further defined by a storage and management system for medical images.

In the medical field, images such as x-rays, MRI's and CAT scans typically require a greater amount of storage than other images in other industries. A clinician would access the PACS system to retrieve the image, view and review the image, and conceivably develop a diagnosis based on the information from the image. This system imagery is viewed by a user and diagnosis made without image delay and the user accomplishes all these tasks live. "Live" referring to events simulated by a computer at the same speed that they would normally occur in real life. In graphics animation, for example, a live program (such as this inventor's system) would display objects moving across the display at the same time they would actually move, or in the case of this invention, a cognitive collaborant views the image live and collaborates from cognitive collaborant to cognitive collaborant with no perceivable delay to any of them.

The inventor has developed a novel and simple network system and methods of using the same, to allow a group of cognitive collaborants to concurrently collaborate on a computer system, with each participant cognitive collaborant viewing each other's telestrations, drawings, and annotations and saving them together with streaming imagery data, annotations and relevant imagery metadata, including appended imagery metadata and semantic metadata and annotations, and saving them together in single file format structures as may be required or allowed by standards for clinical documentation or biomedical records storage, including those as specified in DICOM, C-CDA and FHIR Standards for interoperable health information exchange.

SUMMARY

A network system and methods for using the same for concurrent collaboration between users, collaborating by a variety of input illustrations, which include video, audio, telestrations, drawings and annotations, as well as collaborating on medical images that are typically accessed on a storage server database, imaging archives, or continuous streaming video.

The invention relates generally to a multimedia collaborative conferencing system and methods of using the same for generating input illustrations, which include telestrations, drawings and annotations on medical images concurrently with other users and saving participant cognitive collaborant input illustrations with streaming imagery data, annotations and relevant imagery metadata, including appended imagery metadata in single file format structures, including those as specified in the DICOM Standard. Applicant's network system is known as the TIMS Clinical Network System. It is comprised of three essential components: one called TIMS Clini-Pod Network Servers (CNS); another called TIMS Clini-Ports; and a third called TIMS Clini-Docks, as depicted in FIG. 1. A Tele-Visual Imagery Informatics Management System is hereinafter referred to as TIMS. TIMS Clini-Pod Network Servers (CNS) are computers that manage users, security, authentication, authorization, image streams, channels and sessions within the TIMS Clinical Network System (i.e. the invention described herein) that allows for multiple users in multiple locations to concurrently collaborate on the images, each user to input highlighted graphic electronic traces and annotations over the medical image, encapsulate and single file save each and all input illustrations from participant cognitive collaborants, which include telestrations, drawings, and annotations together with streaming imagery data, annotations and relevant imagery metadata, including appended imagery metadata and semantic metadata and annotations, from collaboration sessions in single file format structures, known as collaborated imagery files, as may be required or allowed by standards for clinical documentation or medical records storage, including those as specified in the DICOM Standard. DICOM compliant files must contain both imagery data sets and metadata information.

TIMS Clini-Docks include a medical image acquisition system adapted for receiving and transmitting medical images, constructed from, a computer having communications capability adapted for acquisition and transmission of a plurality of medical imaging and video signals. Wherein the medical image and video signals are acquired at the medical device's native resolutions, transmitting the signals at their native resolutions and native frame rates to a receiving device, receiving the medical imaging video signals in analog or digital form, and if required, compressing and scaling the signal, converting the signal to digital form for transmission, and transmitting the digital signals using secure encryption protocols to a display device. TIMS Clini-Docks are capable of concurrently acquiring signals from a plurality of medical imaging systems, as depicted in FIG. 1, including but not limited to, ultrasound, Computer Tomography (CT) scan, fluoroscopy, endoscopy, magnetic resonance imaging, nuclear medicine, echocardiogram ultrasound and microscopy. Medical imaging equipment is also referred to as modalities. A more complete list of sources for DICOM imagery streams can be found in the DICOM Standard [PS 3.3 Part 3: Information Object definitions], which include video (imaging), audio (waveform), and clinical documents (structured reports).

TIMS Clini-Docks can also receive the video image signal from a plurality of video sources, including but not limited to, S-video, composite color and monochrome, component red blue green video (RGB, three additive primary colors), Digital Visual Interface (DVI), any video transport protocol including digital and analog protocols, high definition multimedia interface (HDMI, compact audio video interface uncompressed digital data), serial digital interface (SDI), and DICOM video in their native, enhanced or reduced resolutions or their native, enhanced or reduced frame rates. The component, known in this invention as TIMS Clini-Pod Network Servers (CNS), manage communications between all acquisition systems (TIMS Clini-Docks), between all TIMS Clini-Ports, the computer workstations used by cognitive collaborants during collaboration sessions, between hospital servers, located on site or remotely, that store hospital images, and hospital networks in both local area and wide area configurations.

TIMS Clini-Pod Network Servers (CNS) manage both live and archived streaming imagery data acquired from TIMS Clini-Docks, and archived imagery, including collaborated imagery files, retrieved in predetermined digital single file format structures, including those as specified in DICOM Standard, and stored locally in media libraries on participant cognitive collaborants computer storage devices, in image data repositories on tele-visual imagery informatics management system servers, in image data repositories on cloud storage devices and locations, in image data repositories on picture archiving and communications system repositories, on other image data repositories compliant with standards for digital imaging and communications in medicine, or on any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

A participant or user computer can be defined as typically made of several components such as a main circuit board assembly having a central processing unit, memory storage to store programs and files, other storage devices such as hard drives, and portable memory storage, a power supply, a sound and video circuit board assembly, a display, and an input device such as a keyboard, mouse, stylus pen and the like allowing control of the computer graphics user interface display, where any two or more of such components may be physically integrated or may be separate. In one depiction, a remote location communicates with the networked computer, for the purpose of collaborating and conferencing with medical streaming imagery data.

TIMS Servers (CNS) manage the master control functionality of the TIMS Clinical Network System. This functionality is achieved via the connection of TIMS Servers (CNS) to TIMS Clini-Docks and allows multiple users in multiple locations to view live all telestrations, and annotations from each of the users during collaboration sessions, as depicted in FIG. 1. Telestrations and annotations are added as appended layers over the source video and do not alter the source imagery. In addition, when multiple TIMS Clini-Docks are connected to multiple medical modalities, as shown in FIG. 1, TIMS Clini-Pod Network Servers (CNS) enable concurrent collaboration with each and all of these multiple sources of streaming imagery data. TIMS Clini-Pod Network Servers (CNS) dynamically control which of the multiple sources of streaming imagery data each TIMS Clini-Port wishes to view, as depicted in FIG. 3.

TIMS Clini-Pod Network Servers (CNS) are typically deployed in several configurations: Clini-Pod or pairs, typically 1-2 Clini-Pods (hub-and-spoke or peer-to-peer); Clini-Pod Quads, or teams [typically 2-4 Clini-Pods); Clini-Pod Squads, (typically four Quads, or 16 Pods) and Clini-Pod Hives [4 Clini-Pod Squads]. Local CNS network servers connect individual cognitive collaborants, also known as pod team members to devices in their Clini-Pod, as depicted in FIG. 13. Team CNS network servers interconnect four Clini-Pods each other to allow for four-party tele-visual communication and live synchronous collaboration with shared work products, as depicted in FIG. 14. Hive CNS network servers connect four or more team network servers as depicted in FIG. 15. TIMS Clini-Pod Network Servers can be deployed in point-to-point, hub-and-spoke and mesh chord networks, as depicted in FIG. 16, as well as in other network configurations described in the Bellcore Telecommunications Management Network [TMN] architecture. In particular, TIMS Clini-Pod Network Servers can be deployed in core-spine-leaf network topologies, as depicted in FIG. 17, as well as in 2-tier, 3-tier or N-tier application architectures, as depicted in FIG. 18.

TIMS Clini-Port software applications allow participant cognitive collaborants to add other sources of streaming imagery data by selecting the "add+" channel selection tab, and viewed on the channel tabs of the multi stream viewer as shown in FIG. 3, (channel 1X . . . ).

The multi-channel stream view capability of TIMS Clini-Port software applications allow concurrent viewing of multiple channels of both live and archived medical imagery streams as depicted in FIG. 7. The multi-channel stream view selection capability is depicted in FIG. 9, and again in FIG. 10 with multiple channels of both live ("stream") and archived (image "81420095249.jpg, and image "99200982617.mpg") medical imagery streams selected for capture, retrieval and concurrent viewing during a collaboration session. TIMS Clini-Port software applications include DICOM view capability, which allows participant cognitive collaborants to view, communicate, collaborate, consult and instruct with DICOM imagery streams. TIMS Clini-Port software applications include capabilities to view non-DICOM imagery as well, which allows participant cognitive collaborants to view, communicate, collaborate, consult and instruct with non-DICOM imagery streams. The multi-channel stream view capability of TIMS Clini-Port software applications allows participant cognitive collaborants to capture, retrieve and concurrently view both live and archived medical imagery streams for communication, collaboration, consultation and instruction with one or more sources of streaming imagery data by one or more participant cognitive collaborants, with both DICOM and non-DICOM imagery streams during collaboration sessions. Each participant cognitive collaborant, some of whom may be located remotely to the imaging modalities, is able to view, analyze, discuss and comment on each of the input illustrations from participant cognitive collaborants concurrently, live, and save such analysis or discussion as may be clinically relevant.

In one embodiment, the connection of TIMS Clini-Pod Network Servers (CNS) to TIMS Clini-Docks allows TIMS Clini-Ports to customize preferences for capture, retrieval, and viewing of streaming imagery data while the patient is still on the examination table. TIMS Clini-Ports can have direct access and control of the streaming imagery data and maintain the native resolution and frame rate output from the medical modality. If desired, TIMS Clini-Ports can adjust the native resolution, frame rate, and compression of the streaming imagery data specific to the user's preferences. In addition, TIMS Clini-Ports are able to live instruct clinicians who are controlling streaming imagery data at their respective modality sources, and view the results of those instructions to ensure that imagery acquired is consistent with user preferences, as depicted in FIG. 3. Those instructions are conveyed via two-way communication between user and clinician with voice, text, video or telestrations within the TIMS Clini-Pod Network System and are not reliant upon any external communications network.

Without access to master control of TIMS Clini-Docks by TIMS Clini-Pod Network Servers (CNS), imagery viewed by a remote client using another invention is limited to the quality of the view and capture settings specified by others, which may be different than those desired or required by the remote client. TIMS Clini-Docks are multichannel streamer stacks that allow live capture and archived retrieval for tele-visual communications with: (1) streaming video; (2) medical imagery modalities and waveforms; (3) electronic medical records; and (4) clinical and multiomic maps and biometric data stream visualizations.

As used herein, "streaming medical imagery" includes all information objects described in the DICOM Standard, including images, video, modality imaging and waveforms—audio, visual and haptic wave forms and files, medical records and clinical documents, multiomic-phenotypic, genomic, metabolomic, pathomic, radiomic, radiopathomic and radiogenomic—maps and clinical data sets, including those as described in the Institute of Medicine's Towards Precision Medicine—A New Taxonomy of Disease; along with biometric data stream visualizations from connected medical devices, signals and sensors used for local and remote patient monitoring.

In one embodiment TIMS Clini-Docks can be deployed in four (4) dual channel streamer stacks to accommodate both live and archived streaming imagery data from these four principal modalities for tele-visual communications and collaboration with imagery informatics. Clini-Dock streamer Channel (1) is typically reserved for video communications and conferencing among team members and other cognitive collaborants. Channel (2) normally designated for electronic medical records and patient monitoring; Channel (3) for medical imaging modalities and wave forms. Channel (4) for data mapping and interactive biometric data stream visualizations, including virtual reality and augmented reality displays. The TIMS Clini-Port typically has one or more multi-channel monitors for connected devices, which can be situated locally, within the Clini-Pod, or at remote locations, including other Clini-Pods.

TIMS Clini-Docks, due to its novel capabilities, can acquire analog or digital video signals, standard or non-standard video resolutions, medical or non-medical imagery, live or archived imagery, and compressed or uncompressed imagery formats. TIMS Clini-Docks converts analog sources of streaming imagery data, as well as non-standard sources of streaming imagery data into digital imagery data sets for use by participant cognitive collaborants during collaboration sessions. TIMS Clini-Docks can also convert non DICOM digital imagery data sets, including non DICOM modality imaging (e.g. video), waveform data (e.g. voice, audio, haptic), and structured reports (DICOM-SR from PACS) and clinical documents (CCD, CCR from EHR medical records systems) into DICOM imagery streams for use by participant cognitive collaborants during collaboration sessions. The TIMS Clini-Dock stack depicted in FIG. 1 allows for capture of multiple sources of streaming imagery data in any and all combinations of the preceding specifications, (e.g., both DICOM and non-DICOM imagery streams, standard and non-standard imagery streams, and compressed and uncompressed imagery streams) and allows TIMS Clini-Ports concurrent viewing of multiple sources of streaming imagery data. TIMS Clini-Docks incorporate approved medical device components that processes any video output from a video source into an image stream, including but not limited to streaming imagery data from medical modalities, as depicted in FIG. 1.

TIMS Clini-Docks are connected directly to multiple sources of streaming imagery data, as depicted in FIG. 1, and continuously streams images to TIMS Clini-Pod Network Servers (CNS). Any number of TIMS Clini-Ports can request information from a TIMS Clini-Pod Network Servers (CNS). Each TIMS Clini-Port in a conference with another or other TIMS Clini-Ports can view all the TIMS Clini-Port object inputs as they occur. TIMS Clini-Ports refer to computer workstations used by cognitive collaborants during collaboration sessions, typically for medical review and diagnosis of patient image data.

TIMS Clini-Pod Network Servers (CNS) keep track of all TIMS Clini-Docks that have image streams available and displays a list of image streams available TIMS Clini-Ports, as depicted in FIG. 3. TIMS Clini-Pod Network Servers (CNS) communicate with image repositories, including but not limited to PACS system repositories, and store information on all TIMS Clini-Ports' computers live. TIMS Clini-Pod Network Servers (CNS) include software components that manage streaming requests to TIMS Clini-Docks; manage authentication and authorization tasks for access and privileges; manages users information, roles, session logs and, configurations for TIMS Clini-Pod Network Servers (CNS) and TIMS Clini-Docks; manage web services interactions with TIMS Clini-Ports; send, query and retrieve collections of one or more streaming imagery data files, including collaborated imagery files, also known as studies, to and from image repositories, as depicted in FIGS. 10 and 11, including but not limited to DICOM compliant image repositories, e.g., PACS; specify unique combinations of image quality, resolution, compression and frame rates as may be required for each collaboration session, as depicted in FIG. 3; access patient information from a DICOM Modality Worklist utility (DMWL); collaborated imagery files, to TIMS Clini-Ports; manage text chat information; manage DICOM send services, wherein the DICOM send service sends the annotated images to PACS or DICOM compliant image repositories, also known as medical image archives, as depicted in FIG. 10; allow for query and retrieve functionality that retrieves lists of DICOM studies from PACS servers and DICOM compliant image repositories and sends those studies to TIMS Clini-Ports.

A DICOM study is defined as a collection of one or more medical images and patient data combined in single file format structures, including those as specified in the DICOM Standard. DICOM Modality Worklist is defined as a software utility that invokes DICOM query and retrieve functionality which enables imaging equipment (e.g., medical modalities) to query medical image stores, including but not limited to PACS, and obtains details of patient and scheduled examinations electronically, including patient demographics and study data, avoiding the need to type patient information multiple times, as depicted in FIG. 10. Clini-Pods typically deploy with Clini-CDR (Clinical Data Repositories, consisting of p-CKR [personalized Clinical Knowledge Repositories] with local storage of CIFs and clinical cognitive vismemes in personalized clinical knowledge repositories, clinical cognitive vismeme vaults; and metadata repositories which house reference links to collaborated imagery files, along with dicomized cognitive collaboration security tokens which provide granular control over access to shared imagery files stored in clinical data repositories, personalized clinical knowledge repositories, clinical cognitive vismeme vaults and metadata repositories.

Security tokens for cognitive collaboration, selectively providing access to imagery information objects, their associated metadata and annotations, including personal health information (PHI), can be created, read, updated or deleted, with concurrence by or among one or more participant cognitive collaborants, before, during or after cognitive collaboration s sessions. Security tokens for cognitive collaboration can be maintained in separate metadata repositories, including blockchain metadata repositories and blockchain data ledgers, and accessed by cognitive collaborants with appropriate security privileges.

TIMS Clini-Pod Network Servers (CNS) also manage all the participant cognitive collaborant input illustrations, specifically, the entire participant cognitive collaborant input illustrations, sketches, drawings, telestrations and annotations. Participant cognitive collaborant input illustrations as previously defined herein include, but are not limited to telestrations, drawings, sketches, text annotations, including letter character text and numeric character text, image annotations, wave form annotations, voice annotations, video annotations, augmented reality imagery annotations, 3D/4D imagery annotations, outcomes annotations, costs annotations, resource consumption/utilization annotations, haptic annotations, imagery metadata and appended imagery metadata, as depicted in FIG. 7. All participant cognitive collaborant input illustrations are managed by TIMS Clini-Pod Network Servers (CNS) based on a file sharing scheme where new input illustrations keep getting appended to files on TIMS Clini-Pod Network Servers (CNS). TIMS Clini-Pod Network Servers (CNS) distribute copies of streaming imagery data to each of the participant cognitive collaborants. Since participant cognitive collaborants collaborate only with copies of images, they do not alter the original streaming imagery data in any way. This approach of generating input illustrations on TIMS Clini-Pod Network Servers (CNS), and distributing only those input illustrations and not the underlying images to each participant cognitive collaborant, significantly improves operating performance and reduces image latency and wait times. That method of moving images with illustrations back and forth from a computer to a server, results in losing illustration quality or consuming more bandwidth. However, with this novel invention, the process of multi-layer multi user input illustrations on any underlying images, including streaming imagery data, and updating and appending on the streaming imagery data with multiparty annotations and metadata without sacrificing network bandwidth, is novel to this invention.

TIMS Clini-Pod Network Servers (CNS) allow TIMS Clini-Ports to create collaborated imagery files synchronously or asynchronously. TIMS Clini-Pod Network Servers (CNS) use a process of local registration to identify the image frames needed for viewing on each of the participant cognitive collaborant computers, and sends to each of them only the image frames necessary for participation in a collaboration session. TIMS Clini-Pod Network Servers (CNS) enable each participant cognitive collaborant to use a scalable window so all input illustrations for each and every participant cognitive collaborant are dynamically ratio metric based on the underlying image aspect ratio of the respective participant cognitive collaborant computer. Therefore, all the input illustrations always point to the part of the window and image as originally intended, regardless of window size on the clients computer display. A central frame counter originating in the participant cognitive collaborant computer, which has play/pause control, issues frame synchronization commands to synchronize the image streams on all participant cognitive collaborants' computers. This method significantly reduces bandwidth requirements and improves responsiveness of system updates and imagery appends. Each client computer which has play/pause control also sends synchronizing commands whenever its displayed images are paused. This ensures that the same frame is available to all participating clients by broadcasting that pause frame number along with the pause command to all participating clients.

Client participants can receive video streams directly from TIMS Clini-Docks using a local area network. The invention can also detect if a user has low bandwidth, in transmission, or in reception, or in both and can compensate by only sending selected image frames to that user. For example, with low bandwidth TIMS Clini-Pod Network Servers (CNS) can send every third, fifth, or Nth frame of a collaborated imagery to clients so that client does not have any perceptible delay. Remote client participants using the internet must receive all imagery from TIMS Clini-Pod Network Servers (CNS) for secure transmission, rather than directly from local TIMS Clini-Docks, to ensure streaming imagery data is not transmitted over the internet without encryption.

TIMS Clini-Ports, also known as participant cognitive collaborants, can take several roles. Each participant cognitive collaborant can capture, retrieve and concurrently view both live and archived streaming imagery data of their own choosing, including medical imagery streams selected for the collaboration session; capture, retrieve and concurrently view both live and archived streaming imagery data streams selected by other participant cognitive collaborants, including medical imagery selected for the collaboration session; each participant cognitive collaborant can add multiple sources of streaming imagery data, also referred to as multiple channels, of both live and archived streaming imagery data for other participant cognitive collaborants to capture, retrieve and concurrently view; capture, retrieve and concurrently view multiple sources of both live and archived streaming imagery data, including medical imagery streams selected for a collaboration session; concurrently add input illustrations on both live and archived streaming imagery data; taking on any and all of the above roles dynamically, as depicted in FIG. 4.

In addition, TIMS Clini-Port software applications are collaborative, interactive tools for synchronous or asynchronous media annotation, which can be used with medical files to enable participant cognitive collaborants to communicate, collaborate, consult and instruct with medical images for clinical review and discussions and deciding on relevant medical procedures.

This novel invention—combination streamer-splitter-server-router-network gateway servers—allows any of the TIMS Clini-Ports to host a collaboration session with any other TIMS Clini-Port, in various network configurations, including peer-to-peer, hub-and-spoke, mesh chord networks, as depicted in FIG. 16. A collaboration session host selects any number of participant cognitive collaborants from their contact list, as depicted in FIG. 5, and sends a request to those clients with whom they wish to collaborate. Each participant cognitive collaborant receiving the request can elect to join or decline the session by selecting the appropriate button on the dialog box that appears on their computer monitor, as depicted in FIG. 6. Upon acceptance of the request, the cognitive collaborant client's monitor is automatically switched to view the same imagery as the collaboration session host. The host can select live streaming imagery data from any of the available TIMS Clini-Docks, as depicted in FIG. 3, can also select from any archived streaming imagery data available through the query and retrieve functions, as depicted in FIG. 11, and concurrently collaborate using all selected imagery data streams—live, archived or both—for multimodal clinical communications, collaboration, consultation or instruction with all participant cognitive collaborant clients during the collaboration session.

All input illustrations added by participant cognitive collaborants are concurrently visible to all of the other participant cognitive collaborants. In addition, each participant cognitive collaborant can add input illustrations, which include telestrations, drawings, text annotations, image annotations, wave form annotations, voice annotations, video annotations, augmented reality imagery annotations, 3D/4D imagery annotations, outcomes annotations, costs annotations, resource consumption/utilization annotations, haptic annotations, to streaming imagery data, together with relevant imagery metadata, including appended imagery metadata and semantic metadata and annotations. Furthermore, each participant cognitive collaborant client can also use the TIMS Clini-Pod Network System to chat with each other during a collaboration session using a text chat facility. A separate text window box is displayed that allows for each participant cognitive collaborant to instant message each other in text format and include those images as input illustrations, as depicted in FIG. 7. One feature of this invention is that the host can disable the edit control of any client, such that a particular client will not be able to add or edit the annotations or telestrations, as depicted in FIG. 8. At this point, the client can only view the annotations made by others. The host can also pass the control of the video stream start/stop/pause functions to another client. This control allows the host to enable or disable the functionality to all clients or selected clients and can be done at any time during the collaboration session. At the conclusion of the session, participant cognitive collaborants can encapsulate and save all input illustrations, which include telestrations, drawings and annotations together with streaming imagery data, and relevant imagery metadata, including appended imagery metadata and semantic metadata and annotations, from the collaboration session, in single file format structures, known as collaborated imagery files. Collaborated Imagery Files are encapsulated and saved in single file format structures, as may be required or allowed by standards for clinical documentation or medical records storage, including those as specified in the DICOM Standard (e.g., as DICOM files). Participant cognitive collaborant clients can send collaborated imagery files to any PACS or DICOM compliant image data repository, or send to any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations. A session log is recorded and saved on the TIMS server, as depicted in FIG. 9.

The invention also works with wearable signals, sensors, devices and monitors, collectively "mobile computing", also known as Personal Digital Assistants. Participants (PDA) clients can use these PDAs to view, consult and collaborate on DICOM images. Personal digital assistant is any small mobile handheld device that provides computing and information storage such as handheld computers, phones, media display devices and handheld computers, including watches and vison.

The invention enables both synchronous and asynchronous multimodal clinical communications, collaboration, consultation and instruction between and among participant cognitive collaborants, including heterogeneous networked teams of persons, machines, devices, neural networks, robots and algorithms. And specifically, the invention enables multimodal clinical communications, collaboration, consultation and instruction during various stages of medical disease and injury management, including detection, diagnosis, prognosis, treatment, measurement, monitoring and reporting, as well as workflow optimization with operational analytics for outcomes, performance, results, resource utilization, resource consumption and costs.

In one embodiment the invention provides for a unique streamer-splitter-server-router functional combination in a single network edge device, a neurosynaptic network node, having bi-directional communications capability with other Pod network gateway servers via network, video and wireless connectivity. Network gateway servers—neurosynaptic network nodes—can be combined in various multichannel multiplexed combinations, including pod pairs (2), pod quads (4), pod squads (16), and pod hive clusters (64), as depicted in FIGS. 13, 14 and 15. Neurosynaptic network servers can be deployed in various network architectures, including point-to-point (peer-to-peer), hub-and-spoke, and mesh chords, as depicted in FIG. 16. Neurosynaptic network servers can be deployed can be deployed in core-spine-leaf network topologies, as depicted in FIG. 17, as well as in 2-tier, 3-tier or N-tier application architectures, as depicted in FIG. 18. These embodiments allow for dynamic neurosynaptic connectivity for multichannel multiplexed networked visual communications.

In another embodiment the invention provides a method for recursive cognitive enrichment and collaborative knowledge exchange between and among cognitive collaborants, including heterogeneous networked teams of persons, machines, devices, neural networks, robots and algorithms. Specifically, it provides neurosynaptic network connectivity enabling both synchronous and asynchronous multimodal clinical communications, collaboration, consultation, instruction, that includes viewing, curating, annotating and tagging, using one or more sources of multichannel, multiplexed heterogeneous streaming imagery data, including both medical and non-medical streaming imagery data.

This embodiment also provides a method for rapid, adaptive deep learning and specialist skills acquisition by and among cognitive collaborants, including heterogeneous networked teams of persons, machines, devices, neural networks robots and algorithms, with neurosynaptic network connectivity enabling both synchronous and asynchronous multimodal clinical communications, collaboration, consultation, instruction, that includes viewing, curating, annotating and tagging, using one or more sources of multichannel, multiplexed heterogeneous streaming imagery data, including both medical and non-medical streaming imagery data, together with images, video, modality imagery, waveforms, audio and haptic files, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

A medical imagery stream is defined as a collection of one or more sources of streaming imagery data which comprise at least one image frame that defines a time progression of output from a video source. TIMS Clini-Docks maintain image quality from source modalities as required for conformance to DICOM Standards for clinical use. TIMS Clini-Docks specify streamer components that have secured regulatory clearances for transmission and viewing of medical imagery streams for clinical diagnostic purposes.

In one embodiment, TIMS Clini-Pod Network Servers (CNS) provide live video and audio communications, as well as a method of recording, transmitting and saving images in single file format structures, including those as specified in the DICOM Standard. DICOM is a medical imaging standard common in the medical industry. DICOM can also be defined as a standard in the field of medical informatics for exchanging digital information between medical imaging equipment (such as radiological imaging) and ensuring interoperability with other systems. DICOM, including protocols for device communication over a network, syntax and semantics for commands and associated information that can be exchanged using protocols, a set of storage services and devices claiming conformation to the standard, as well as file format and medical directory structures to facilitate access to images and related information stored on media that shares information. The embodiment can serve as the connection point between any medical imaging modality and a hospital PACS, medical archive or other image repository, including clinical data repositories, personalized clinical knowledge repositories, clinical cognitive vismeme vaults and metadata repositories.

One component of this invention, TIMS Clini-Pod Network Servers (CNS), are able to connect DICOM equipment and older non-DICOM equipment to a hospital network, allowing imaging studies to be stored and saved. The TIMS Clini-Pod Network System, this invention described herein, briefly described as a trace overlay and annotation system that users can collaborate with each other live, each viewing each other's object inputs and those object inputs can be encapsulated and saved in single file format structures, including those as specified in the DICOM Standard, in PACS, in a DICOM compliant image archives, or in other image repositories.

Another embodiment the TIMS Clini-Pod CNS network system can be deployed as collaboration portals for multi-party cognitive collaboration among specialist providers; care coordination for caregiving teams both local and remote; and patient provider engagement, the support of meaningful use goals and objectives for electronic medical records. Clini-Pod CNS also support health information exchange for integrated delivery systems; for biomedical, clinical and genomic mapping and multisensory data stream visualizations, as well as clinical decision support for value care-giving teams.

Still other embodiments provide networked informatics connectivity for medical kiosks, offices and retail clinics, ambulatory care and nursing facilities. Often these facilities have limited connectivity for access to hospital-based electronic medical systems. In those circumstances the TIMS Clini-Pod CNS as "LAND" [Local Adapter for Network Distribution] and "SEE" [Surrogate Electronic Health Record Environment] to facilitate health information exchange with hospitals and other caregiving facilities. Use of TIMS Clini-Pod access and enable groups with access to EHR systems to share electronic medical information with those who do not, and specifically by health information exchange with Consolidated Clinical Document Architecture (C-CDA") compliant documents, including Continuity of Care Documents (CCD, CCD+, etc.), Fast Healthcare Interoperability Resources ("FHIR") and Universal Transfer Forms (UTF.)

BRIEF DESCRIPTION OF DRAWINGS

Other objects, features, and advantages will occur to those skilled in the art from the following description of an embodiment and the accompanying drawings, in which:

FIG. 1, depicts a block diagram of the invention.

FIG. 2, depicts a block diagram of a portion of the system.

FIG. 3, depicts a graphic user interface screen shot of a cognitive collaborant workstation: client imagery source selection display.

FIG. 4, depicts a graphic user interface screen shot of cognitive collaborant workstation: client source imagery with illustration tool bar and collaboration function.

FIG. 5, depicts a graphic user interface screen shot of a cognitive collaborant workstation: client selecting participant cognitive collaborants for collaboration session.

FIG. 6, depicts a graphic user interface screen shot of cognitive collaboration session initiation.

FIG. 7, depicts a graphic user interface screen shot of a cognitive collaboration session, including streaming medical imagery with annotations.

FIG. 8, depicts a graphic user interface screen shot of a cognitive collaborant workstation: client assignment of control to participant cognitive collaborant.

FIG. 9, depicts a graphic user interface screen shot list of multiple cognitive collaboration sessions.

FIG. 10, depicts a graphic user interface screen shot of patient image study information.

FIG. 11, depicts a graphic user interface screen shot of patient electronic medical record information.

FIG. 12, depicts a graphic user interface screen shot of administrative controls.

FIG. 13, depicts deployment of a hub-and-spoke device cluster for either server-based or peer-to-peer networks.

FIG. 14, depicts a 4-Party Team Network Server cluster interconnecting with four Clini-Pod hub-and-spoke device clusters.

FIG. 15, depicts a 4-Party Hive Network Server cluster interconnecting with four Team Network Server clusters.

FIG. 16, depicts Alternative Network Architectures for Clini-Pod deployment: point-to-point vs hub-and-spoke vs chord.

FIG. 17, depicts traditional 3-Tier Application Architectures versus Core-Spine-Leaf Network Topology.

FIG. 18, depicts traditional 1-Tier, 2-Tier, 3-Tier and N-Tier Application Architectures.

FIG. 19, depicts Value Chain Knowledge Exchange.

FIG. 20, depicts processes for generating insights from Knowledge Mapping and Interactive Data Visualization (data analytics, aggregation and contextualization).

FIG. 21, depicts transforming Data into Information, then into Knowledge, Wisdom, Decision and Action.

FIG. 22, depicts Information Optimization through Descriptive, Diagnostic, Predictive and Prescriptive Analytics.

FIG. 23, depicts Cognitive Value Creation with Information Optimization and Advanced Data Analytics.

FIG. 24, depicts Adaptive Systems Learning with Augmented Analytics.

FIG. 25, depicts increasing Business Intelligence and Actionable Information with semantic metadata and annotation.

FIG. 26, depicts domain-specific semantic search, ontology mapping and visualization with RDF metadata.

FIG. 27, depicts semantic interoperability with metadata registries and information model annotation.

FIG. 28, depicts a semantic data lake for clinical, financial and outcomes data integration.

FIG. 29, depicts building semantic data trails with metadata extraction from structured, semi-structured and unstructured data, including biomedical data from medical imaging modalities.

FIG. 30, depicts semantic metadata linking open and proprietary pharmaceutical data sets for clinical trials management.

FIG. 31, depicts semantic metadata connecting an information ecosystem with open and proprietary clinical data sets for pharmaceutical development and pipeline management.

FIG. 32, depicts Visualizing Value Care: Connecting Doctors, Devices, Documents and Streams-Visualizing Value Care for Collaborative Care-Giving Teams.

FIG. 33, depicts a New Paradigm for Collaborative Value Care with Cognitively-enriched Enterprise Imaging.

FIG. 34, depicts Cognitively-enriched Enterprise Imaging: Diagnostic, Procedural and Evidence Imaging, along with Imaged-Based Clinical Reports.

FIG. 35, depicts Cognitively-enriched Enterprise Imaging Repository Information Architecture.

FIG. 36, depicts Cognitively-enriched Enterprise Imaging—Best Practices Workflow.

FIG. 37, depicts Streaming Analytics Architecture for Hospital-based Enterprise Imaging.

FIG. 38, depicts Imagery Document Exchange with Metadata Registries and an Enterprise Imaging Data Repository.

FIG. 39, depicts Biomedical Knowledge Exchange with Augmented Intelligence Networks.

FIG. 40, depicts Integrative Systems Biology with Multimodal, Multi-Scalar Visual Bioinformatics.

FIG. 41, depicts Augmented Pattern Recognition with Multimodal Radiogenomic Imagery and Adaptive Mind-Machine Learning.

FIG. 42, depicts Pattern Matching Algorithms for Multiple Classes of Oncology Images.

FIG. 43, depicts Early Disease Detection with Multimodal, Multi-Scalar Biomedical Sensors.

FIG. 44, depicts Clinical Knowledge Networks Integrating Biomedical Research with Clinical Medicine, "from Bench to Bedside".

FIG. 45, depicts Value Drivers for Biomedical Knowledge Exchange with Augmented Intelligence Networks.

FIG. 46, depicts Molecular Profiling with Predictive Prognostic Markers for Precision Cancer Medicine.

FIG. 47, depicts Cancer LINQ—A Learning Intelligence Network Connecting Patients, Providers and Researchers with Biomedical Data and Knowledge.

FIG. 48, depicts Connecting Collaborative Partnerships for Multiomic Data Analysis and Personalized Precision Medicine.

FIG. 49, depicts Precision Diagnostics and Precision Targeted Therapeutics Information Sciences for Personalized Precision Medicine.

FIG. 50, depicts Clinically Actionable Information from Big Data as the foundation for Personalized Precision Medicine.

FIG. 51, depicts "See One. Do One. Teach One." Surgical Telementoring, Teamwork and Training.

FIG. 52, depicts Imagery Guided Computer Assisted Surgery.

FIG. 53, depicts Informatics-Enriched Robotic Assisted Surgery.

FIG. 54, depicts Streaming Augmented Reality Surgical Instruction.

FIG. 55, depicts Surgical Navigation and Guidance with 3D Data Visualization and Streaming Augmented Reality.

FIG. 56, depicts Visualizing the Surgical Site for Robotic Assisted Intervention.

FIG. 57, depicts an Imagery Guided Minimally Invasive Surgical Robotic System.

FIG. 58, depicts Visio-Spatial Algorithms Development for Precision Guided Surgery.

FIG. 59, depicts Live Surgical Demonstration with Expert Panels as Collaborative Teaching Tools.

FIG. 60, depicts Live Remote Intraoperative Telesurgical Consultation during Aneurysm Repair.

FIG. 61, depicts Live Remote Surgical Telementoring, Teamwork & Training with Interactive Streaming Video and Multisensory Augmented Reality.

FIG. 62, depicts interconnected Ecosystems of the Future for Informatics-Enriched Imagery Guided Interventions.

FIG. 63, depicts various techniques for Machine Learning with Medical Imaging.

FIG. 64, depicts a Framework for Cancer Metastasis Detection with Deep Learning Models and Whole Slide Imaging.

FIG. 65, depicts visualization of Tumor Region Detection with Slide/Heatmap Overlays.

FIG. 66, depicts Pancreatic Cancer Computer Assisted Detection with Convolutional Neural Networks.

FIG. 67, depicts Pulmonary Embolism Identification with Machine Learning.

FIG. 68, depicts Bone Age Assessment with Deep Learning Systems.

FIG. 69, depicts Video-based Attributes Labeling and Semantic Identification.

FIG. 70, depicts Data Extraction for Training Machine Learning Systems with Medical Outcomes.

FIG. 71, depicts illuminating "black-box" understanding of Machine Learning results developed from Neural Networks [e.g., XAI—Explainable Artificial Intelligence].

FIG. 72, depicts Convolutional and Recurrent Neural Networks with Long Short-Term Memory [LSTM] in Medical Imaging.

FIG. 73, depicts Data Mining, Training and Labeling with Annotated Medical Images using Convolutional and Recurrent Neural Networks with LSTM.

FIG. 74, depicts a Periodic Table of Artificial Intelligence with "Elementary" PAIR Techniques [Perceive-Assess-Infer-Respond].

FIG. 75, depicts implementing Data-Information-Knowledge Networks with Machine Learning for BioIntelligence.

FIG. 76, depicts various biomedical applications for Nanorobotics.

FIG. 77, depicts several typical features of Nanorobots.

FIG. 78, depicts monitoring Nanorobotic agents designed to treat cancer.

FIG. 79, depicts medical micro robots actuated by clinical MRI scanners.

FIG. 80, depicts Personalized Precision Targeted Theranostic Nanomedicine.

FIG. 81, depicts Imagery Guided Precision Theranostics with Targeted Drug Payloads.

FIG. 82, depicts Nanoparticle-based Imaging Diagnostics and Therapy.

FIG. 83, depicts Multifunctional Nanoparticles for Theranostic Nanomedicine.

FIG. 84, depicts Integrating Theranostics Techniques with Molecular Imaging Modalities.

FIG. 85, depicts Drug Delivery, Cell Destruction and Micro-Surgery with in vivo Imaging Theranostics.

DETAILED DESCRIPTION

A network system 1 for allowing users to concurrently communicate live; concurrently collaborate live, concurrently consult live, and concurrently instruct live while concurrently viewing multiple sources of streaming imagery data 13 on a display screen using sketched and annotated participant cognitive collaborant input illustrations over streaming imagery data 13 among a group of remotely located participant cognitive collaborants 10, including heterogeneous networked teams of persons, machines, devices, neural networks, robots and algorithms.

The network system having at least one or more TIMS Clini-Pod Network Servers (CNS) 2 including associated data bases in communication with local area networks 3, in some circumstances connected to and having access to a medical PACS server 4 including associated database all capable of using the protocols required by the DICOM Standard and all having access to DICOM modality work list utilities for appending imagery metadata 5 including associated databases providing medical patient metadata, as well as imagery metadata, semantic metadata and annotations, and archived annotated imagery. To collect streaming imagery data 13 the system together with at least one TIMS Clini-Dock 6 in contact with the local area network 3 wherein the TIMS Clini-Dock 6 is providing live streaming imagery data to the local area network 3 as it receives concurrent sources of live streaming imagery data 6 from multiple medical modalities 7, 8, 9 such as, but not limited to, ultrasound, fluoroscopy and video. A participant cognitive collaborant can view streaming imagery data 13 in single file format structures, including those as specified in the DICOM Standard together with participant cognitive collaborant input illustrations 18 which include, telestrations 21, drawings 22 and annotations 234 (known herein as input illustrations from participant cognitive collaborants) over the streaming imagery data and saving that streaming imagery data, relevant imagery metadata, including appended imagery metadata and semantic metadata and annotations, together with input illustrations from participant cognitive collaborants 18 in single file format structures, including those as specified in the DICOM Standard, locally in media libraries or image data repositories on their respective computer storage devices, in image data repositories on TIMS Clini-Pod Network Servers (CNS) 2, in image data repositories on cloud storage devices and locations, in image data repositories on picture archiving and communications systems PACS 4 or in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

This invention allows for one or more TIMS Clini-Ports 10 to concurrently use the network system at the same time. The network system 1 also allows participant cognitive collaborants to concurrently collaborate live, as defined by this system. The plurality of TIMS Clini-Ports can concurrently view multiple sources of live and archived streaming imagery data 13, and concurrently create input illustrations 18 over that streaming imagery data 13 which include telestrations 21, drawings 22 and annotations 23, as they are appended to that imagery, and encapsulate and save those participant cognitive collaborant input illustrations, including telestrations, drawings, and annotations, together with streaming imagery data, and relevant imagery metadata, including appended imagery metadata, from the collaboration session in single file format structures, known as collaborated imagery files. The network system 1 'single file encapsulate and save' functionality encapsulates and saves collaborated imagery files in single file format structures, as may be required or allowed by standards for clinical documentation or medical records storage, including those as specified in the DICOM Standard, Clini-Pod Network locally in media libraries or image data repositories on their respective computer storage devices, in image data repositories on TIMS Clini-Pod Network Servers (CNS) 2, in image data repositories on cloud storage devices and locations, in image data repositories on picture archiving and communications systems PACS 4 or in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

TIMS Clini-Ports can retrieve archived collaborated imagery files for use during current or future collaboration sessions. TIMS Clini-Ports can include collaborated imagery files in patient studies. In one embodiment, a collaboration session can include one or more participant cognitive collaborants that can utilize personal digital assistants (PDA) over the internet 12.

A method for allowing one or more participant cognitive collaborants to concurrently collaborate live on medical images 13, all participants clients running substantially the same TIMS Clini-Port software application programs on each of the participant cognitive collaborant's computers;

storing the programs on each of the participant cognitive collaborant's computers. Each participant cognitive collaborant computer displaying the graphic user interface output 25 of those programs on their computer display. Each participant cognitive collaborant computer linking to each other and to TIMS Clini-Pod Network Servers (CNS) 2 using local area networks 3. All TIMS Clini-Ports 10 have access to local area networks 3 and internet 12. TIMS Clini-Pod Network Servers (CNS) 2 providing authentication and authorization to each participant cognitive collaborant wherein linking the participant cognitive collaborant to DICOM Modality Worklist utilities 5, to image data repositories connected to picture archiving and communications systems via PACS servers 4, to other image data repositories compliant with standards for digital imaging and communications in medicine DICOM, to image data repositories connected via internet 12 to cloud storage devices and locations or on any other repository that allows streaming imagery data, annotations and metadata, including semantic metadata and annotations, to be combined in native single file format structures for viewing medical images 13, including clinical data repositories, personalized clinical knowledge repositories, clinical cognitive vismeme vaults and metadata repositories.

Streaming imagery data into local area networks 3 wherein TIMS Clini-Docks 6 are connected directly to medical modalities 7, 8, 9 acquiring live streaming imagery data or archived streaming imagery data, streaming that imagery data to TIMS Clini-Ports 10 via local area networks 3. TIMS Clini-Ports 10 acquire lists 15 of available medical modalities 7, 8, 9 from a local area network 3. Included in this network is are TIMS Clini-Pod Network Servers (CNS) 2 having associated databases, identifying each participant cognitive collaborant and the streaming imagery data available to each participant cognitive collaborant; identifying each participant cognitive collaborant the streaming imagery data that is available on each participant cognitive collaborant's computer. Also, local area networks 3 can be connected to the internet 12.

When a participant cognitive collaborant wants to view medical imagery and collaborate on that streaming imagery data with others, that participant cognitive collaborant selects a channel on the multi-channel source selection tab for viewing streaming imagery data 15, 25 so he/she can initiate a collaboration session, as depicted in FIG. 3. When participant cognitive collaborants are in a collaboration session, TIMS Clini-Pod Network Servers (CNS) 2 are providing updates to each participant cognitive collaborant's computer at a rapid frame rate so each participant cognitive collaborant's computer concurrently displays the same imagery. In other words, TIMS Clini-Pod Network Servers (CNS) 2 updates any changes to each and all of the streaming imagery data on each of the participant cognitive collaborant's computers with synchronized signals sent over local area networks 3 dynamically such that all streaming imagery data on all participant cognitive collaborant computer displays are the same, including sending each participant cognitive collaborant's input illustrations 18, which include, telestrations 21, drawings 22, and annotations 23, and illustrations over the streaming imagery data 13 made by any of the participant cognitive collaborants 10.

TIMS Clini-Pod Network Servers (CNS) 2 with dynamic signal synchronization ensures that the same imagery refresh rate is concurrently available on all participant cognitive collaborant computers. TIMS Clini-Pod Network Servers (CNS) 2 use a process of local registration to identify the image frames needed for viewing on each of the participant cognitive collaborant computers, and send to each of them only the image frames necessary for participation in a collaboration session. TIMS Clini-Pod Network Servers (CNS) 2 enables each participant cognitive collaborant 10 to use a scalable window so all input illustrations 18 for each and every participant cognitive collaborant 10 are dynamically ratio metric based on the underlying image aspect ratio of the respective computer of each participant cognitive collaborant 10. Each participant cognitive collaborant 10 views what every other authorized participant cognitive collaborant 10 views in that session.

TIMS Clini-Pod Network Servers (CNS) 2 distribute copies of streaming imagery data selected for use during a collaboration session to each of the participant cognitive collaborants. Since participant cognitive collaborants 10 collaborate only with copies of images, they do not alter the original streaming imagery data in any way. TIMS Clini-Pod Network Servers (CNS) 2 with dynamic signal synchronization allows at least one participant cognitive collaborant 10 to telestrate 21, draw 22, annotate 23, input illustrations 18 over the streaming imagery data 13 in a concurrently collaboration session wherein a participant cognitive collaborant 10 is telestrating 21, drawing 22, annotating 23 input illustrations 18 over the streaming imagery data 13. This approach of generating input illustrations 18 on TIMS Clini-Pod Network Servers (CNS) 2, and distributing only those input illustrations 18, and not the underlying images to each participant cognitive collaborant 10, significantly improves operating performance and reduces image latency and wait times.

TIMS Clini-Pod Network Servers (CNS) 2 manage input illustrations 18 from all participant cognitive collaborants 10 in a concurrently collaborative environment with image streams which can include multiple streams of streaming imagery data. TIMS Clini-Pod Network Servers (CNS) 2 manage participant cognitive collaborant 10 input illustrations 18, which include telestrations 21, drawings 22, and annotations 23 as they are appended to that imagery 13, and encapsulate and save those participant cognitive collaborant input illustrations 18, which include telestrations 21, drawings 22 and annotations 23 together with streaming imagery data 13, and relevant imagery metadata, including appended imagery metadata, from the collaboration session in single file format structures, known as collaborated imagery files.

TIMS Clini-Pod Network Servers (CNS) 2 'single file encapsulate and save' functionality encapsulates and saves collaborated imagery files in single file format structures, as may be required or allowed by standards for clinical documentation or medical records storage, including those as specified in the DICOM Standard. Users can encapsulate and save collaborated imagery files locally in media libraries or image data repositories on their respective computer storage devices, as depicted in FIG. 4, which contain all of the input illustrations 18 from all participant cognitive collaborants 10. Users can also encapsulate and save collaborated imagery files in image data repositories on TIMS Clini-Pod Network Servers (CNS) 2, in image data repositories on picture archiving and communications systems PACS 4, in other image data repositories compliant with standards for digital imaging and communications in medicine DICOM, or on any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

TIMS Clini-Pod Network Servers (CNS) 2 create session logs that include collaboration session identification, participant cognitive collaborant information, information about streaming imagery data, including associated patient metadata, along with session dates and times, as shown in FIG. 9.

In one embodiment, several participant cognitive collaborants 10, also known as Radiologist, Pathologist and Oncology Surgeon, utilize the network system 1 to collaborate in the provision of oncology care.

At Time 1, Radiologist retrieves patient's archived medical imagery from a PACS 4 image repository. Radiologist detects a suspicious nodule on several images and inputs telestrations 21 and drawings 22 indicating the location of the nodule, along with text annotations 23 charactering its clinical significance and voice annotations 23 summarizing his findings. Radiologist utilizes the 'single file encapsulate and save' functionality of the network system 1 to incorporate those input illustrations 18, together with medical imagery data 13 and identifying patient metadata, in single file format structures, known as a collaborated imagery file (CIF #1). Radiologist archives the CIF #1, which has been encapsulated and saved in a single file format compliant with the DICOM Standard, and sends to PACS 4 for review and discussion with other members of the oncology care team.

At Time 2, Radiologist invites Pathologist to a collaboration session to discuss his findings of a suspicious nodule as described in CIF #1. While both participant cognitive collaborants 10 are concurrently viewing CIF #1, Radiologist retrieves several additional collaborated imagery files from his local media library, and from PACS 4, of relevant prior patient medical imagery for display and viewing during the collaboration session, as shown in FIG. 4. Participant cognitive collaborants 10 record, encapsulate and save their input illustrations 18 for each of several imagery files selected for discussion during the collaboration session, as CIF #2, #3, #4. Pathologist combines CIF #1 with CIF #2, #3, #4 as collaborated imagery study (CIS #1) and stores CIS #1 on PACS 4 for subsequent review and discussion with Oncology Surgeon, who was unavailable at Time 2 to join collaboration session.

At Time 3, Oncology Surgeon reviews CIS #1 and selects CIF #4 to create a surgical roadmap to guide tumor excision using input illustrations 18, which include telestrations 21, drawings 22, and voice annotations 23. Oncology Surgeon saves surgical roadmap as CIF #5.

At Time 4, Oncology Surgeon retrieves surgical roadmap (CIF #5), for intra-operative guidance during tumor removal.

At Time 5, during surgery, Oncology Surgeon invites Radiologist and Pathologist for intra-operative consultation during tumor excision.

At Time 6, participant cognitive collaborants—Oncology Surgeon, Radiologist, and Pathologist—utilize network system 1 to retrieve and concurrently view nodule (CIF #1), tumor pathology images (CIF #2, #3, #4), and surgical roadmap (CIF #5) from PACS 4, along with live streaming imagery data from endoscope 13 used during tumor excision.

Periodically during the surgical procedure, at Times 7, 8, 9, Oncology Surgeon consults with Pathologist to confirm sufficiency of margins around excised tumor. Pathologist confirms sufficiency of margins with telestrations 21, drawings 22, and text annotations 23, over live endoscopy images, saving all those input illustrations 18, together with associated streaming imagery data 13 in single file format structure as CIF #6.

At Time 10, Oncology Surgeon retrieves CIF #6 from PACS 4, which contains Pathologist's input illustrations 18 regarding excised tumor margins, and dictates a post-operative surgical report adding voice annotations 23, to telestrations 21, and drawings 22 to endoscopic images from excision surgery and saving in single file format structure as CIF #7.

At Time 11, Oncology Surgeon combines pre-operative surgical roadmap CIF #5 with post-operative surgical report CIF #7, along with pre-operative image study CIS #1 (which includes CIF #1, #2, #3, #4) into comprehensive clinical report (CIS #2) for distribution to the oncology care team.

Oncology Surgeon can encapsulate and save CIS #2 in single file format structures as specified in the DICOM Standard and send to PACS 4. Oncology Surgeon utilizes the 'single file encapsulate and save' functionality of the network system to encapsulate and save CIS #2 in single file format structures as specified in the DICOM Standard and send to PACS 4. Oncology Surgeon can also encapsulate and save CIS #2 in single file format structures as may be required or allowed for clinical documents, for storage in patient's electronic medical record, or for patient billing.

At Time 12, Oncology Surgeon retrieves CIS #2 from PACS 4, utilizes the network system 1 to remove all relevant identifying patient metadata, and encapsulates and saves as an anonymized collaborated imagery study (CIS #3) for use as teaching files with surgical fellows.

In another embodiment, a participant cognitive collaborant 10, known as Hospitalist, remotely monitors live streaming imagery data 13 from a surgical procedure in an operating room on channel one, and archived streaming imagery data 13 of a patient recovering in Intensive Care Unit, on channel two. While monitoring streaming imagery data 13 on channels one and two, as depicted in FIG. 3 and FIG. 7, Hospitalist accepts an invitation to join a collaboration session on channel three to monitor and consult live on a diagnostic procedure in the emergency room, as shown in FIG. 6. The live consultation involves review of patient images from an analog ultrasound machine and a digital CT scanner in the emergency room. During the collaboration session in the emergency room on channel three, Hospitalist utilizes the multi-channel viewing capability of Applicant's network system 1 to continue live monitoring of streaming imagery data 13 on channel one and channel two, and to retrieve and view additional archived imagery data 13 of patient recovery in Intensive Care Unit.

In another embodiment, a patient is recalled to undergo a second PET/MRI scan. The previous test yielded inconclusive, due to patient motion during image capture, thus requiring a costly retest. During the second test, Radiologist was able to review the MRI images captured 13 during the first portion of the test, while the patient was still being imaged in PET unit and confirm that the second MRI scan was useable. Radiologist was able to advise Attending Molecular Pathologist during PET scan 13 of additional regions of interest with input illustrations 18 for further investigation.

In another embodiment, Oncologist wishes to convene a virtual tumor board for the following day involving multi-specialist collaboration with a patient's Radiologist, Pathologist, Oncology Surgeon and himself. Oncologist sends invitations to colleagues along with several collaborated imagery files he wishes to review during the collaboration session. Radiologist and Pathologist confirm availability, but Oncology Surgeon is unable to attend. However, Oncology Surgeon is able to annotate 23 with telestrations 21 and drawings 22 on several key images 13 included in the collaborated imagery study sent with the session invitation. Oncology Surgeon also includes his clinical notes and an audio file along with his report, together all encapsulated as a CIF and returned to the session host.

During the collaboration session the following day, the host Oncologist retrieves patient images from PACS 4 and from his local media library 25 containing the CIF 13, 18 sent to him from Oncology Surgeon, viewing both images concurrently when colleagues from radiology and pathology join the collaboration session. During the collaboration session, Pathologist is monitoring on the third channel of the multi-channel streamer 7, 8, 9, 25, a tumor removal of another patient in the operating room, advising that Oncology Surgeon intra-operatively regarding sufficiency of margins of tumor removal from that patient. Oncology Surgeon is able to share live imagery 13 of the tumor removal with the radiology and oncology colleagues who have joined the virtual tumor board collaboration session.

At the conclusion of the collaboration session, host Oncologist encapsulates and saves input illustrations 18 from participant cognitive collaborants 10, including encapsulated audio clinical notes and biopsy reports as clinical documents, saving them as collaborated imagery files and sending them to all participant cognitive collaborants 10 as well as invitees unable to attend. Additionally, the CIFs 13, 18 are sent to PACS 4 for inclusion in the patient's electronic medical records as well to patient's referring clinician.

Other embodiments of the invention include applications for cognitive value creation with knowledge mapping, advanced and augmented data analytics, as depicted in FIGS. 19 through 24; for augmenting clinical intelligence with semantic metadata and imagery annotation, as depicted in FIGS. 25 through 31; for cognitively-enriched enterprise imaging with streaming imagery informatics, as depicted in FIGS. 33 through 38; for collaborative precision medicine with multiomic data analytics, as depicted in FIGS. 39 through 50; for informatics-enriched imagery guided intervention, including robotic-assisted surgery, as depicted in FIGS. 51 through 62; for machine learning with medical imaging, including deep learning, transfer learning, reinforcement learning, convolutional neural networks, recurrent neural networks, LSTM and NLP, as depicted in FIGS. 63 through 75; for precision guided biomedical nanorobotics, as depicted in FIGS. 76 through 79; and for personalized precision targeted theranostic nanomedicine, as depicted in FIGS. 80 through 85.

Various techniques for machine learning with medical imaging are specified in FIG. 63, including among others, artificial neural networks, ensemble learning and multiple instance learning. Other applications for machine learning in medicine are depicted in FIG. 74, a Periodic Table of Artificial Intelligence with "Elementary" PAIR Techniques [Perceive-Assess-Infer-Respond]. Those AI applications include speech, audio and image recognition; data analytics, inference and reasoning; text extraction, problem solving and decision making; language understanding and generation; knowledge refinement, category and relationship learning [semantics]; as well as communications, manipulation and control.

Other embodiments of the invention may include, but are not limited to, various combinations of algorithms, applications, tools and techniques for machine learning in medicine, e.g., deep learning, transfer learning, reinforcement learning, convolutional neural networks, recurrent neural networks, LSTM networks, natural language processing and augmented analytics, as well as those specified above.

The principle preferred embodiments and modes of operation of the present invention have been described in the forgoing specification. The invention which is intended to be protected herein, however, is not to be construed as limited to the particular embodiments disclosed, since these embodiments are to be regarded as illustrative rather than restrictive. Variations and changes may be made by others without departing from the spirit of this invention. Accordingly, it is expressly intended that all such variation and changes which fall within the spirit and scope of the claims be embraced thereby.

CROSS-REFERENCE TO RELATED APPLICATIONS

This application is Continuation-in-part of U.S. application Ser. No. 17/353,791 filed Jun. 21, 2021 entitled:

"Augmenting Clinical Intelligence with Federated Learning, Imaging Analytics and Outcomes Decision Support"

naming as inventor James Paul Smurro, which is incorporated herein by reference in its entirety.

This application is Continuation-in-part of U.S. application Ser. No. 16/450,974 filed Jun. 24, 2019 entitled:

"Cognitive Collaboration with Neurosynaptic Imaging Networks, Augmented Medical Intelligence and Cybernetic Workflow Streams"

naming as inventor James Paul Smurro, which is incorporated herein by reference in its entirety.

This application is Continuation-in-part of U.S. application Ser. No. 15/731,201 filed May 2, 2017 entitled:

"Cognitive Collaboration with Neurosynaptic Imaging Networks, Augmented Medical Intelligence and Cybernetic Workflow Streams"

naming as inventor James Paul Smurro, which is incorporated herein by reference in its entirety.

This application is Continuation-in-part of U.S. application Ser. No. 14/544,807 filed Feb. 18, 2015 entitled:

"Multimodal Cognitive Communications and Collaborative Knowledge Exchange with Visual Neural Networking and Packetized Augmented Intelligence"

naming as inventor James Paul Smurro, which is incorporated herein by reference in its entirety.

This application Claims Priority from U.S. Provisional Application 61/967,323 filed Mar. 15, 2014 entitled:

"Network systems apparatus and method of use adapted for tele-visual communications and collaboration with streaming medical imagery and clinical informatics by networked teams of minds, machines, languages and tools, including recursively annotating, tagging, encapsulating and saving shared tele-visual communications, collaborations, imagery and informatics together as clinical cognitive vismemes in standard known file formats for interoperable delivery of personalized medicine"

naming as inventor James Paul Smurro, which is incorporated herein by reference in its entirety.

This application is Continuation-in-part of U.S. application Ser. No. 13/999,688 filed Mar. 15, 2014 entitled:

"System and method for recursive cognitive enrichment with collaborative network exchange of multimodal multistream digital communications across neurosynaptic butterfly networks"

naming as inventor James Paul Smurro, which is incorporated herein by reference in its entirety.

This application Claims Priority from U.S. Provisional Application 61/852,625 filed Mar. 15, 2013 entitled:

"Network apparatus system and method of use adapted for viewing recursively annotating and tagging, saving and retrieving, consulting and collaborating with semantically searchable clinical cognitive vismemes, together with encapsulated metadata and dicomized image-waveforms, over visual neural networks for early detection, diagnosis, prognosis, treatment, measurement and monitoring of disease, including delivery of precision personalized medicine across interconnected knowledge networks"

naming as inventor James Paul Smurro, which is incorporated herein by reference in its entirety.

This application may be related to the following commonly assigned and commonly filed U.S. patent applications, each of which is incorporated herein by reference in its entirety:

1. U.S. Pat. No. 8,924,864 B2 entitled "System and method for collaboratively communicating on images and saving those communications and images in a standard known format", naming as inventors Mariotti et al, issued Dec. 30, 2014.
2. U.S. patent application 20140176661 AI entitled "System and method for surgical telementoring and training with virtualized telestration and haptic holograms, including metadata tagging, encapsulation and saving multi-modal streaming medical imagery together with multi-dimensional [4-d]virtual mesh and multi-sensory annotation in standard file formats used for digital imaging and communications in medicine (dicom)", naming as inventors Smurro et al, published Jun. 26, 2014.

What is claimed is:

1. A cognitive communications system enabling multi-channel multiplexed communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, including augmented generative AI algorithms, models and systems, and heterogeneous networked teams composed thereof, the cognitive communications system enabling both synchronous and asynchronous multimodal clinical communications, collaboration, consultation and instruction, including recursive cognitive enrichment and collaborative knowledge exchange, with streaming imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, allowing each participant cognitive collaborant to capture, retrieve and concurrently view at least one source of streaming medical modality imagery data, and at least one or more sources of heterogeneous streaming imagery data, medical and non-medical streaming imagery data, multimodal media and combinations thereof, including images, video, modality imagery, audio, video and haptic wave forms and files, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, both live and archived streaming imagery data, enabling both synchronous and asynchronous multimodal clinical communications, collaboration, consultation and instruction, as well as recursive cognitive enrichment and collaborative knowledge exchange, with streaming imagery data in collaboration sessions practiced by and among at least one or more participant cognitive collaborants during various stages of medical disease and injury management, including detection, diagnosis, prognosis, treatment, measurement, monitoring and reporting, as well as workflow optimization with operational analytics for outcomes, performance, results, resource utilization, resource consumption and costs, each participant cognitive collaborant able to view, curate, annotate and tag the heterogeneous streaming imagery data, comprising a tele-visual imagery informatics management system including, at least one or more tele-visual imagery informatics management system clini-docks, wherein each clini-dock is adapted for independent acquisition and transmission of signals from other sources of streaming imagery data at native, enhanced or reduced resolutions and native enhanced or reduced frame rates, used for the acquisition and transmission of, live or archived streaming imagery data, including images, video, modality imagery, audio, video and haptic wave forms and files, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, analog or digital video signals in standard or non-standard resolutions, medical or non-medical imagery, in compressed or uncompressed imagery formats; at least one or more tele-visual imagery informatics management system clini-pod network servers, wherein each server is a neurosynaptic network node comprising at least one streamer, splitter, router, server and storage device enabling at least one or more participant cognitive collaborants, including persons, machines, devices, neural networks, robots and algorithms, including augmented generative AI algorithms, models and systems, and heterogeneous networked teams composed thereof, to concurrently view, communicate, collaborate, consult and instruct among participant cognitive collaborants using at least one or more sources of streaming imagery data acquired and transmitted by tele-visual imagery informatics management system clini-docks, including live streaming imagery data, archived streaming imagery data, appended streaming imagery metadata, including appended semantic metadata and annotations, cognitive collaborant annotations, and archived collaborated imagery files during a synchronous or asynchronous collaboration session, establishing and maintaining channel communications for each and all of the one or more sources of streaming imagery data each participant cognitive collaborant wishes to view, monitor and collaborate with, enabling concurrent collaboration including viewing, curation, annotation and tagging with each and all of the one or more sources of streaming imagery data acquired and transmitted by tele-visual imagery informatics management system clini-docks, enables at least one or more participant cognitive collaborants to concurrently view, communicate, collaborate, consult and instruct, including curation, annotation and tagging, with live streaming imagery data, archived imagery data, appended imagery metadata, including appended semantic metadata and annotations, collaborated annotations, and archived collaborated imagery files during a synchronous or asynchronous collaboration session, enables at least one or more participant cognitive collaborant in multiple locations, some of whom may be located remotely to the sources of streaming imagery data, to concurrently view, communicate, collaborate, consult and instruct, including curation, annotation and tagging, with live streaming imagery data, archived imagery data, appended imagery metadata, including appended semantic metadata and annotations, collaborated annotations, and archived collaborated imagery files during a synchronous or asynchronous collaboration session, enables at least one or more participant cognitive collaborant to independently add sources of streaming imagery data, adjust, enhance or reduce resolutions or frame rates of streaming imagery data with a multi-channel communications control interface, and independently view those additional channels of streaming imagery data and independently select which of those channels to bring into a collaboration session, conveys instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, encapsulates and saves collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, stores collaborated imagery files from all participant cognitive collaborants locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieves collaborated imagery files from all participant cognitive collaborants stored locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishes and distributes collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files, dynamically manages and controls with at least one or more associated databases, authorization, authentication, identity management, security, and access, publication and distribution privileges for viewing, communicating, collaborating, consulting and instructing, and cognitive collaborant privileges, including curation, annotation, tagging, encapsulation, saving, storage, retrieval and distribution of live streaming imagery data, archived imagery data, appended imagery metadata, including appended semantic metadata and annotations, collaborated annotations, and archived collaborated imagery files for each participant cognitive collaborant during collaboration sessions, including managing and controlling security tokens providing access for cognitive collaborants maintained in security metadata repositories, blockchain metadata repositories and blockchain data ledgers, enables both synchronous and asynchronous bidirectional communications with at least one or more local area networks, at least one or more wide area networks (internet) including imagery data repositories and combinations thereof during multiple collaboration sessions, enables identification, tracking and monitoring of participant cognitive collaborants by assignment of unique colors for annotations of streaming imagery data, archived collaborated imagery files and cognitive collaborant annotations, that include telestrations, drawings, illustrations, alpha-numeric text annotations, as well as cognitive collaborant annotations combined with alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, enables colorized telestration, annotation and masking of colorized attention maps and colorized prediction bases for explainable artificial intelligence by participant cognitive collaborants by assignment of unique colors for annotations of streaming imagery data, archived collaborated imagery files and cognitive collaborant annotations, including telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, costs annotations, resource consumption annotations and resource utilization annotations; and at least one or more tele-visual imagery informatics management system clini-ports that allows for multiple participant cognitive collaborants, each of whom can capture live streaming imagery data together with associated imagery metadata, including semantic metadata and annotations, and bring into the collaboration session, retrieve archived streaming imagery data together with associated imagery metadata, including semantic metadata and annotations, and bring into the collaboration session, concurrently view, communicate, collaborate, consult and instruct with streaming imagery data, enables curation, annotation and tagging that streaming imagery data with collaborated annotations that include telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, enables encapsulation and saving collaborated streaming imagery data and archived imagery metadata, including archived semantic metadata and annotations, together with appended imagery metadata, including appended semantic metadata and annotations, and collaborated annotations and from each collaboration session, including asynchronous or synchronous collaboration with at least one or more participant cognitive collaborants, in native, single file format structures, known as collaborated imagery files, enables multimodal clinical communications, collaboration, consultation and instruction, including viewing, curating, annotating and tagging, using at least one or more sources of streaming imagery data shared among at least one or more participant cognitive collaborants with a multi-channel stream viewer that enables capture, retrieval and concurrent viewing of both live and archived medical imagery streams together with associated metadata during various stages of medical disease and injury management, including detection, diagnosis, prognosis, treatment, measurement, monitoring and reporting, as well as workflow optimization with operational analytics for outcomes, performance, results, resource utilization, resource consumption and costs, enables independently adding sources of streaming imagery data, adjust, enhance or reduce resolutions or frame rates of streaming imagery data with a multi-channel communications control interface, and independently view those additional channels of streaming imagery data and independently select which of those channels to bring into a collaboration session, enables conveying instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, and not reliant upon any external communications network.

2. The cognitive communications system of claim 1, wherein the tele-visual imagery informatics management system clini-pod network servers are modular and scalable clusters of gateway streamer servers configured to support multiple network topologies, including peer-to-peer, hub-and-spoke, mesh chord and core-spine-leaf networks, as well as in 2-tier, 3-tier, or N-tier application architectures, and heterogeneous network combinations thereof, each gateway streamer server enabling neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, multimodal media and combinations thereof, and together with images, video, modality imagery, waveforms, audio and haptic files, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

3. The cognitive communications system of claim 1 for the acquisition and transmission of medical streaming imagery data, including medical images, medical video, medical modality imagery, medical wave form imagery, clinical maps, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, the cognitive communications system preserving the clinical integrity of medical streaming imagery data from medical devices, systems and equipment cleared for medical use, including clinical diagnostic purposes, care delivery and patient monitoring, enabling both synchronous and asynchronous multimodal clinical communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, including augmented generative AI algorithms, models and systems, and heterogeneous networked teams composed thereof, including viewing, curating, annotating and tagging streaming medical imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, encapsulating and saving collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, storing collaborated imagery files from all participant cognitive collaborants locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieving collaborated imagery files from all participant cognitive collaborants stored locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files, that can be viewed, curated, annotated, tagged, encapsulated and saved together as collaborated medical imagery files and cleared for use with approved medical devices, equipment, systems, image and data repositories, in native, single file format structures, including those compliant with standards for digital imaging and communications in medicine.

4. The cognitive communications system of claim 1 for acquiring, transmitting, encapsulating, saving, storing, retrieving, publishing and distributing collaborated imagery files, including live or archived collaborated imagery files, collaborated annotations and tags, together with streaming imagery data, relevant imagery metadata, including semantic metadata and annotations, and appended imagery metadata, including appended semantic metadata and annotations, from the collaboration session in native, single file format structures, known as collaborated imagery files, during various stages of medical disease and injury management, including detection, diagnosis, prognosis, treatment, measurement, monitoring and reporting, as well as workflow optimization with operational analytics for outcomes, performance, results, resource utilization, resource consumption and costs.

5. The cognitive communications system of claim 1 for enabling the encapsulation and saving collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, during collaboration sessions practiced by and among at least one or more participant cognitive collaborants, including persons, machines, devices, neural networks, robots and algorithms, including augmented generative AI algorithms, models and systems, and heterogeneous networked teams composed thereof.

6. The cognitive communications system of claim 1, wherein the system is adapted for non-clinical applications, including education, finance, and manufacturing, by processing non-medical streaming data with recursive cognitive enrichment for knowledge exchange in heterogeneous networked teams.

7. The system of claim 1, incorporating retrieval-augmented generation (RAG) primitives for semantic metadata retrieval and augmentation in collaborative sessions, predating contemporary Graph RAG by integrating vismemes with hypergraph knowledge representations.

8. The system of claim 1 for agentic AI orchestration, comprising: heterogeneous teams of AI agents for problem-solving, with viability scoring and Graph RAG integration for differentiated search in non-biomedical contexts.

9. The system of claim 1, utilizing clinical cognitive vismemes as tokenized assets for knowledge trading in non-PHI environments, extending to NFT-like structures for education and finance.

10. The system of claim 1 for integrated business architectures (IBAs), incorporating AI-driven metrics for revenues, quality, and service optimization in cross-industry applications.

11. The system of claim 1 for tokenized economies, using vismemes as NFTs for secure knowledge trading across collaborative networks in education and manufacturing.

12. The system of claim 1 for change resilience frameworks, sensing/rewiring/locking in learnings with cybernetic teams for AI-induced adaptations in business.

13. The system of claim 1, incorporating hypergraph models for spatial multiomics-inspired data in non-clinical analytics, with RAG for precision decision-making.

14. The system of claim 1 for outcomes performance evaluation, extending clinical analytics to non-healthcare with KPIs for resource utilization and costs.

15. The system of claim 1 for live multicasting in non-clinical collaborations, with secure vismemes for accelerated knowledge exchange in teams.

16. The cognitive communications system of claim 1, further comprising a multi-agent framework for creative problem-solving in non-biomedical contexts, comprising: emergent self-organizing teams of networked minds, machines, languages and tools that purposefully adapt, collaborate and innovate, with human-AI hybrids for differentiated search; viability scoring with Graph RAG integration.

17. The cognitive communications system of claim 1, adapted for non-PHI workflows in business architectures, comprising: emergent self-organizing teams of networked minds, machines, languages and tools that purposefully adapt, collaborate and innovate, with semantic knowledge graphs for multi-domain data fusion; Graph RAG for decision support in finance/engineering.

18. The system of claim 17, incorporating personal knowledge repositories (PKRs) for documenting best practices in education/business, extending clinical vaults to non-healthcare.

19. The cognitive communications system of claim 1, comprising an integrated business architecture (IBA) framework with emergent self-organizing teams of networked minds, machines, languages and tools that purposefully adapt, collaborate and innovate, with AI-driven metrics, enhancing revenues/quality/service in cross-industry applications.

20. The system of claim 1, incorporating biomolecular recognition techniques for multiomic data processing, drawing from Mershin's nano-bio interfaces for enhanced cognitive collaboration in biological and synthetic systems.

21. The system of claim 1 for digital biology applications, inspired by Jensen Huang's vision, using augmented generative AI for precision medicine simulations in computer-assisted drug design.

22. The system of claim 1, utilizing cybernetic teammate frameworks from HBS WP 25-043 for human-AI hybrid collaboration in resilience-building scenarios.

23. The system of claim 1 for virtuous circles in value network nodes (VNN), enabling recursive knowledge exchange with performance indicators for operational analytics.

24. The system of claim 1, incorporating Mershin's group research on bio-nano recognition for haptic and multisensory annotations in augmented reality sessions.

25. The system of claim 1 for JPM Healthcare 2025 alignments, with Huang's digital biology for radiopathomic and morpholomic data in cognitive enrichment.

26. The system of claim 1 for tokenized vismemes in blockchain ledgers, extending to NFT structures for secure multi-domain knowledge trading.

27. The system of claim 1 for integrated business architectures with AI metrics, optimizing revenues and quality in finance and manufacturing.

28. The system of claim 1 for hypergraph-based multi-omics-inspired analytics, with RAG for precision in non-clinical decision support.

29. The system of claim 1 for KPIs in non-healthcare outcomes, extending clinical analytics to resource and cost evaluation.

30. The system of claim 1 for secure live multicasting, using vismemes for accelerated team knowledge exchange in non-clinical settings.

31. The system of claim 1 for informatics innovation in manufacturing, optimizing workflows with multimodal communications.

32. The system of claim 1 for Huang's state of AI in healthcare trends, applying to digital biology for radiogenomic mapping.

33. The system of claim 1 for resilience frameworks, locking in learnings with governance in heterogeneous networked teams.

34. The system of claim 1 for primitives in provisionals, integrating vismemes for hypergraph representations in RAG.

35. The system of claim 1 for multi-agent problem-solving, with human-AI hybrids for creative non-biomedical contexts.

36. The system of claim 1 for change resilience, using generative AI for early signal sensing in cybernetic teams.

37. The system of claim 1 for IBAs with metrics, enhancing service in cross-industry AI applications.

38. The system of claim 1 for non-biomedical viability scoring, integrating Graph RAG in multi-agent frameworks.

39. The system of claim 1 for federated model training, privacy-preserving across non-medical repositories.

40. The system of claim 1 for multicasting in collaborations, secure for knowledge acceleration in teams.

41. The system of claim 1 for re-skilling knowledge workers, comprising multimodal media for adaptive learning in AI-augmented environments with See-One-Do-One-Teach-One pedagogy.

42. The system of claim 1 for data stream visualizations, comprising real-time monitoring of cognitive collaboration sessions with performance metrics and analytics dashboards rendered as vismemes.

43. The system of claim 1 for informatics innovation management, comprising workflow optimization with multimodal communications, recursive enrichment, and operational analytics for continuous improvement.

44. The system of claim 1 for agentic task allocation, comprising autonomous distribution of cognitive collaboration tasks among heterogeneous AI agents with viability scoring across value network nodes.

45. The system of claim 1 for Graph-RAG retrieval in agentic workflows, comprising differentiated semantic search with viability scoring across knowledge repositories connected as value network nodes.

46. The system of claim 1 for human-AI hybrid teams, comprising collaborative problem-solving with emergent intelligence in creative contexts across a neurosynaptic network of institutions.

47. The system of claim 1 for spatial multiomic integration, comprising tissue architecture analysis with molecular profiling for precision diagnostics.

48. The system of claim 1 for radiopathomic correlation, comprising integration of radiological and pathological data streams for comprehensive diagnosis.

49. The system of claim 1 for precision therapeutics targeting, comprising multiomic-guided treatment selection with augmented generative AI.

50. The system of claim 1 for patient stratification, comprising multiomic clustering for optimal treatment sub-population matching.

51. The system of claim 1 for explainable AI in clinical decision support, comprising colorized attention masking with interpretable feature visualization as a neurosynaptic trace within the institutional graph.

52. The system of claim 1 for attention map visualization, comprising highlighting salient features in medical imagery with confidence scoring and storing the resulting attribution maps as vismemes.

53. The system of claim 1 for regulatory-compliant AI documentation, comprising automated generation of model cards and validation reports for each deployed model instance.

54. The system of claim 1 for clinical AI validation, comprising continuous monitoring with performance metrics and drift detection for AI services participating in neurosynaptic workflows.

55. The system of claim 1 for enterprise imaging integration, comprising cognitive collaboration across PACS, VNA, and EHR systems.

56. The system of claim 1 for DICOM-compliant cognitive vismemes, comprising encapsulation of collaborated imagery with standards-based metadata for interoperable storage, retrieval, and exchange.

57. The system of claim 1 for cloud-native deployment, comprising N-tier architecture with core-spine-leaf networking for scalable cognitive collaboration across distributed institutions.

58. A method for multichannel multiplexed communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, including augmented generative AI algorithms, models and systems, and heterogeneous networked teams composed thereof, the method enabling both synchronous and asynchronous multimodal clinical communications, collaboration, consultation and instruction, including recursive cognitive enrichment and collaborative knowledge exchange, with streaming imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, allowing each participant cognitive collaborant to capture, retrieve and concurrently view at least one source of streaming medical modality imagery data, and at least one or more sources of heterogeneous streaming imagery data, medical and non-medical streaming imagery data, multimodal media and combinations thereof, including images, video, modality imagery, audio, video and haptic wave forms and files, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, both live and archived streaming imagery data, enabling both synchronous and asynchronous multimodal clinical communications, collaboration, consultation and instruction, as well as recursive cognitive enrichment and collaborative knowledge exchange, with streaming imagery data in collaboration sessions practiced by and among at least one or more participant cognitive collaborants during various stages of medical disease and injury management, including detection, diagnosis, prognosis, treatment, measurement, monitoring and reporting, as well as workflow optimization with operational analytics for outcomes, performance, results, resource utilization, resource consumption and costs, each participant cognitive collaborant able to view, curate, annotate and tag the heterogeneous streaming imagery data, the method comprising the steps of acquiring and transmitting signals from other sources of streaming imagery data at native, enhanced or reduced resolutions and native enhanced or reduced frame rates, used for the acquisition and transmission of, live or archived streaming imagery data, including images, video, modality imagery, audio, video and haptic wave forms and files, multiomic data-phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, analog or digital video signals in standard or non-standard resolutions, medical or non-medical imagery, in compressed or uncompressed imagery formats; enabling at least one or more participant cognitive collaborants, including persons, machines, devices, neural networks, robots and algorithms, including augmented generative AI algorithms, models and systems, and heterogeneous networked teams composed thereof, to concurrently view, communicate, collaborate, consult and instruct among participant cognitive collaborants using at least one or more sources of streaming imagery data acquired and transmitted by tele-visual imagery informatics management system clini-docks, including live streaming imagery data, archived streaming imagery data, appended streaming imagery metadata, including appended semantic metadata and annotations, cognitive collaborant annotations, and archived collaborated imagery files during a synchronous or asynchronous collaboration session, establishing and maintaining channel communications for each and all of the one or more sources of streaming imagery data each participant cognitive collaborant wishes to view, monitor and collaborate with, enabling concurrent collaboration including viewing, curation, annotation and tagging with each and all of the one or more sources of streaming imagery data acquired and transmitted by tele-visual imagery informatics management system clini-docks, enabling at least one or more participant cognitive collaborants to concurrently view, communicate, collaborate, consult and instruct, including curation, annotation and tagging, with live streaming imagery data, archived imagery data, appended imagery metadata, including appended semantic metadata and annotations, collaborated annotations, and archived collaborated imagery files during a synchronous or asynchronous collaboration session, enabling at least one or more participant cognitive collaborant in multiple locations, some of whom may be located remotely to the sources of streaming imagery data, to concurrently view, communicate, collaborate, consult and instruct, including curation, annotation and tagging, with live streaming imagery data, archived imagery data, appended imagery metadata, including appended semantic metadata and annotations, collaborated annotations, and archived collaborated imagery files during a synchronous or asynchronous collaboration session, enabling at least one or more participant cognitive collaborant to independently add sources of streaming imagery data, adjust, enhance or reduced resolutions or frame rates of streaming imagery data with a multi-channel communications control interface, and independently view those additional channels of streaming imagery data and independently select which of those channels to bring into a collaboration session, conveying instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, encapsulating and saving collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, storing collaborated imagery files from all participant cognitive collaborants locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieving collaborated imagery files from all participant cognitive collaborants stored locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files, dynamically managing and controlling with at least one or more associated databases, authorization, authentication, identity management, security, and access, publication and distribution privileges for viewing, communicating, collaborating, consulting and instructing, and cognitive collaborant privileges, including curation, annotation, tagging, encapsulation, saving, storage, retrieval and distribution of live streaming imagery data, archived imagery data, appended imagery metadata, including appended semantic metadata and annotations, collaborated annotations, and archived collaborated imagery files for each participant cognitive collaborant during collaboration sessions, including managing and controlling security tokens providing access for cognitive collaborants maintained in security metadata repositories, blockchain metadata repositories and blockchain data ledgers, enabling both synchronous and asynchronous bidirectional communications with at least one or more local area networks, at least one or more wide area networks (internet) including imagery data repositories and combinations thereof during multiple collaboration sessions, enabling identification, tracking and monitoring of participant cognitive collaborants by assignment of unique colors for annotations of streaming imagery data, archived collaborated imagery files and cognitive collaborant annotations, that include telestrations, drawings, illustrations, alpha-numeric text annotations, as well as cognitive collaborant annotations combined with alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, enabling colorized telestration, annotation and masking of colorized attention maps and colorized prediction bases for explainable artificial intelligence by participant cognitive collaborants by assignment of unique colors for annotations of streaming imagery data, archived collaborated imagery files and cognitive collaborant annotations, including telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, costs annotations, resource consumption annotations and resource utilization annotations; allowing for multiple participant cognitive collaborants, each of whom can capture live streaming imagery data together with associated imagery metadata, including semantic metadata and annotations, and bring into the collaboration session, retrieve archived streaming imagery data together with associated imagery metadata, including semantic metadata and annotations, and bring into the collaboration session, concurrently view, communicate, collaborate, consult and instruct with streaming imagery data, enabling curation, annotation and tagging that streaming imagery data with collaborated annotations that include telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, enabling encapsulation and saving collaborated streaming imagery data and archived imagery metadata, including archived semantic metadata and annotations, together with appended imagery metadata, including appended semantic metadata and annotations, and collaborated annotations and from each collaboration session, including asynchronous or synchronous collaboration with at least one or more participant cognitive collaborants, in native, single file format structures, known as collaborated imagery files, enabling multimodal clinical communications, collaboration, consultation and instruction, including viewing, curating, annotating and tagging, using at least one or more sources of streaming imagery data shared among at least one or more participant cognitive collaborants with a multi-channel stream viewer that enables capture, retrieval and concurrent viewing of both live and archived medical imagery streams together with associated metadata during various stages of medical disease and injury management, including detection, diagnosis, prognosis, treatment, measurement, monitoring and reporting, as well as workflow optimization with operational analytics for outcomes, performance, results, resource utilization, resource consumption and costs, enabling independently adding sources of streaming imagery data, adjust, enhance or reduce resolutions or frame rates of streaming imagery data with a multi-channel communications control interface, and independently view those additional channels of streaming imagery data and independently select which of those channels to bring into a collaboration session, enabling conveying instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, and not reliant upon any external communications network.

59. The method of claim 58 for the acquisition and transmission of medical streaming imagery data, including medical images, medical video, medical modality imagery, medical wave form imagery, clinical maps, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, the method preserving the clinical integrity of medical streaming imagery data from medical devices, systems and equipment cleared for medical use, including clinical diagnostic purposes, care delivery and patient monitoring, enabling both synchronous and asynchronous multimodal clinical communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, including augmented generative AI algorithms, models and systems, and heterogeneous networked teams composed thereof, including viewing, curating, annotating and tagging streaming medical imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, encapsulating and saving collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, storing collaborated imagery files from all participant cognitive collaborants locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieving collaborated imagery files from all participant cognitive collaborants stored locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files, that can be viewed, curated, annotated, tagged, encapsulated and saved together as collaborated medical imagery files and cleared for use with approved medical devices, equipment, systems, image and data repositories, in native, single file format structures, including those compliant with standards for digital imaging and communications in medicine.

60. The method of claim 58 for acquiring, transmitting, encapsulating, saving, storing, retrieving, publishing and distributing collaborated imagery files, including live or archived collaborated imagery files, collaborated annotations and tags, together with streaming imagery data, relevant imagery metadata, including semantic metadata and annotations, and appended imagery metadata, including appended semantic metadata and annotations, from the collaboration session in native, single file format structures, known as collaborated imagery files, during various stages of medical disease and injury management, including detection, diagnosis, prognosis, treatment, measurement, monitoring and reporting, as well as workflow optimization with operational analytics for outcomes, performance, results, resource utilization, resource consumption and costs.

61. The method of claim 58 for enabling the encapsulation and saving collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, during collaboration sessions practiced by and among at least one or more participant cognitive collaborants, including persons, machines, devices, neural networks, robots and algorithms, including augmented generative AI algorithms, models and systems, and heterogeneous networked teams composed thereof.

62. The method of claim 58 for enabling the storage of collaborated imagery files from all participant cognitive collaborants locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

63. The method of claim 58 for enabling the retrieval of collaborated imagery files from all participant cognitive collaborants stored locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations.

64. The method of claim 58 for enabling the publication and distribution of collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files.

65. The method of claim 58 for dynamically managing and controlling with at least one or more associated databases, authorization, authentication, identity management, security, and access, publication and distribution privileges for viewing, communicating, collaborating, consulting and instructing, and cognitive collaborant privileges, including curation, annotation, tagging, encapsulation, saving, storage, retrieval and distribution of live streaming imagery data, archived imagery data, appended imagery metadata, including appended semantic metadata and annotations, collaborated annotations, and archived collaborated imagery files for each participant cognitive collaborant during collaboration sessions, including managing and controlling security tokens providing access for cognitive collaborants maintained in security metadata repositories, blockchain metadata repositories and blockchain data ledgers.

66. The method of claim 58 for enabling both synchronous and asynchronous bidirectional communications with at least one or more local area networks, at least one or more wide area networks (internet) including imagery data repositories and combinations thereof during multiple collaboration sessions.

67. The method of claim 58 for enabling identification, tracking and monitoring of participant cognitive collaborants by assignment of unique colors for annotations of streaming imagery data, archived collaborated imagery files and cognitive collaborant annotations, that include telestrations, drawings, illustrations, alpha-numeric text annotations, as well as cognitive collaborant annotations combined with alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations.

68. The method of claim 58 for enabling colorized telestration, annotation and masking of colorized attention maps and colorized prediction bases for explainable artificial intelligence by participant cognitive collaborants by assignment of unique colors for annotations of streaming imagery data, archived collaborated imagery files and cognitive collaborant annotations, including telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, costs annotations, resource consumption annotations and resource utilization annotations.

69. The method of claim 58 for allowing for multiple participant cognitive collaborants, each of whom can capture live streaming imagery data together with associated imagery metadata, including semantic metadata and annotations, and bring into the collaboration session, retrieve archived streaming imagery data together with associated imagery metadata, including semantic metadata and annotations, and bring into the collaboration session, concurrently view, communicate, collaborate, consult and instruct with streaming imagery data, enabling curation, annotation and tagging that streaming imagery data with collaborated annotations that include telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, enabling encapsulation and saving collaborated streaming imagery data and archived imagery metadata, including archived semantic metadata and annotations, together with appended imagery metadata, including appended semantic metadata and annotations, and collaborated annotations and from each collaboration session, including asynchronous or synchronous collaboration with at least one or more participant cognitive collaborants, in native, single file format structures, known as collaborated imagery files, enabling multimodal clinical communications, collaboration, consultation and instruction, including viewing, curating, annotating and tagging, using at least one or more sources of streaming imagery data shared among at least one or more participant cognitive collaborants with a multi-channel stream viewer that enables capture, retrieval and concurrent viewing of both live and archived medical imagery streams together with associated metadata during various stages of medical disease and injury management, including detection, diagnosis, prognosis, treatment, measurement, monitoring and reporting, as well as workflow optimization with operational analytics for outcomes, performance, results, resource utilization, resource consumption and costs, enabling independently adding sources of streaming imagery data, adjust, enhance or reduce resolutions or frame rates of streaming imagery data with a multi-channel communications control interface, and independently view those additional channels of streaming imagery data and independently select which of those channels to bring into a collaboration session, enabling conveying instructions with two way communications among participant cognitive collaborants, including source channel selection, for viewing, curating, annotating and tagging imagery data streams with telestrations, drawings, illustrations, alpha-numeric text annotations, image annotations, wave form annotations, voice annotations, video annotations, augmented reality imagery annotations, 3D/4D imagery annotations, haptic annotations, document annotations, outcomes annotations, performance annotations, results annotations, resource consumption annotations, resource utilization annotations and costs annotations, and not reliant upon any external communications network.

70. The method of claim 58 for the acquisition and transmission of medical streaming imagery data, including medical images, medical video, medical modality imagery, medical wave form imagery, clinical maps, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, the method preserving the clinical integrity of medical streaming imagery data from medical devices, systems and equipment cleared for medical use, including clinical diagnostic purposes, care delivery and patient monitoring, enabling both synchronous and asynchronous multimodal clinical communications, collaboration, consultation and instruction, as well as recursive cognitive enrichment and collaborative knowledge exchange, with streaming imagery data during collaboration sessions, practiced by and among at least one or more participant cognitive collaborants, including persons, machines, devices, neural networks, robots and algorithms, including augmented generative AI algorithms, models and systems, and heterogeneous networked teams composed thereof, including viewing, curating, annotating and tagging streaming medical imagery data during various stages of medical disease and injury management, including detection, diagnosis, prognosis, treatment, measurement, monitoring and reporting, as well as workflow optimization with operational analytics for outcomes, performance, results, resource utilization, resource consumption and costs, encapsulating and saving collaborated annotations and tags together with streaming imagery data, relevant imagery metadata, including semantic metadata and annotations, and appended imagery metadata, including appended semantic metadata and annotations, from the collaboration session in native, single file format structures, known as collaborated imagery files, storing collaborated imagery files from all participant cognitive collaborants locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, retrieving collaborated imagery files from all participant cognitive collaborants stored locally in media libraries or image data repositories on their respective computer storage devices, in image data repositories on tele-visual imagery informatics management system servers, in image data repositories on cloud storage devices and locations, in image data repositories on picture archiving and communications systems, in other image data repositories compliant with standards for digital imaging and communications in medicine, or in any other data repository that allows streaming imagery data, annotations and metadata, including semantic metadata and annotations, to be combined in native single file format structures, including in such locations as data containers and data catalogs, clinical data repositories, personalized clinical knowledge repositories, clinical cognitive vismeme vaults and metadata repositories, on premises, as well as on cloud storage devices and locations, publishing and distributing collaborated imagery files in known native, single file format structures, including those used for digital imaging and communications in medicine comprising both core and non-core data element tags, together with conformance statements that enable prior evaluation and testing of streaming imagery equipment components without an actual physical connection, all of which facilitate network connectivity for imagery equipment components, communication interoperability for imagery data systems, and exchange of collaborated imagery files, that can be viewed, curated, annotated, tagged, encapsulated and saved together as collaborated medical imagery files and cleared for use with approved medical devices, equipment, systems, image and data repositories, in native, single file format structures, including those compliant with standards for digital imaging and communications in medicine.

71. The method of claim 58 for acquiring, transmitting, encapsulating, saving, storing, retrieving, publishing and distributing collaborated imagery files, including live or archived collaborated imagery files, collaborated annotations and tags, together with streaming imagery data, relevant imagery metadata, including semantic metadata and annotations, and appended imagery metadata, including appended semantic metadata and annotations, from the collaboration session in native, single file format structures, known as collaborated imagery files, during various stages of medical disease and injury management, including detection, diagnosis, prognosis, treatment, measurement, monitoring and reporting, as well as workflow optimization with operational analytics for outcomes, performance, results, resource utilization, resource consumption and costs, that can be viewed, curated, annotated, tagged, encapsulated and saved together as collaborated medical imagery files and cleared for use with approved medical devices, equipment, systems, image and data repositories, in native, single file format structures, including those compliant with standards for digital imaging and communications in medicine.

72. The method of claim 58 for archived collaborated imagery files that can be retrieved for use together with streaming imagery data during synchronous or asynchronous collaboration sessions, revised, appended, viewed, curated, annotated, tagged, encapsulated and saved in native, single file format structures, including those compliant with standards for digital imaging and communications in medicine, during collaboration sessions practiced by and among at least one or more participant cognitive collaborants, including persons, machines, devices, neural networks, robots and algorithms, including augmented generative AI algorithms, models and systems, and heterogeneous networked teams composed thereof, and made available for use together with streaming imagery data during current or subsequent collaboration sessions.

73. The method of claim 58 for non-clinical workflows, comprising: receiving and transmitting non-medical streaming data; enabling cognitive collaborants to curate, annotate, and encapsulate data in single file formats for rapid adaptive learning in education or business settings.

74. The method of claim 58 enabling model context protocols (MCP) for standardized context propagation in agentic AI workflows, with semantic registries for federated interoperability across non-clinical domains.

75. The method of claim 58 for cybernetic resilience in non-clinical settings, comprising: sensing early signals with generative AI; rewiring resources via networked teams; locking in learnings with governance policies for adaptation.

76. The method of claim 58 for spatial computing in AR/VR, enabling immersive reskilling with multisensory data stream visualization for specialist skills acquisition in non-medical fields.

77. The method of claim 58 enabling personal knowledge repositories (PKRs) for documenting best practices in non-healthcare, with searchable vaults for value chain knowledge exchange.

78. The method of claim 58 for non-biomedical problem-solving, comprising: multi-agent frameworks with human-AI hybrids for creative contexts, integrating Graph RAG for viability scoring.

79. The method of claim 58 for non-PHI business workflows, using semantic knowledge graphs for multi-domain fusion in finance/engineering decision support.

80. The method of claim 58 for federated learning in non-medical repositories, enabling privacy-preserving model training across distributed knowledge vaults.

81. The method of claim 58 for multisensory data exchange in education, using semiotics/semantics/somesthetics for immersive learning with haptic annotations.

82. The method of claim 58 for recursive cognitive enrichment in business, with value chain integration for knowledge creation/visualization/replication.

83. The method of claim 58 for informatics-enriched innovation in manufacturing, using multimodal communications for workflow optimization.

84. The method of claim 58 for change resilience in non-clinical settings, comprising emergent self-organizing teams of networked minds, machines, languages and tools that purposefully adapt, collaborate and innovate, sensing early signals with generative AI; rewiring resources via cybernetic teams; locking in learnings with governance policies.

85. The method of claim 58 for integrating Mershin's Rosetta Stone approach to translate between biological and digital signals in non-clinical multiomic workflows, enabling recursive enrichment with spatial multiomic data.

86. The method of claim 58 for HCLS (healthcare and life sciences) optimization, incorporating Huang's AI-driven acceleration for radiogenomic and pathomic data analysis in heterogeneous teams.

87. The method of claim 58 for re-skilling knowledge workers, based on HBS guide, with multimodal media for adaptive learning in AI-augmented environments.

88. The method of claim 58 for creating virtuous circles in collaborative networks, integrating multiomic maps and heat maps for workflow optimization in non-medical sectors.

89. The method of claim 58 for deep dive AI requirements in PMWC25, using Graph RAG for viability scoring in agentic AI for precision decision-making.

90. The method of claim 58 for BICA-LEAP inspired cognitive architectures, enabling federated interoperability in non-PHI knowledge repositories.

91. The method of claim 58 for spatial computing with AR/VR, integrating somesthetics for immersive multisensory data visualization in reskilling.

92. The method of claim 58 for personal clinical knowledge repositories extended to non-healthcare, with searchable vaults for best practices.

93. The method of claim 58 for privacy-preserving federated learning across distributed vaults, for model training in education and business.

94. The method of claim 58 for semiotics and semantics in education, with haptic annotations for multisensory immersive learning.

95. The method of claim 58 for value chain integration in business, with recursive enrichment for knowledge creation and replication.

96. The method of claim 58 for Mershin's TEDx insights on bio-nano interfaces, enabling wave form and haptic integration in collaboration.

97. The method of claim 58 for HBS cybernetic teams in adaptation, sensing signals for rewiring resources in AI workflows.

98. The method of claim 58 for virtuous circles in VNN, using data stream visualizations for performance monitoring.

99. The method of claim 58 for MCP in agentic AI, with semantic registries for context propagation in federated systems.

100. The method of claim 58 for semantic knowledge graphs in business, fusing data for decision support in finance.

101. The method of claim 58 for PKRs in education, documenting practices with searchable cognitive vismeme vaults.

102. The method of claim 58 for tokenized economies, with vismemes as NFTs for knowledge trading in manufacturing.

103. The method of claim 58 for non-PHI fusion, using hypergraphs for multi-domain analytics in engineering.

104. The method of claim 58 for multisensory exchange, semiotics for learning with 3D/4D annotations.

105. The method of claim 58 for cognitive enrichment, value chain for replication in informatics innovation.

106. The method of claim 58 for cybernetic teammate integration, comprising human-AI hybrid collaboration for resilience-building scenarios with emergent network organization among cognitive collaborants.

107. The method of claim 58 for continuous learning pipelines, comprising recursive cognitive enrichment for ongoing professional development with cumulative knowledge accumulation in vismeme vaults.

108. The method of claim 58 for value chain integration, comprising knowledge creation, visualization, and replication across organizational boundaries with recursive enrichment through value network nodes.

109. The method of claim 58 for autonomous sub-agent spawning, comprising dynamic creation of specialized agents for complex problem decomposition with Graph-RAG integration.

110. The method of claim 58 for cybernetic closed-loop resilience, comprising continuous adaptation with feedback integration in agentic systems to reorganize uncertainty into auditable neurosynaptic traces.

111. The method of claim 58 for agentic workflow orchestration, comprising coordinated execution across heterogeneous AI agents with semantic context propagation through the institutional graph of value network nodes.

112. The method of claim 58 for morpholomic data processing, comprising morphological feature extraction for machine-learning-based analysis.

113. The method of claim 58 for radiogenomic analysis, comprising correlation of imaging features with genomic markers for treatment stratification.

114. The method of claim 58 for clinically actionable biomarker identification, comprising AI-driven discovery from integrated multiomic data streams.

115. The method of claim 58 for precision medicine information sciences, comprising transformation of multiomic data into personalized treatment recommendations.

116. The method of claim 58 for AI transparency in cognitive collaboration, comprising audit trails that encode an auditable, revisitable causal structure for each recommendation.

117. The method of claim 58 for model interpretability, comprising feature-importance ranking with natural language explanations linked to corresponding vismemes.

118. The method of claim 58 for AI governance in healthcare, comprising policy enforcement with explainable decision logging across value network nodes.

119. The method of claim 58 for FDA-aligned AI transparency, comprising documentation of training data, model architecture, and validation results in a form suitable for regulatory review.

120. The method of claim 58 for clinical workflow orchestration, comprising AI-driven task routing with cognitive collaborant assignment along end-to-end clinical workflows.

121. The method of claim 58 for health information exchange, comprising secure vismeme transmission across institutional boundaries using standardized messaging protocols.

122. A method enabling multichannel multiplexed communications, collaboration, consultation and instruction, as well as recursive cognitive enrichment and collaborative knowledge exchange, with streaming imagery data by participant cognitive collaborants, including persons, machines, devices, neural networks, robots and algorithms, including augmented generative AI algorithms, models and systems, and heterogeneous networked teams composed thereof, with modular and scalable clusters of gateway streamer servers configured to support multiple network topologies, including peer-to-peer, hub-and-spoke, mesh chord and core-spine-leaf networks, as well as in 2-tier, 3-tier, or N-tier application architectures, and heterogeneous network combinations thereof, each gateway streamer server enabling neurosynaptic network connectivity enabling both synchronous and asynchronous multimodal clinical communications, collaboration, consultation and instruction, as well as recursive cognitive enrichment and collaborative knowledge exchange, that includes viewing, curating, annotating and tagging, using at least one or more sources of multichannel, multiplexed heterogeneous streaming imagery data, including both medical and non-medical streaming imagery data, multimodal media and combinations thereof, and together with images, video, modality imagery, waveforms, audio and haptic files, multiomic data—phenotypic, genomic, metabolomic, pathomic, radiomic, radiopathomic, radiogenomic, spatial multiomic and morpholomic data, maps and clinical data sets used in computer-assisted drug design and treatment, biometric maps and movies, hapmaps, heat maps, data stream visualizations, structured reports, interactive media reports, including interactive multimedia reporting, clinical documents and key performance indicators, including indicators of quality of care, as well as indicators of clinical, operational and financial performance, during various stages of medical disease and injury management, including detection, diagnosis, prognosis, treatment, measurement, monitoring and reporting, as well as workflow optimization with operational analytics for outcomes, performance, results, resource utilization, resource consumption and costs.

123. The network of claim 122, wherein said emergent self-organizing teams actively learn and purposefully adapt, collaborate, and innovate during task execution with recursive cognitive enrichment across value network nodes.

124. The network of claim 122, further comprising adaptive collaborative innovation with emergent network organization for novel problem-solving in dynamic clinical and non-clinical environments.

125. The network of claim 122, wherein said emergent self-organizing teams fashion collaborated solutions for novel problems or complex tasks by treating institutions as communication networks and causal graphs among cognitive collaborants.

126. The network of claim 122, wherein emergent network organization enables self-organizing networked teams of minds, machines, languages, and tools to share knowledge, language, cognition, and technology through neurosynaptic vismeme workflows.

127. The network of claim 122, further comprising multi-parametric, multi-sensory signal intelligence and packetized augmented cognition across a brain-like, small-world, scale-free neurosynaptic network of value network nodes.

128. The network of claim 122, wherein said value network nodes form a neurosynaptic institutional network that records auditable, revisitable causal structure for decisions, including human rationales, AI attribution graphs, and workflow histories stored as vismemes.

* * * * *